US011906516B2

(12) United States Patent
Mai et al.

(10) Patent No.: US 11,906,516 B2
(45) Date of Patent: *Feb. 20, 2024

(54) SENSOR FOR THE DETECTION OF BIOMOLECULES

(71) Applicant: Sony Corporation, Tokyo (JP)

(72) Inventors: Michaela Mai, Stuttgart (DE); Anthony Roberts, Stuttgart (DE); Tzenka Miteva, Stuttgart (DE); Gabriele Nelles, Stuttgart (DE); Jan Rother, Stuttgart (DE)

(73) Assignee: Sony Corporation, Tokyo (JP)

( * ) Notice: Subject to any disclaimer, the term of this patent is extended or adjusted under 35 U.S.C. 154(b) by 24 days.

This patent is subject to a terminal disclaimer.

(21) Appl. No.: 16/085,722

(22) PCT Filed: Mar. 23, 2017

(86) PCT No.: PCT/EP2017/056917
§ 371 (c)(1),
(2) Date: Sep. 17, 2018

(87) PCT Pub. No.: WO2017/167633
PCT Pub. Date: Oct. 5, 2017

(65) Prior Publication Data
US 2020/0166502 A1    May 28, 2020

(30) Foreign Application Priority Data
Mar. 31, 2016 (EP) .................................... 16163436

(51) Int. Cl.
*G01N 33/544* (2006.01)
*G01N 21/64* (2006.01)
*G01N 33/543* (2006.01)

(52) U.S. Cl.
CPC ....... *G01N 33/544* (2013.01); *G01N 21/6428* (2013.01); *G01N 33/54326* (2013.01);
(Continued)

(58) Field of Classification Search
CPC ......... G01N 21/6486; G01N 33/54346; G01N 33/544; G01N 21/648; G01N 33/54326; G01N 21/6428; G01N 2021/6439
See application file for complete search history.

(56) References Cited

U.S. PATENT DOCUMENTS

2005/0148100 A1    7/2005  Su et al.
2006/0140240 A1    6/2006  Chen
(Continued)

FOREIGN PATENT DOCUMENTS

CN        103289674 A      9/2013
EP          2421376 A0      2/2012
WO   WO 2013/113990 A1    8/2013

OTHER PUBLICATIONS

International Search Report and Written Opinion dated Jun. 26, 2017, in PCT/EP2017/056917, filed Mar. 23, 2017.
(Continued)

*Primary Examiner* — Shafiqul Haq
(74) *Attorney, Agent, or Firm* — Oblon, McClelland, Maier & Neustadt, L.L.P.

(57) ABSTRACT

The present disclosure relates to a sensor for the detection of analytes, in particular for the detection of biomolecules. The sensor includes a (bio)compatible sensing layer including a polymer matrix or gel matrix, particularly a polymer gel matrix, organic nanoparticles and, optionally, one or several cell adhesion layer(s). The cell adhesion layer(s) can be varied depending on the type of cells. In the presence of the analytes, the organic nanoparticles are capable of photon up-conversion emission. The sensor further optionally
(Continued)

includes plasmonic metal nanoparticles. The present disclosure further relates to methods of producing such a sensor and to uses of such a sensor.

17 Claims, 15 Drawing Sheets

(52) U.S. Cl.
CPC .......... *G01N 33/54346* (2013.01); *G01N 2021/6439* (2013.01)

(56) References Cited

U.S. PATENT DOCUMENTS

| | | |
|---|---|---|
| 2010/0330026 A1 | 12/2010 | Miteva et al. |
| 2013/0236555 A1 | 9/2013 | Miteva et al. |
| 2014/0378831 A1 | 12/2014 | Park et al. |
| 2019/0047243 A1* | 2/2019 | Bertrand ............... B31B 70/005 |

OTHER PUBLICATIONS

Zhou, J. et al., Upconversion Luminescent Materials: Advances and Applications, Chemical Reviews, vol. 115, No. 1, Jan. 14, 2015, pp. 395-465, XP 055344180.

* cited by examiner

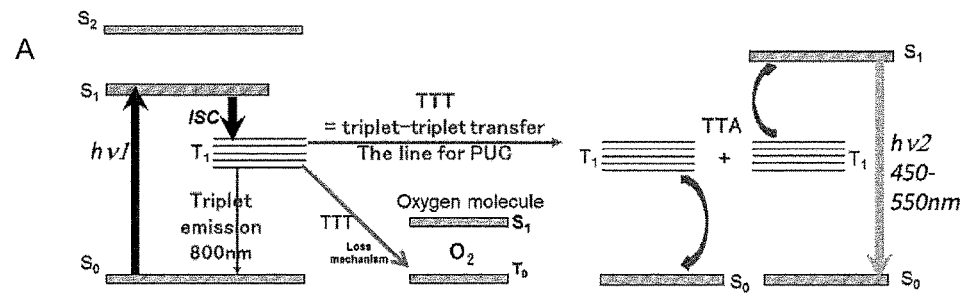
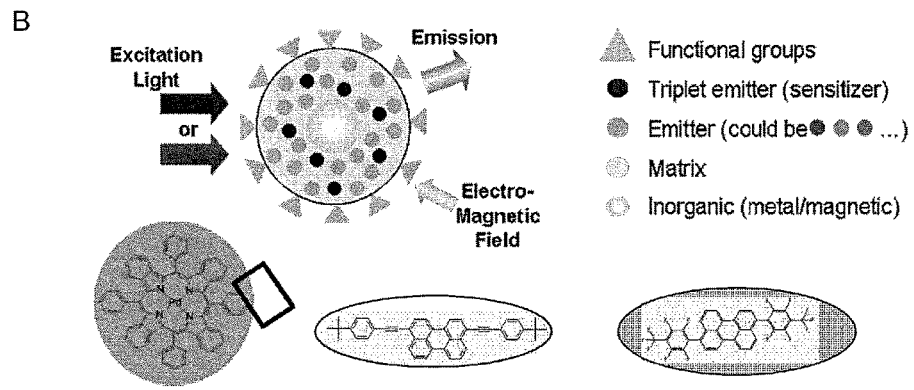
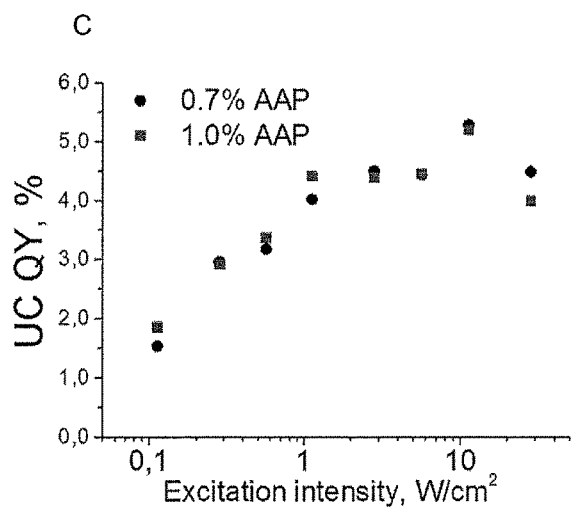
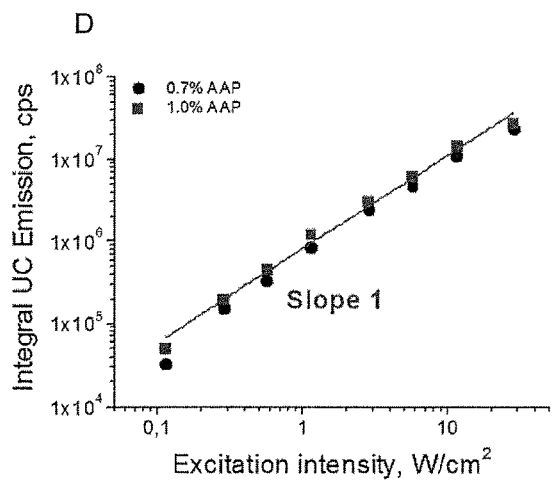
Fig. 1

Fig. 2 A-D

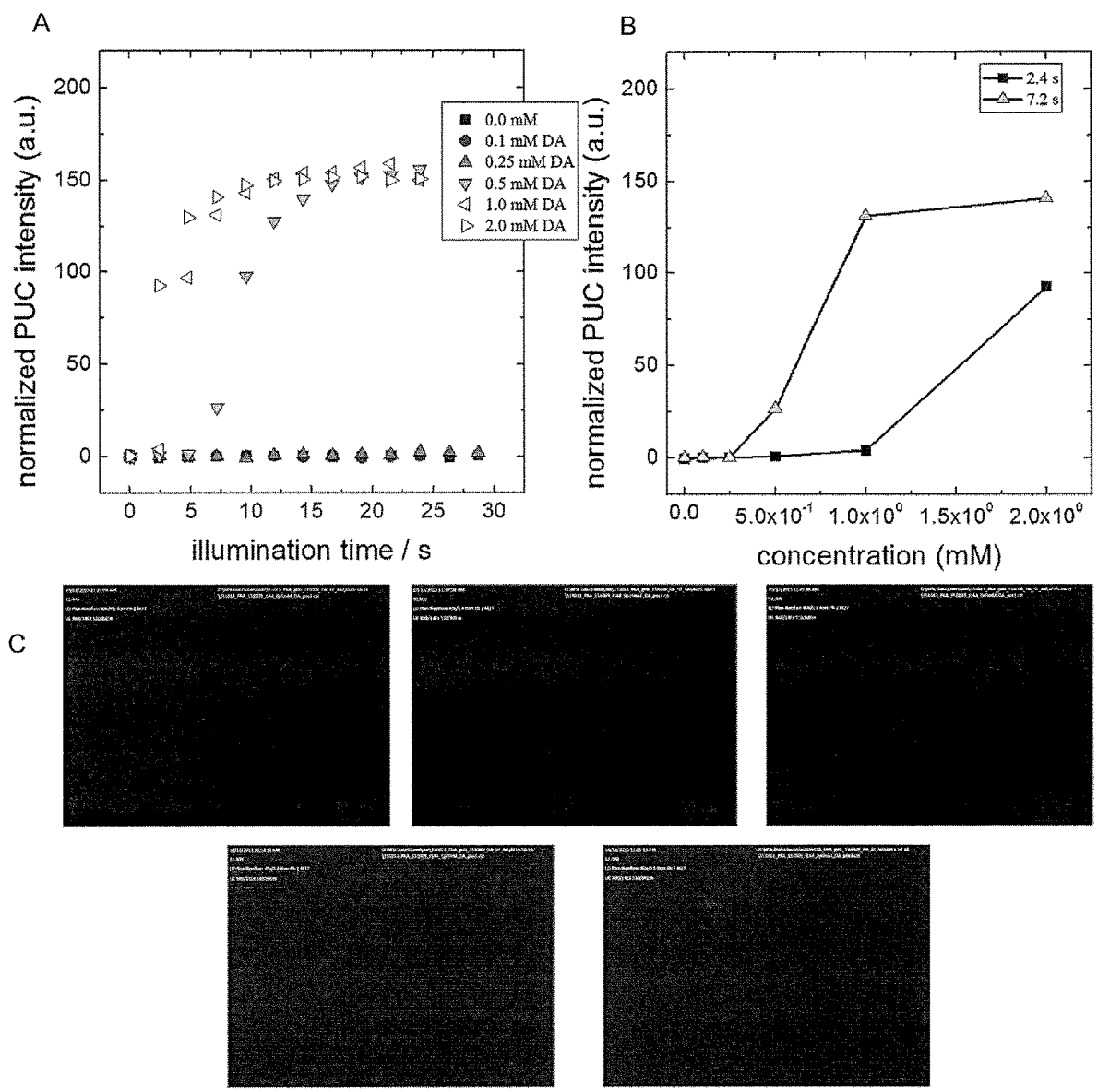
Fig. 4 A, B and C

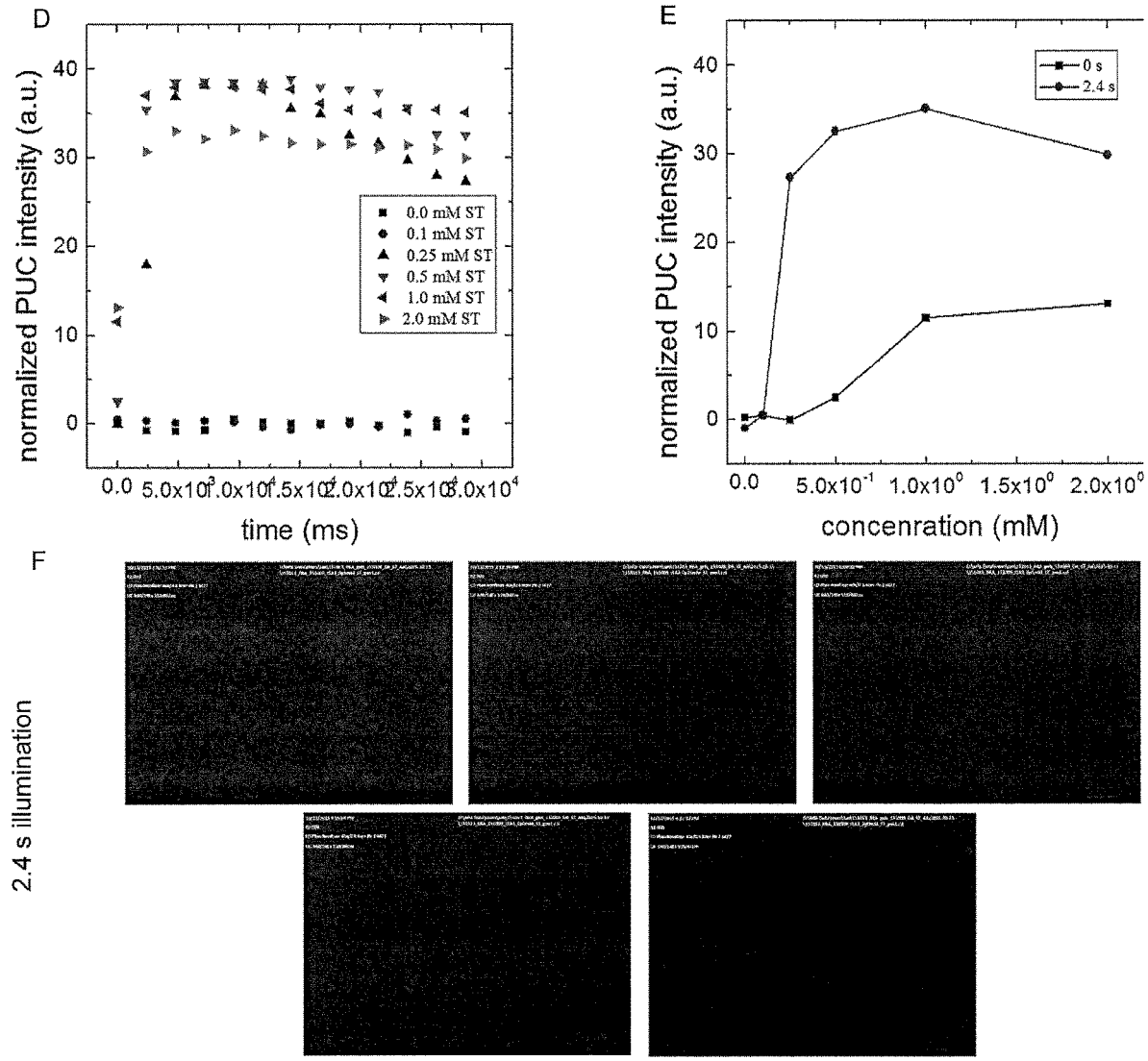
Fig. 4 D, E and F

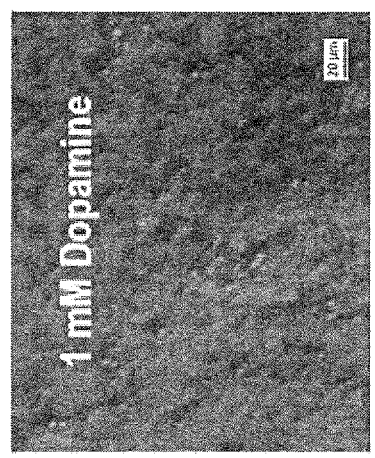
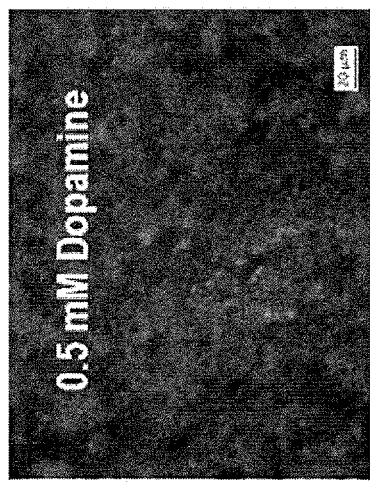
Fig. 7 A, B and C

E
 
Fig. 7 E

Fig. 8 A, B, C

Polyacrylamide gels

SENSOR FOR THE DETECTION OF BIOMOLECULES

BACKGROUND

The field of the DISCLOSURE lies in the area of sensors for the detection of analytes, in particular for the detection of biomolecules, based on organic luminescent nanoparticles.

The present disclosure relates to a sensor for the detection of analytes, in particular for the detection of biomolecules. The sensor includes a (bio)compatible sensing layer including a polymer matrix or gel matrix, particularly a polymer gel matrix, organic nanoparticles and, optionally, one or several cell adhesion layer(s). The cell adhesion layer(s) can be varied depending on the type of cells. In the presence of the analytes, the organic nanoparticles are capable of photon up-conversion emission. The sensor further optionally includes plasmonic metal nanoparticles The present disclosure further relates to methods of producing such a sensor and to uses of such a sensor.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, as well as aspects described in this background section in relation to nanoparticles, sensors and sensing layers are neither expressly nor implicitly admitted as prior art against the present disclosure.

Sensors and methods that allow for the specific detection of analyte molecules are of great importance in various fields. Neuronal research, for example, is a continuously growing research field, especially in medical and pharmaceutical related areas. In this regard, fast, sensitive, and specific tools for the detection of biomolecules (in particular related to neuronal cell functions) and their visualization are needed.

For live cell imaging, fluorescence probes are state of the art; however, such probes are often limited by low signal intensities, and/or background/auto-fluorescence, leading to poor signal-to-noise and signal-to-background ratios. Furthermore, in vitro or in vivo molecular imaging techniques are mainly based on specific biomolecule interactions such as antibody/antigen recognition.

High-pressure liquid chromatogaphy (HPLC) and luminescence or fluorescence-based methods—such as the enzyme-linked immunoabsorbant assay (ELISA)—are state-of-the-art for biomolecule detection, such as for neurotransmitter detection. The main disadvantge of these techniques is that they are off-line techniques and thus cannot be readily used for real-time in vivo or in vitro imaging. On the other hand, Aall fluorescent cell labeling/penetrating materials, small molecules as well as polymers (DNA or protein based), have the common problems of background fluorescence, fluorescence cross-talk of the dyes, low reproducibility due to batch-to-batch variations and unspecific binding properties.

In the field of sensing layers, the known and commercially available sensing layers are fluorophore-doped polymer layers that allow for cell growth on top and within the layer. The sensing relies on the fact that cells destroy the polymer of the layer and thus the fluorescence of the film gradually disappears at sites where cells are present. Such layers are used for motility assays. However, they do not offer any specificity/do not detect any analyte and actually only "sense" the presence of cells.

Chip-based methods in combination with nanotechnology are emerging techniques. However, such approaches have the disadvantages that the chips have to be made cell compatible and the pixel size severely limits the imaging resolution.

SUMMARY

The present disclosure provides a sensor for the detection of an analyte, said sensor including a cell-compatible sensing layer including
- a matrix, wherein said matrix is a polymer matrix or polymer gel matrix, and
- organic nanoparticles embedded in said matrix, wherein said organic nanoparticles are capable of emitting light by photon up-conversion emission in the presence of said analyte, but not in the absence of said analyte, wherein said sensor further optionally includes plasmonic metal nanoparticles, and optionally, one or several cell adhesion layer(s).

The present disclosure provides a method of producing a sensor according to the present disclosure, said sensor including a biocompatible sensing layer including
- a matrix, wherein said matrix is a polymer matrix or polymer gel matrix, and
- organic nanoparticles embedded in said matrix, wherein said organic nanoparticles are capable of emitting light by photon up-conversion emission in the presence of said analyte, but not in the absence of said analyte;

wherein said sensor further optionally includes plasmonic metal nanoparticles, and optionally, one or several cell adhesion layers;

said method including the steps of:

(Variant A: metal nanoparticles distributed in polymer matrix or gel matrix:)
- providing, in any order, organic nanoparticles capable of emitting light by photon up-conversion emission (=PUC organic nanoparticles), plasmonic metal nanoparticles, polymer(s) for forming said polymer matrix or precursors of said gel matrix, and a substrate, optionally with attachment layer/coating thereon; and
- either, for the preparation of a polymer matrix: preparing a dispersion including said PUC organic nanoparticles and said metal nanoparticles in a water-based solution of the polymer(s) for forming said polymer matrix;
- applying the dispersion onto said substrate or onto the attachment layer/coating if present on said substrate);
- drying the applied dispersion, thus forming a sensing layer;
- optionally, applying cell adhesion layer(s) on top via drop casting followed by washing;
- or, for the preparation of a gel matrix: preparing a dispersion including said PUC organic nanoparticles and said metal nanoparticles in a solution of the gel precursors and gel polymerisation initiators for forming said gel matrix;
- applying the dispersion, particularly a droplet thereof, onto said substrate or onto the attachment layer/coating if present on said substrate;
- placing a thin glass, such as a microscope slide cover slip, with hydrophobic surface on top of the dispersion to define thickness of said gel matrix and allowing the gel to polymerize;

removing the thin glass;
optionally, applying cell adhesion layer(s) on top via drop casting followed by washing;
thereby providing a cell compatible sensor;
or said method including the steps of:
(Variant B: metal nanoparticles distributed in a separate enhancement layer:)
providing, in any order, organic nanoparticles capable of emitting light by photon up-conversion emission (=PUC organic nanoparticles), polymer(s) for forming said polymer matrix or precursors of said gel matrix, a substrate, optionally with attachment layer/coating thereon, a metal material in a form suitable to be applied as a separate layer, either in the form of a layer of plasmonic metal nanoparticles or a thin layer of metal deposited via vacuum deposition, said layer of metal nanoparticles or said thin layer of metal being capable of enhancing light emitted by said organic nanoparticles by way of plasmon enhancement, wherein particularly said thin layer of metal or said layer of metal nanoparticles has a thickness of approximately 10-50 nm;
applying said thin layer of metal or said layer of metal nanoparticles onto said substrate, thereby forming an enhancement layer on said substrate for enhancement of light emitted by said organic nanoparticles;
and thereafter forming a sensing layer on top of said enhancement layer by the following steps:
either, for the preparation of a polymer matrix: preparing a dispersion including said PUC organic nanoparticles in a water-based solution of the polymer(s) for forming said polymer matrix;
applying the dispersion onto said substrate or onto the attachment layer/coating if present on said substrate;
drying the applied dispersion, thus forming a sensing layer;
optionally, applying cell adhesion layer(s) on top via drop casting followed by washing;
or, for the preparation of a gel matrix: preparing a dispersion including said PUC organic nanoparticles in a solution of the gel precursors and gel polymerisation initiators for forming said gel matrix;
applying the dispersion, particularly a droplet thereof, onto said substrate or onto the attachment layer/coating if present on said substrate;
placing a thin glass, such as a microscope slide cover slip, with hydrophobic surface on top of the dispersion to define thickness of said gel matrix and allowing the gel to polymerize;
removing the thin glass, thus forming a sensing layer;
optionally, applying cell adhesion layer(s) on top via drop casting followed by washing;
or alternatively first forming a sensing layer on the substrate by the above-mentioned sequence of steps and thereafter forming an enhancement layer on said sensing layer by the above-mentioned sequence of steps, or, alternatively, first forming an enhancement layer on said substrate, thereafter forming a sensing layer, and thereafter forming a second enhancement layer on top of said sensing layer;
thereby providing a cell compatible sensor;
or said method including the steps of:
(Variant C: metal nanoparticles distributed within organic nanoparticles:)
providing, in any order, organic nanoparticles capable of emitting light by photon up-conversion emission (=PUC organic nanoparticles), said PUC organic nanoparticles containing metal nanoparticles inside, in particular plasmonic metal nanoparticles, further providing, in any order, a radical scavenger, in particular an antioxidant, and additional plasmonic metal nanoparticles, polymer(s) for forming said polymer matrix or precursors of said gel matrix, and a substrate, optionally with attachment layer/coating thereon;
either for the preparation of a polymer matrix: preparing a dispersion including said PUC organic nanoparticles containing inside metal nanoparticles, and antioxidant and said additional metal nanoparticles in a water-based solution of the polymer(s) for forming said polymer matrix;
applying the dispersion onto said substrate or onto the attachment layer/coating if present on said substrate;
drying the applied dispersion, thus forming a sensing layer;
optionally, applying cell adhesion layer(s) on top via drop casting followed by washing;
or, for the preparation of a gel matrix: preparing a dispersion including said PUC organic nanoparticles and said additional metal nanoparticles in a solution of the gel precursors and gel polymerisation initiators for forming said gel matrix;
applying the dispersion, particularly a droplet thereof, onto said substrate or onto the attachment layer/coating if present on said substrate;
placing a thin glass, such as a microscope slide cover slip, with hydrophobic surface on top of the dispersion to define thickness of said gel matrix and allowing the gel to polymerize;
removing the thin glass;
optionally, applying cell adhesion layer(s) on top via drop casting followed by washing;
thereby providing a cell compatible sensor.
The present disclosure provides a use of a sensor according to the present disclosure for the detection of an analyte, particularly a biomolecule secreted by cultured cells, in a sample e.g. directly in cell culture.
The present disclosure provides a method for the detection of an analyte, particularly a biomolecule secreted by cultured cells, in a sample, wherein said method includes the steps of
providing a sensor according to the present disclosure, said sensor including a cell compatible sensing layer including
a matrix, wherein said matrix is a polymer matrix or polymer gel matrix, and
organic nanoparticles embedded in said matrix, wherein said organic nanoparticles are capable of emitting light by photon up-conversion emission in the presence of said analyte, but not in the absence of said analyte, wherein said sensor further optionally includes plasmonic metal nanoparticles;
optionally, a cell adhesion layer with or without attachment layer beforehand;
positioning the cells on top of the sensor and keeping and imaging the cells in cell culture in conditions typical/desired for the cells;
thus bringing said sensor in contact with said sample, such that said analyte, if released by the cells and present in said sample, can enter into said sensing layer of the sensor;
irradiating said sensor with light having a wavelength that equals the excitation wavelength for photon up-conversion of said organic nanoparticles;

detecting light emission at the emission wavelength of photon up-conversion of said organic nanoparticles, wherein the presence and, optionally, the concentration of said analyte is determined by the intensity of the light emission detected at the emission wavelength of photon up-conversion of said organic nanoparticles.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1 shows:
(A) Jablonski Diagram of the up-conversion mechanism in presence and absence of molecular oxygen. The sensitizer molecule is excited by absorption a photon with hv1. Via intersystem crossing, the triplet state of the sensitizer is predominantly occupied within ns. In the absence of oxygen, triplet-triplet energy transfer takes place between the sensitizer and the emitter molecule. Two emitters in triplet state can now undergo triplet-triplet annihilation leading to one emitter back in ground state and one emitter with an occupied excited singlet state, which can emit anti-Stokes shifted light with energy $hv_2$. In the presence of oxygen, the energy is transferred to molecular oxygen in triplet state producing singlet oxygen.
(B) Schematic drawing of a photon upconversion nanoparticle (PUC NP) composition. Luminescent organic nanoparticles for photon upconversion. An emitter and a sensitizer are included. The darkest grey circles are the sensitizer molecules. The sensitizers can have variable absorption wavelengths as described in the embodiments/claims. For the emitters which are shown in differently shaded lighter grey circles, the different shades of grey mean that the emitters can have variable absorption/emission wavelengths as described in the embodiments/claims. In the center of the nanoparticle, there is the enhancing plasmonic nanoparticle; additionally, the matrix can contain an antioxidant.
(C) Characterization of PUC (photon upconversion) NPs (nanoparticles) by QY (quantum yield): QY of PUC in absence of molecular oxygen (anaerobic conditions) as a function of illumination intensity. The QY remains constant for intensity variation between 1 and 10 W/cm2.
(D) The intensity dependence of the PUC emission integral amount for different excitation intensities (anaerobic conditions). In the range 0.4 to 10 W/cm2 excitation a linear dependence is confirmed.

FIG. 4 shows:
(A) normalized PUC intensity in dependence of the illumination time with non-coherent light at 638 nm with an intensity of 2.3 W/cm$^2$ at different dopamine concentrations.
(B) normalized PUC intensity as a function of the dopamine concentration at different illumination times.
(C) Images of PUC emissive sensing layer at different concentrations of dopamine after 7.2 s of illumination with non-coherent light at 638 nm with an intensity of 2.3 W/cm2. All images were taken at the same area.
(D) normalized PUC intensity in dependence of the illumination time with non-coherent light at 638 nm with an intensity of 2.3 W/cm$^2$ at different serotonin concentrations.
(E) normalized PUC intensity as a function of the ST concentration at different illumination times.
(F) Images of PUC emissive sensing layer at different concentrations of serotonin after 2.4 s of illumination with non-coherent light at 638 nm with an intensity of 2.3 W/cm$^2$. All images were taken at the same area.

FIGS. 7 (B) and (C) shows data obtained with a sensor according to the present disclosure adapted to the detection of dopamine in an experiment (C) in the presence of 0.5 mM dopamine (B), and in the presence of 1 mM dopamine (C). The medium is on top of the sensor/sensing layer. Then, 0.5 mM and 1 mM (final concentration) of the neurotransmitter dopamine was pipetted on the layer into the complete growth medium. All images are Photon up-conversion (PUC) images (excitation 638 nm). Standard imaging duration was 2 s. After each PUC image, a fluorescence image with 488 nm excitation for 100 ms (control or image for normalization) was taken. The control image obtained in the absence of dopamine is completely black (data shown in 7A), the images obtained in the presence of 0.5 mM dopamine are clearly brighter than the control image obtained in the absence of dopamine, whereas the images obtained in the presence of 1 mM dopamine are again much brighter than the image obtained in the presence of 0.5 mM dopamine. (D) shows the normalization of a photon up-conversion image (633 nm) to a fluorescence image (488 nm) leading to improvement of sensing quality for both, 0.5 mM and 1 mM dopamine. The normalized images confirmed a resolution higher than 10 µm density. The normalized image obtained in the presence of 1 mM dopamine had the expected increase in brightness compared to the normalized image obtained in the presence of 0.5 mM dopamine.

(E) shows the successful imaging of dopamine at a concentration as low as 0.1 mM with a sensor according to the present disclosure (same procedure as described above). The image obtained in the presence of 0.1 mM dopamine is clearly brighter than the image obtained in the absence of dopamine.

Figure 8:
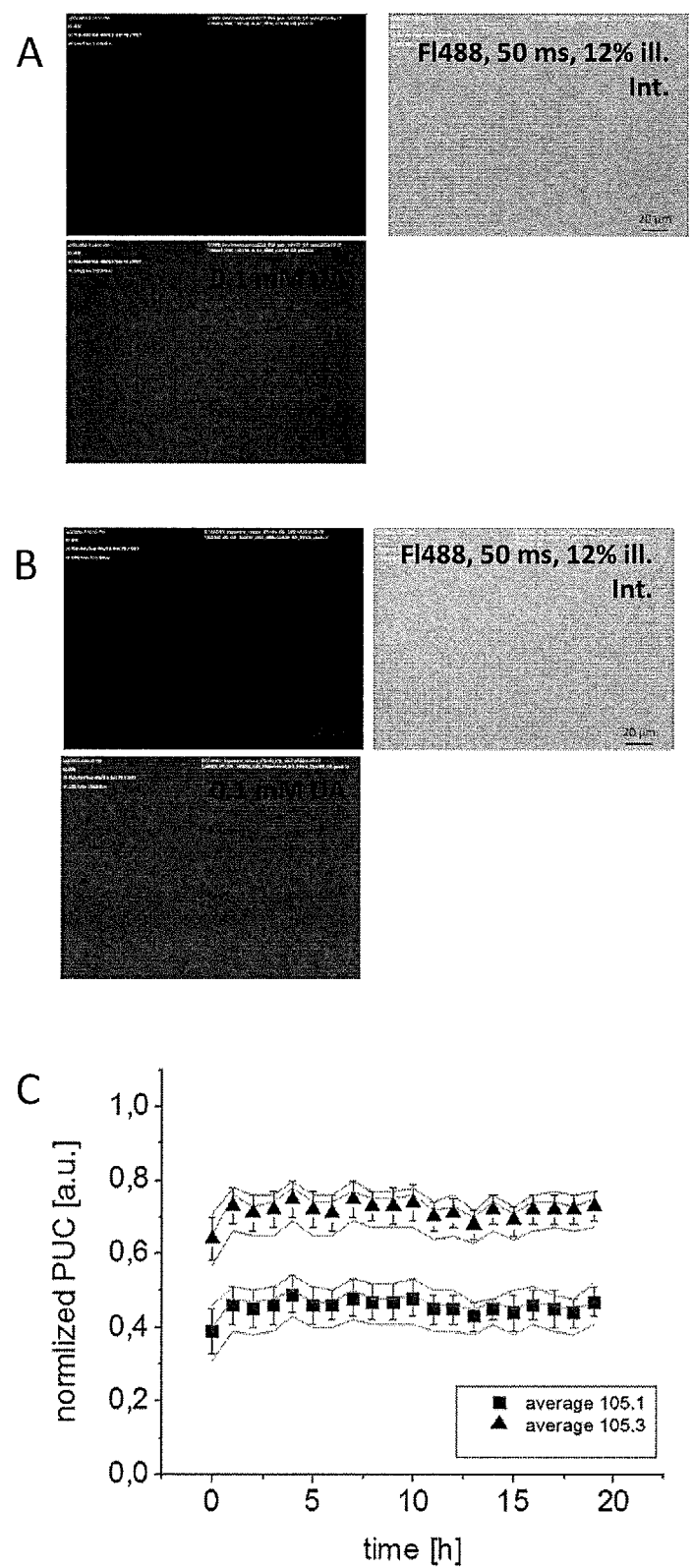

FIG. 8 shows data obtained from an experiment to examine layer stability of sensing layers as included in the sensor according to the present disclosure. For the figures shown in A and B the ESL as shown in C with NPs with higher sensitizer concentration were used. FIG. 8A: Left: Photon upconversion signal of an ESL directly after preparation. The dark image is taken with HBSS without dopamine and below it is the image with 0.1 mM dopamine in the HBSS. incubated with 0.0 mM dopamine and 0.1 mM in HBSS. Right: corresponding fluorescence imaged at 488 nm illumination. FIG. 8B: Left: Photon upconversion signal of an ESL after 15 days at 37° C. and 5% $CO_2$ with CDI iCell DopaNeuron cells growing on the layers. The dark image is HBSS without dopamine and below it with 0.1 mM dopamine in the HBSS. Right: corresponding fluorescence imaged at 488 nm illumination. FIG. 8C: Changes of the normalized PUC signal (under nitrogen 95% and CO2 5% atmosphere at 37° C.) over 24 h. The PUC NPs batches 105.1 and 105:3 contain different amount of sensitizer PdTBP.

Figure 9:
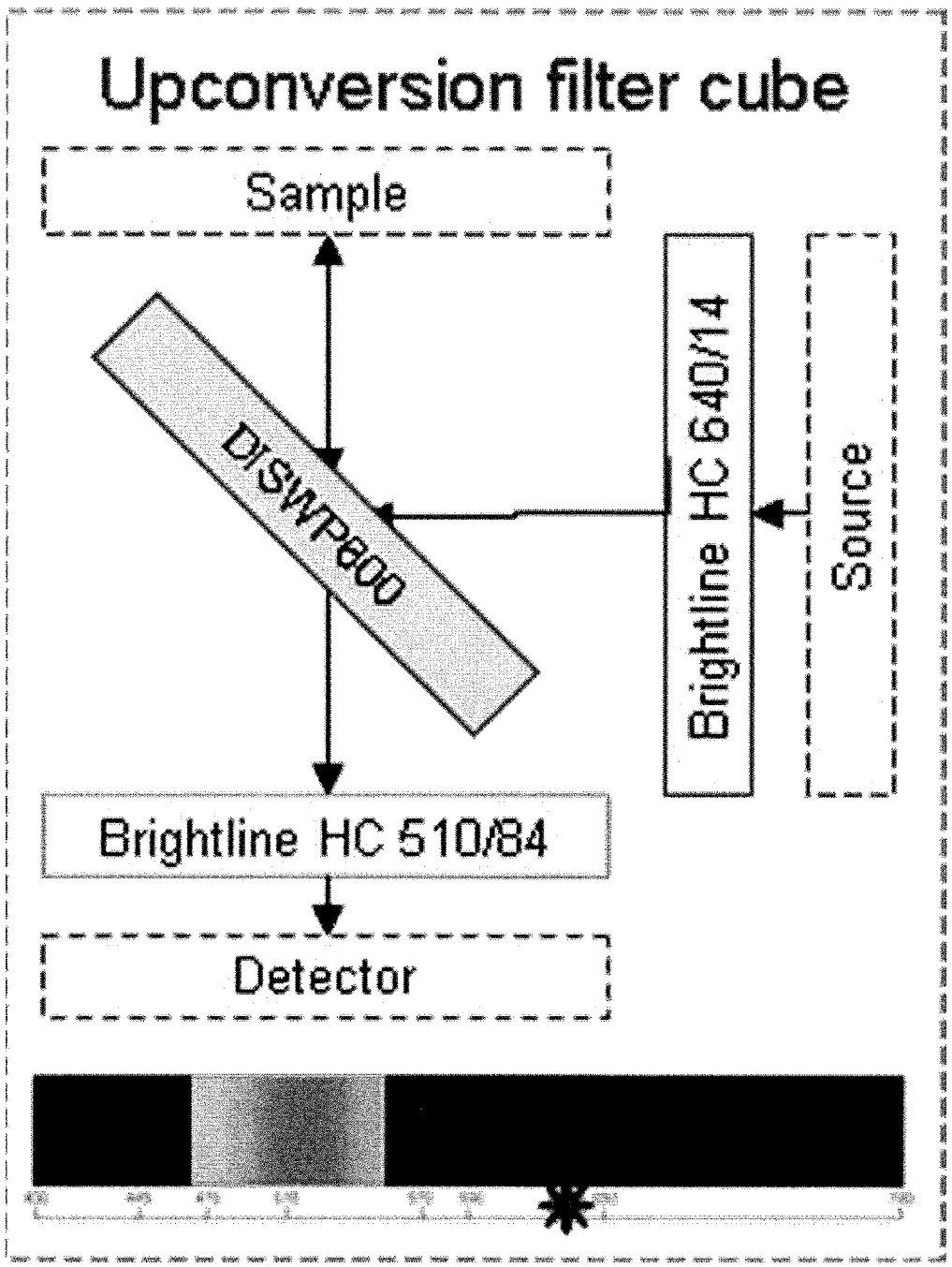

FIG. 9 shows the band filter cubes used for photon up-conversion imaging: Excitation was achieved with a band filter centered at 640 nm with 14 nm transmission band. The up-conversion emission is detected through a band filter centered at 520 nm with 84 nm transmission band.

Figure 10:
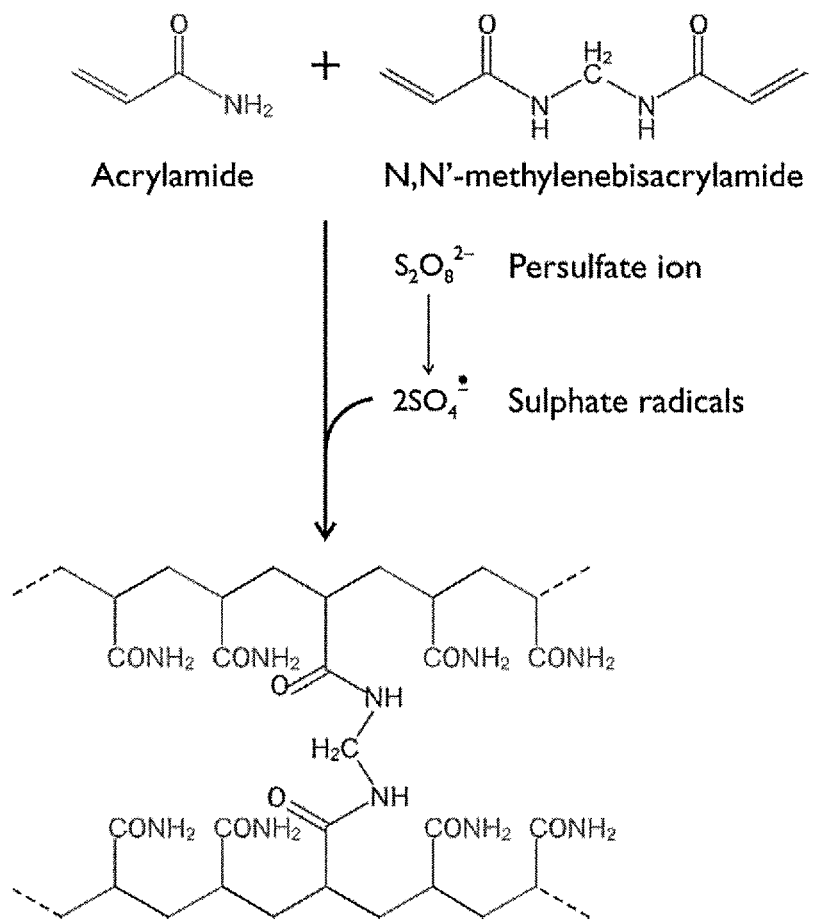

FIG. 10 shows an a polymerization process which results in polyacrylamide gel formation which gel is further for use as a gel matrix in a sensor according to the present disclosure and its formation.

Figure 11:
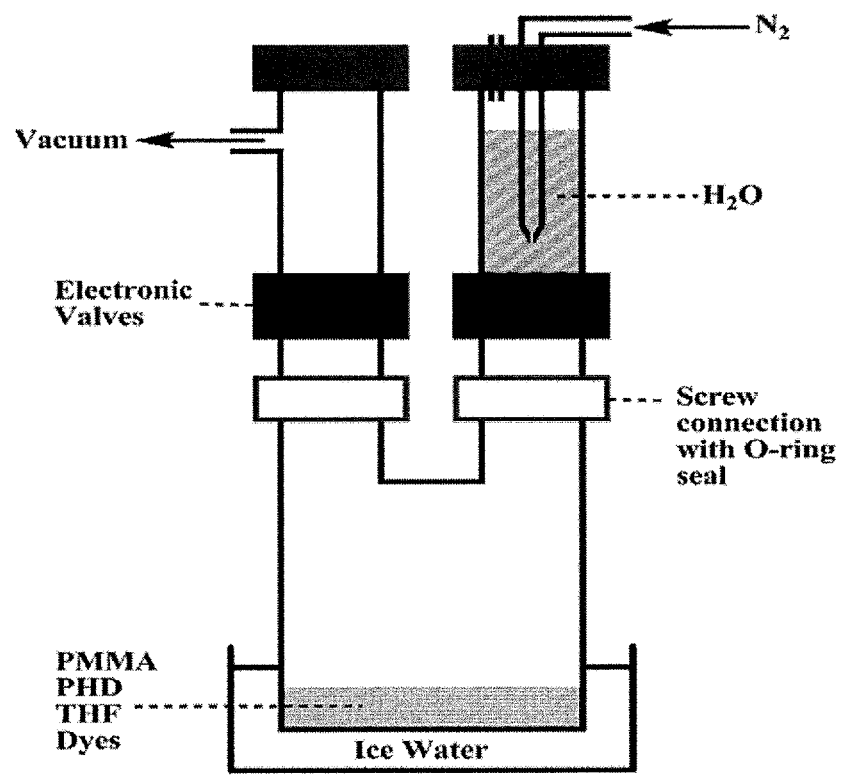

FIG. 11 shows an example of a nanoparticle fabrication chamber with valves.

Figure 12:
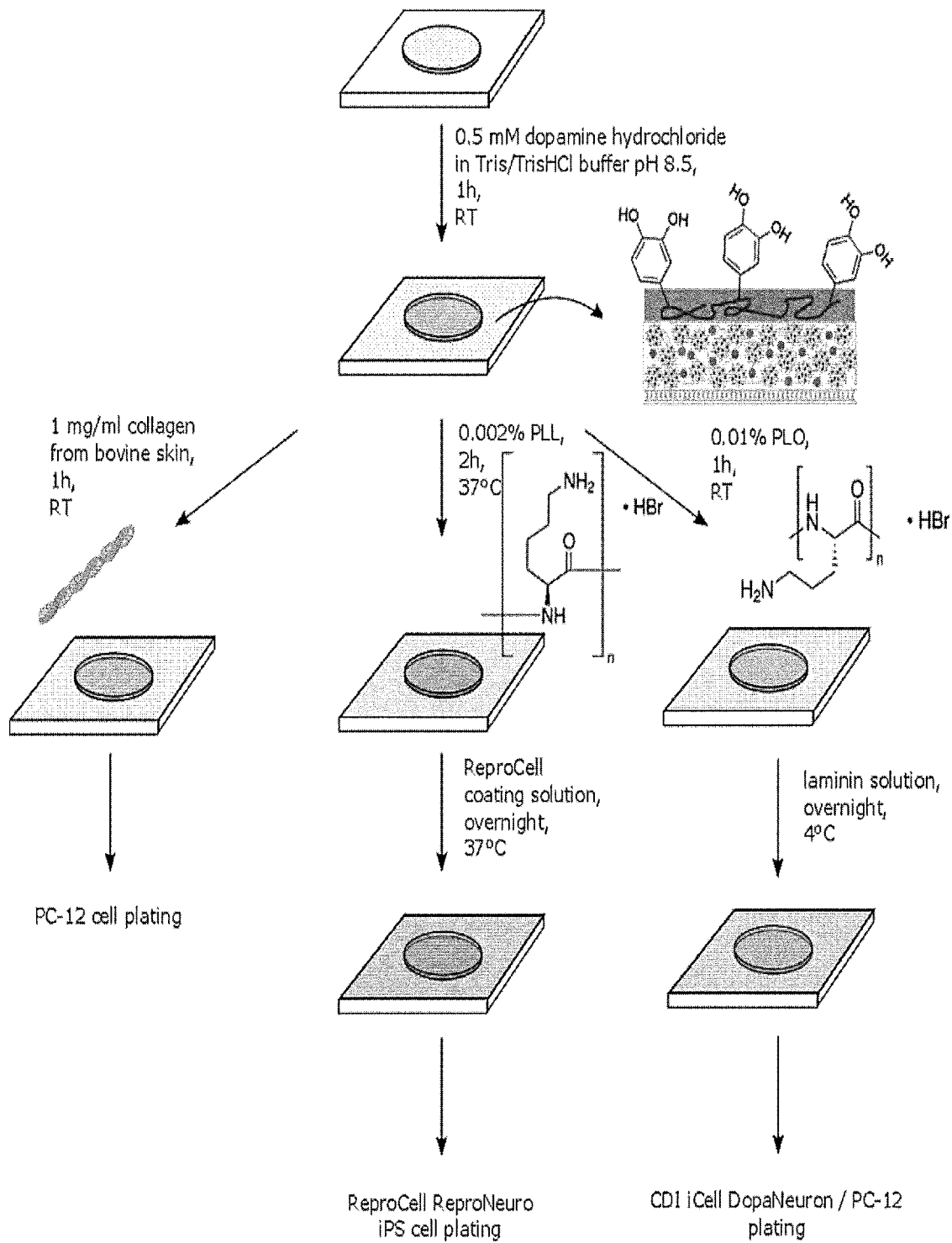

FIG. 12 shows a scheme of functionalization steps for different cell types with coating steps and conditions for the culture of different cell types.

DETAILED DESCRIPTION OF THE EMBODIMENTS

The following embodiments can, wherever this does not lead to logical contradictions, be combined with each other without restrictions. Thus, the present disclosure shall encompass, even where not explicitly spelled out in the following, any feasible combination of the embodiments described below.

As discussed above, the present disclosure provides a sensor for the detection of an analyte, said sensor including a biocompatible sensing layer including
  a matrix, wherein said matrix is a polymer matrix or polymer gel matrix, and
  organic nanoparticles embedded in said matrix, wherein said organic nanoparticles are capable of emitting light, particularly by photon up-conversion emission in the presence of said analyte, but not in the absence of said analyte, wherein said sensor optionally further includes plasmonic metal nanoparticles.

In one embodiment, said analyte is a biomolecule, more particularly a biomolecule secreted by a cultured cell. In one embodiment, said cultured cell is grown in adherent cell culture. In one embodiment, said analyte is selected from the group consisting of neurotransmitters, antioxidants (and some vitamins), reactive oxygen species and hormones.

In one embodiment, said matrix is an organic matrix. In one embodiment, said polymer matrix is a solid or more particularly a polymer gel matrix. As the skilled person will appreciate, said matrix is chemically inert with respect to and the surroundings/milieu in which said sensor is used and, particularly, also with respect to the other components of said sensor. As the skilled person will appreciate, said matrix is biocompatible and even more particularly cell compatible. Moreover, as the skilled person will appreciate, the matrix is optically inert (i.e. it does not affect the light used to irradiate the sensor in order to cause the organic nanoparticles to emit light by photon up-conversion emission in the presence of said analyte or the fluorescence of the organic nanoparticles). In one embodiment, said matrix is transparent in the range of from 450 to 750 nm.

As the skilled person will appreciate, the components of the layer in particular said matrix, said sensing layer, and said cell adherence layer, if present, must be such that the analyte is able to penetrate through them to get in contact with the nanoparticles.

As the skilled person will also appreciate, the sensing layer (and the complete sensor) must be stable in the environment that the sensor is used in. For example, if biomolecules secreted by cultured cells are to be detected, the sensor must be stable in the culture medium used for culturing said cultured cells. The sensing layer or "emissive sensing layer" (ESL) in accordance with the present disclosure may form part of a sensor. A "sensor", as used herein, refers to an arrangement of an "emissive sensing layer" on a substrate. Such sensor may include one or several additional layers, as necessary, adding functionality e.g. selected from cell adhesion layers, coating layers, enhancement layers for enhancing the intensity of the light emitted from the emissive layer, attachment layers etc.

In one embodiment, said polymer matrix is composed of a material selected from the group consisting of polyacrylamide (PAA), polyornithine, bovine serum albumin (BSA), collagen (fish, chicken, bovine, porcine), gelatin, chitosan, poly-1-lysine, laminin, gel-forming peptides, hydromatrix peptides or combinations thereof. In one embodiment, said polymer matrix is composed of collagen and/or polyornithine.

In one embodiment, said gel matrix is composed of a material selected from the group consisting of polyacrylamide.

In one embodiment, said matrix is configured such that said analyte can enter into said sensing layer (particularly by diffusion, directed flow, pressure differential or osmosis) and get into contact with said organic nanoparticles distributed within said sensing layer.

In one embodiment, said matrix has pores with a diameter below 1 µm. In one embodiment, said matrix has pores with a diameter of at least 1 nm.

In one embodiment, said organic nanoparticles have a diameter in the range of from 10 to 750 nm, particularly in the range of from 30 to 500 nm, more particularly in the range of from 50 to 300 nm, even more particularly in the range of from 50 to 100 nm.

In one embodiment, said organic nanoparticles have a surface potential value in the range of from −50 mV to −90 mV, particularly in the range of from −50 mV to −70 mV.

In one embodiment, said organic nanoparticles include a light emitter and a sensitizer. In one embodiment, said light emitter and/or said sensitizer are distributed homogeneously within said organic nanoparticles.

In one embodiment, said sensitizer is capable of absorbing light at a first wavelength region $w \leq \lambda_1 \leq x$ ("excitation wavelength for photon up-conversion"), and said light emitter is capable of emitting light at a second wavelength region $y \leq \lambda_2 \leq z$ ("emission wavelength for photon up-conversion"), wherein $\lambda_2 < \lambda_1$, and wherein, upon absorption of light by said sensitizer at said first wavelength region $w \leq \lambda_1 \leq x$, said light emitter emits light at said second wavelength region $y \leq \lambda_2 \leq z$.

In one embodiment, said light emitted by said light emitter at said second wavelength region $\lambda_2$ is due to an up-conversion process based on triplet-triplet annihilation which up-conversion process occurs upon absorption of light by said sensitizer at said first wavelength region $\lambda_1$. (Upon subsequent intersystem crossing in the sensitizer molecule, an excited triplet state is reached. The sensitizer triplet excitation is transferred to the emitter triplet state, followed by annihilation of two excited triplet states of the emitter. The light emitted by said light emitter at said second wavelength region $\lambda_2$ is due to the triplet-triplet annihilation between two emitter excited triplets resulting in population of one of the emitter's singlet states which relaxes emitting light with wavelength $\lambda_2$.

In a preferred embodiment, said second wavelength region $\lambda_2$ is in the range 420-620 nm and said first wavelength region $\lambda_1$ is in the range 530-860 nm.

In one embodiment, said sensitizer is an organic dye or molecule having a populated triplet or mixed triplet-singlet state.

In one embodiment, said light emitter is an organic molecule. In one embodiment, said sensitizer is an organic molecule.

In one embodiment said light emitter is an organic dye molecule (chromophore or fluorophore).

In one embodiment, said light emitter consists of one molecule (i.e. only one molecular species). In one embodiment, said light emitter consists of a combination of more than one, particularly two, molecules. In one embodiment, said sensitizer consists of one molecule. In one embodiment, said sensitizer consists of a combination of more than one, particularly two, molecules.

In one embodiment, said sensitizer and said light emitter are separate entities (i.e. sensitizer and light emitter are not covalently linked to each other and do not form part of the same molecule).

In one embodiment, the light emitted by said light emitter has a wavelength in the range of from 360 to 750 nm, particularly in the range of from 420 to 640 nm.

In one embodiment, said sensitizer absorb light at a wavelength in the range of from 450 to 1600 nm, particularly in the range of from 530 to 860 nm. Most particularly in the range of from 620 to 750 nm.

In one embodiment, said light emitter is capable of emitting light by luminescence, particularly by fluorescence. Particularly the fluorescence is with a high quantum yield when the emitter is in the nanoparticle, such a "high quantum yield" typically being >60%.

In one embodiment, said light emitter is a fluorescent chromophore.

In one embodiment, said light emitter in combination with said sensitizer is capable of, upon irradiation with light of appropriate wavelength (the excitation wavelength for photon up-conversion), photon up-conversion emission (i.e. emission of light generated by photon up-conversion).

In one embodiment, the energy levels of the triplet state of said light emitter and of the triplet state of said sensitizer are such that they allow for efficient triplet-triplet excitation transfer from the light sensitizer to the light emitter.

In one embodiment, said light emitter is selected from the group consisting of anthracenes, perylenes, preylene derivatives such as perylene monoimides, perylene diimides. In one embodiment, said light emitter is a perylene, or a perylene derivative, such as a functionalized perylene, a substituted perylene (see structures further below) or perylene monoimide or perylene diimide. A "substituted perylene" or a "perylene derivative" as used herein, refers to a structure having a perylene core. A "perylene derivative" may be a perylene that is substituted with appropriate substituents.

In one embodiment, said at least one light emitter has the structure represented by Formula (I) or (II) or includes a molecule having the structure represented by Formula (I) or (II):

Formula (I)

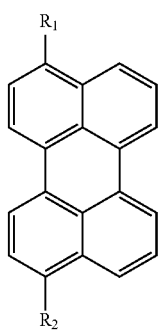

Formula (II)

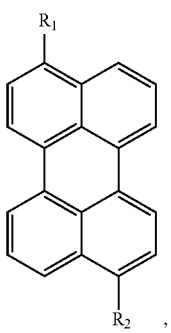

wherein $R_1$ and $R_2$ are independently selected from the group consisting of hydrogen and a moiety with the structure represented by Formula (III), wherein at least one of $R_1$ and $R_2$ is a moiety with the structure represented by Formula (III):

Formula (III)

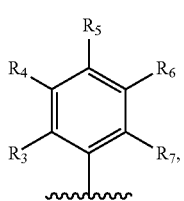

wherein $R_3$, $R_4$, $R_5$, $R_6$ and $R_7$ are independently selected from the group consisting of H, F, and tri-fluoro-methyl (—$CF_3$),
wherein at least one of $R_3$, $R_4$, $R_5$, $R_6$ and $R_7$ is F or tri-fluoro-methyl (—$CF_3$).

In one embodiment, $R_1$ and/or $R_2$ is the moiety represented by Formula (IV):

Formula (IV)

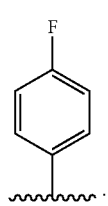

In one embodiment, $R_1$ and/or $R_2$ is the moiety represented by Formula (V):

Formula (V)

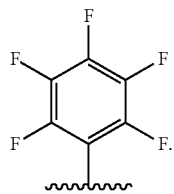

In one embodiment, $R_1$ and/or $R_2$ is the moiety represented by Formula (VI):

Formula (VI)

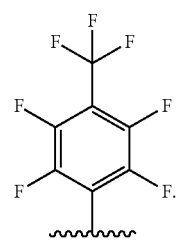

In one embodiment, said at least one light emitter has the structure represented by Formula (VII) or includes a molecule having the structure represented by Formula (VII):

Formula (VII)

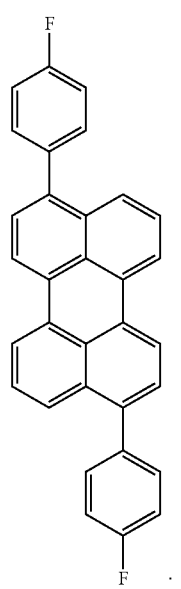

In another embodiment, said at least one light emitter has the structure represented by Formula (VIII) or includes a molecule having the structure represented by Formula (VIII):

Formula (VIII)

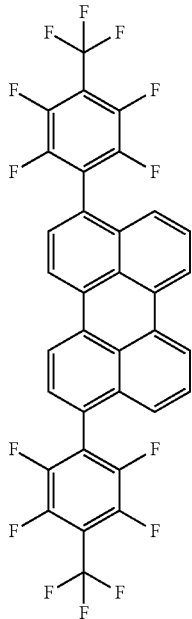

In another embodiment, said at least one light emitter has the structure represented by Formula (IX) or includes a molecule having the structure represented by Formula (IX):

Formula (IX)

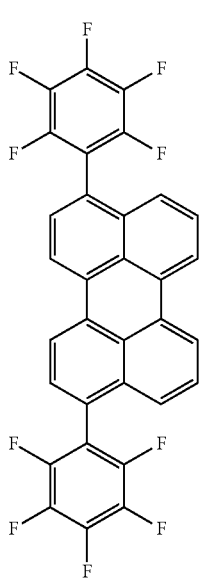

In one embodiment, said at least one light emitter has the structure represented by Formula (X) or includes a molecule having the structure represented by Formula (X):

Formula (X)

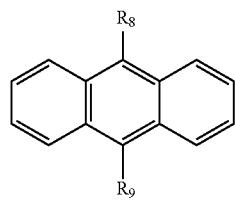

wherein $R_8$ and $R_9$ are independently selected from the group consisting of hydrogen and a moiety with the structure represented by Formula (XI), wherein at least one of $R_8$ and $R_9$ is a moiety with the structure represented by Formula (XI):

Formula (XI)

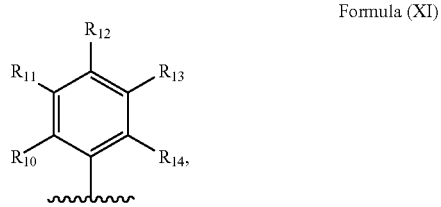

wherein $R_{10}$, $R_{11}$, $R_{12}$, $R_{13}$ and $R_{14}$ are independently selected from the group consisting of H, F, and tri-fluoro-methyl (—$CF_3$), wherein at least one of $R_{10}$, $R_{11}$, $R_{12}$, $R_{13}$ and $R_{14}$ is F or tri-fluoro-methyl (—$CF_3$).

In one embodiment, $R_8$ and/or $R_9$ is the moiety represented by Formula (XII):

Formula (XII)

In one embodiment, $R_8$ and/or $R_9$ is the moiety represented by Formula (XIII):

Formula (XIII)

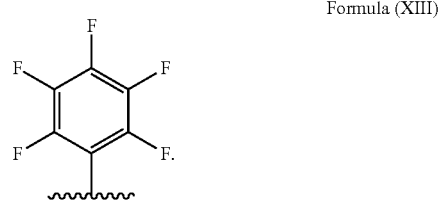 [SMILES: *c1c(F)c(F)c(F)c(F)c1F]

In one embodiment, $R_8$ and/or $R_9$ is the moiety represented by Formula (XIV):

Formula (XIV)

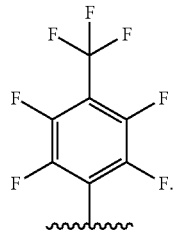

In one embodiment, $R_8$ and/or $R_9$ is the moiety represented by Formula (XV):

Formula (XV)

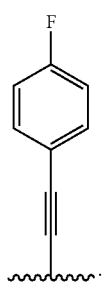

In one embodiment, $R_8$ and/or $R_9$ is the moiety represented by Formula (XVI):

Formula (XVI)

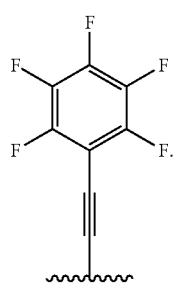

In one embodiment, said at least one light emitter has the structure represented by Formula (XVII) or includes a molecule having the structure represented by Formula (XVII):

Formula (XVII)

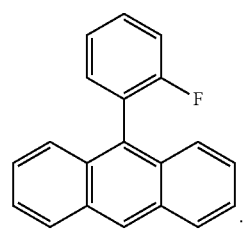

In another embodiment, said at least one light emitter has the structure represented by Formula (XVIII) or includes a molecule having the structure represented by Formula (XVIII):

Formula (XVIII)

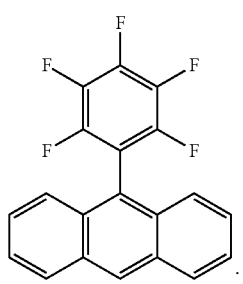

In another embodiment, said at least one light emitter has the structure represented by Formula (XIX) or includes a molecule having the structure represented by Formula (XIX):

Formula (XIX)

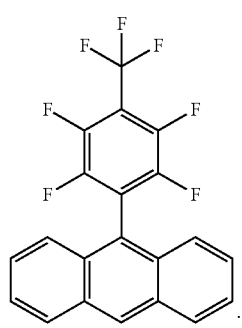

In another embodiment, said at least one light emitter has the structure represented by Formula (XX) or includes a molecule having the structure represented by Formula (XX):

Formula (XX)

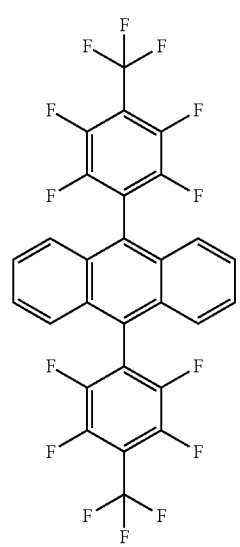

In preferred embodiment, said at least one light emitter has the structure represented by Formula (XXI) or includes a molecule having the structure represented by Formula (XXI):

Formula (XXI)

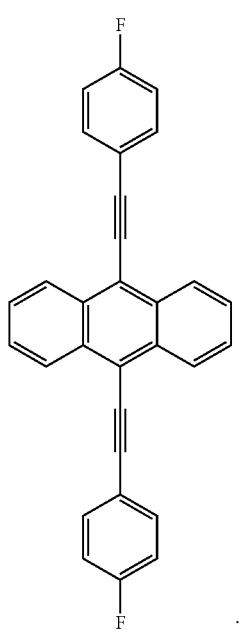

In another embodiment, said at least one light emitter has the structure represented by Formula (XXII) or includes a molecule having the structure represented by Formula (XXII):

Formula (XXII)

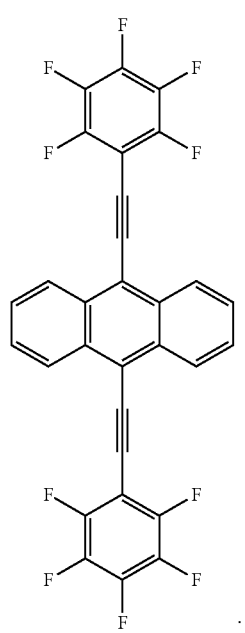

In one embodiment, said at least one light emitter has a structure represented by one of the following structures or includes a molecule having a structure represented by one of the following structures:

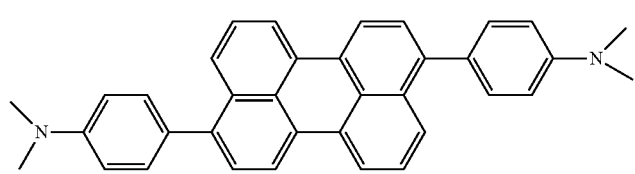

-continued

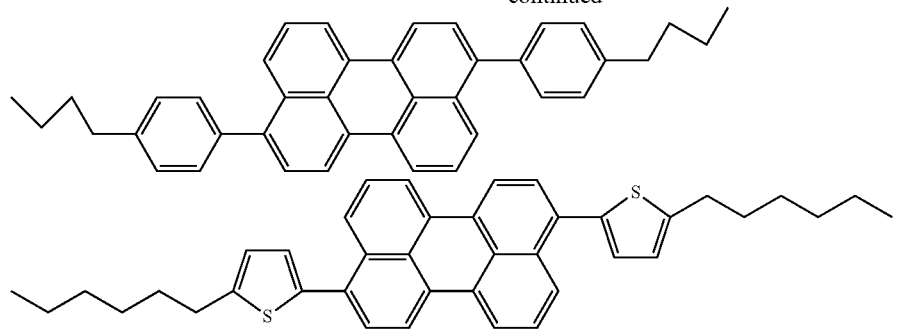

In one embodiment, said at least one light emitter has the structure represented by Formula (XXIII), (XXIV) or (XXV) or includes a molecule having the structure represented by Formula (XXIII), (XXIV) or (XXV):

Formula (XXIII)

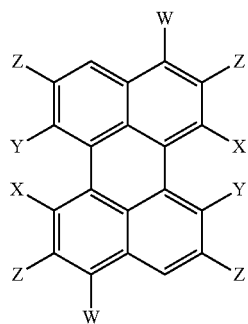

Formula (XXIV)

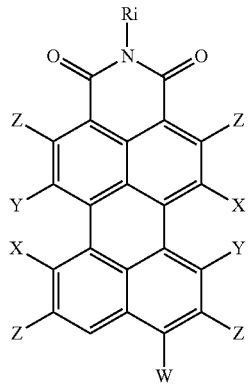

Formula (XXV)

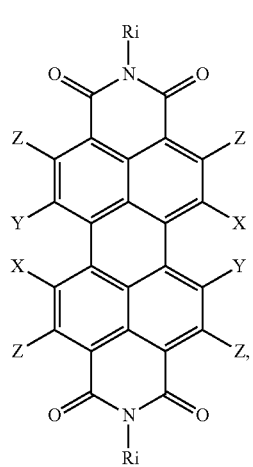

wherein W in formulae XXIII-XXV is selected from one of the following groups:

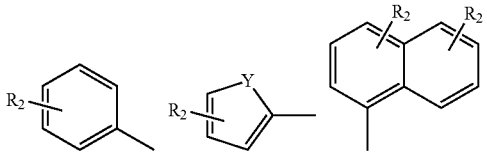

wherein Y, as used in the formulae of W, is selected from the group consisting of $CH_2$, S, O, Se and $N-R_2$, and wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a halogenated alkyl group, a heteroaryl group, a fluorenyl group, an amino group, a nitro group, an OH group, an SH group, and a group $-O-R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a halogenated alkyl group, a heteroaryl group and a fluorenyl group, wherein, in particular, $R_2$ has not more than 6 carbon atoms, wherein X and Y in formulae XXIII-XXV are independently selected from the following

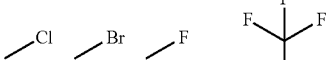

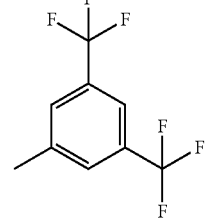

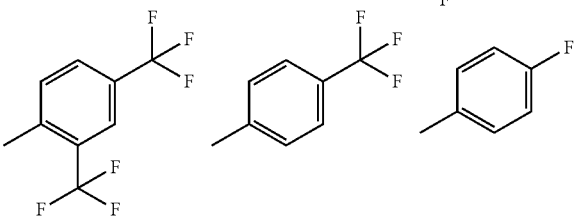

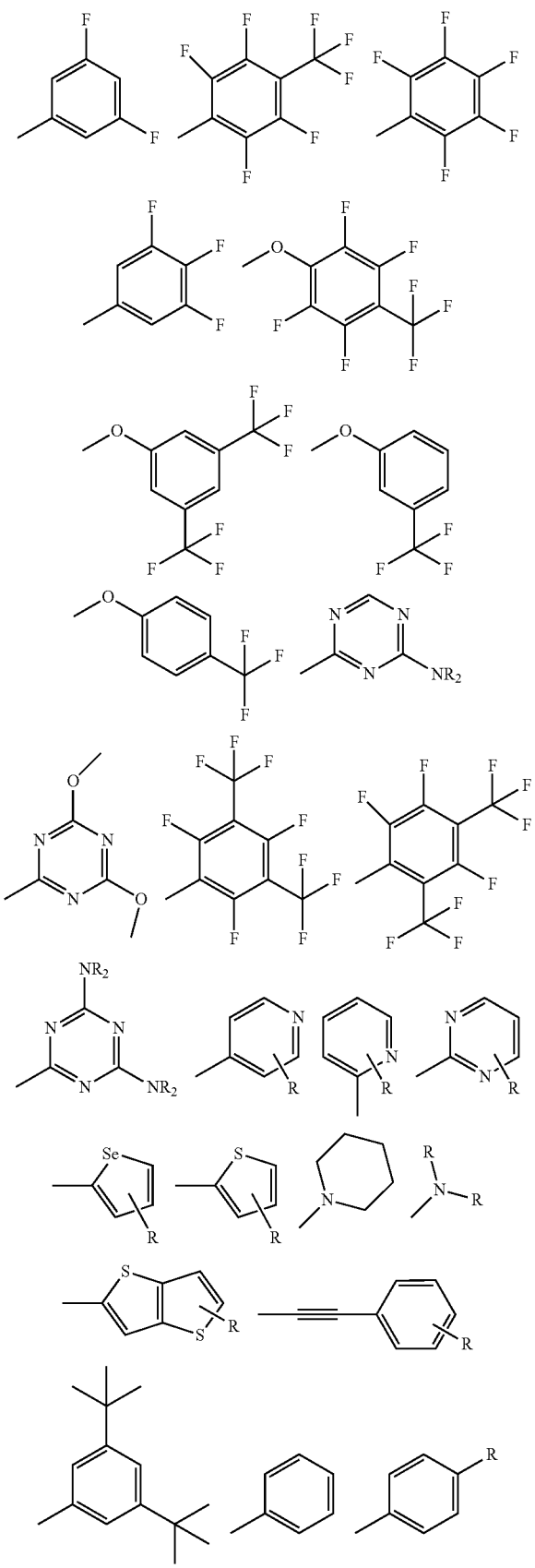

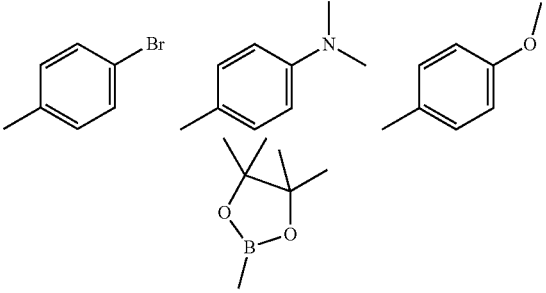

groups:

and wherein R is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a halogenated alkyl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a halogenated alkyl group, a heteroaryl group and a fluorenyl group, wherein, particularly, R has not more than 6 carbon atoms, wherein Z in formulae XXIII-XXV is selected from the following groups:

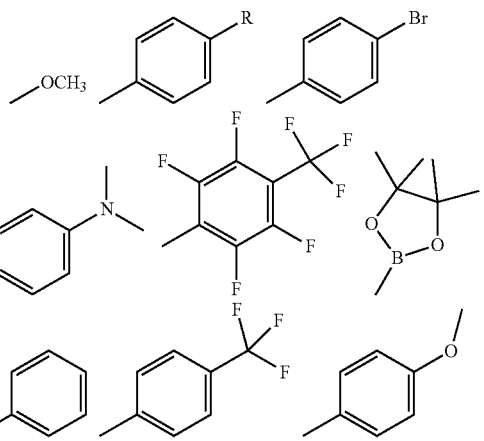

and wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a halogenated alkyl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a halogenated alkyl group, a heteroaryl group and a fluorenyl group, wherein, in particular, $R_2$ has not more than 6 carbon atoms, wherein Ri in formulae XXIII-XXV is selected from the following groups:
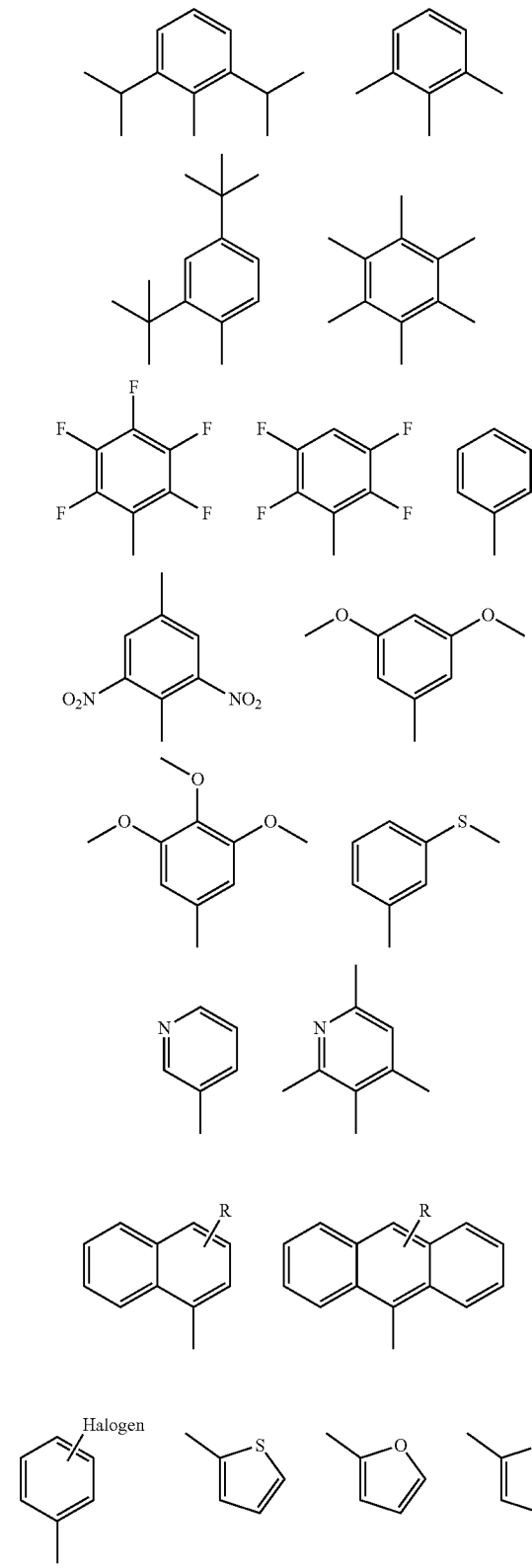
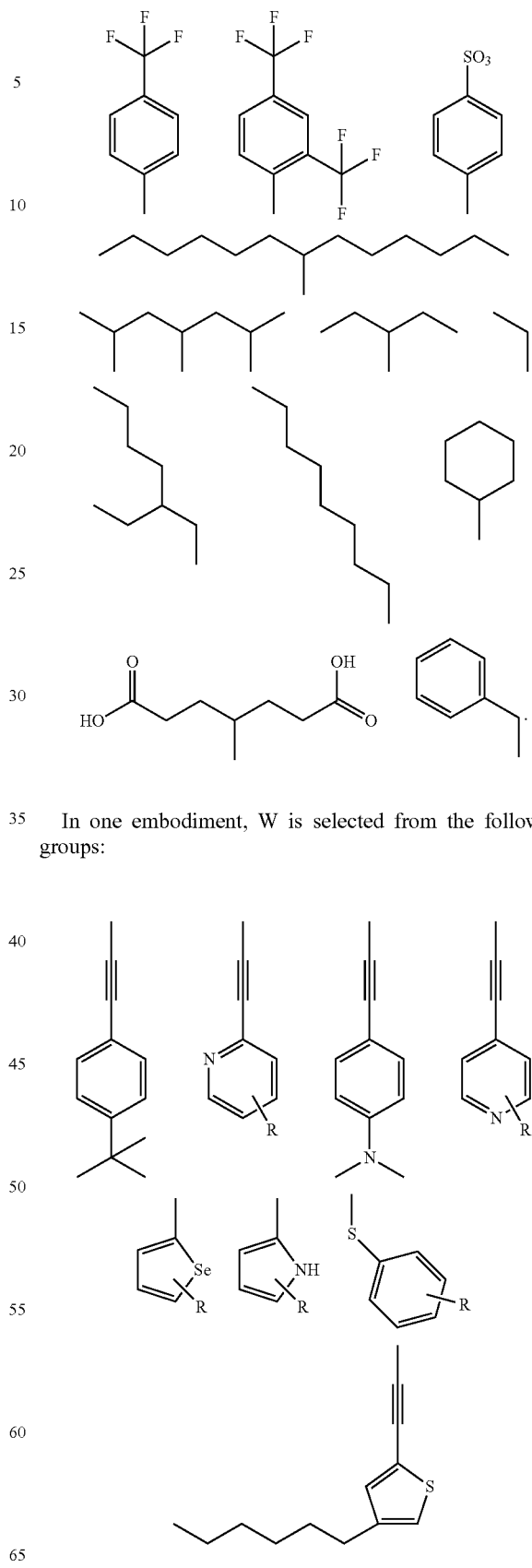
In one embodiment, W is selected from the following groups:

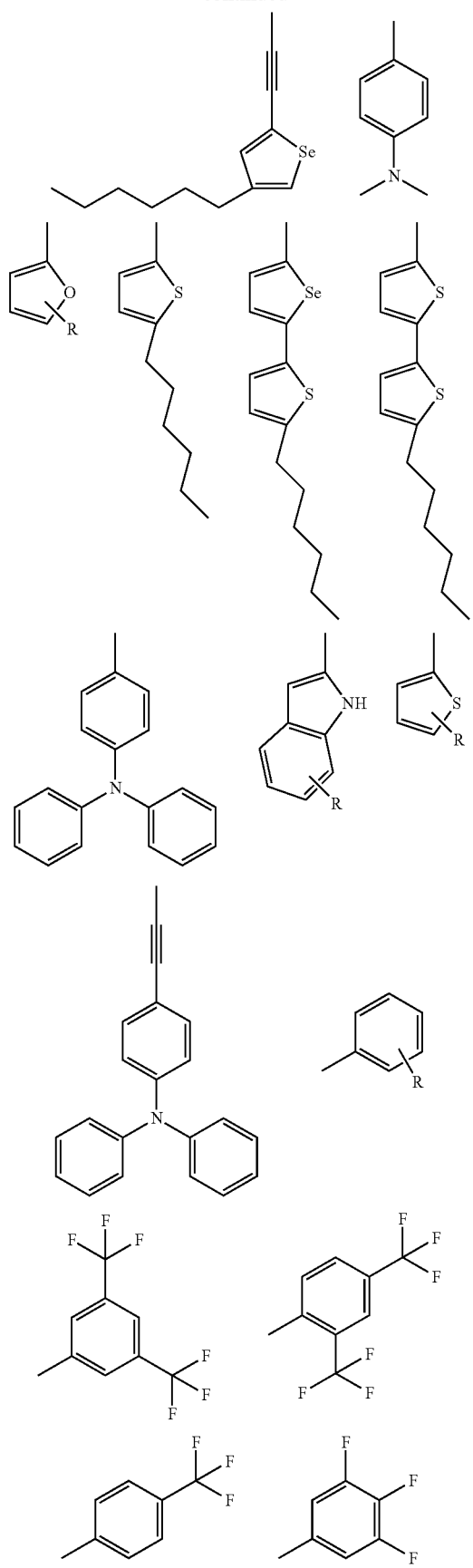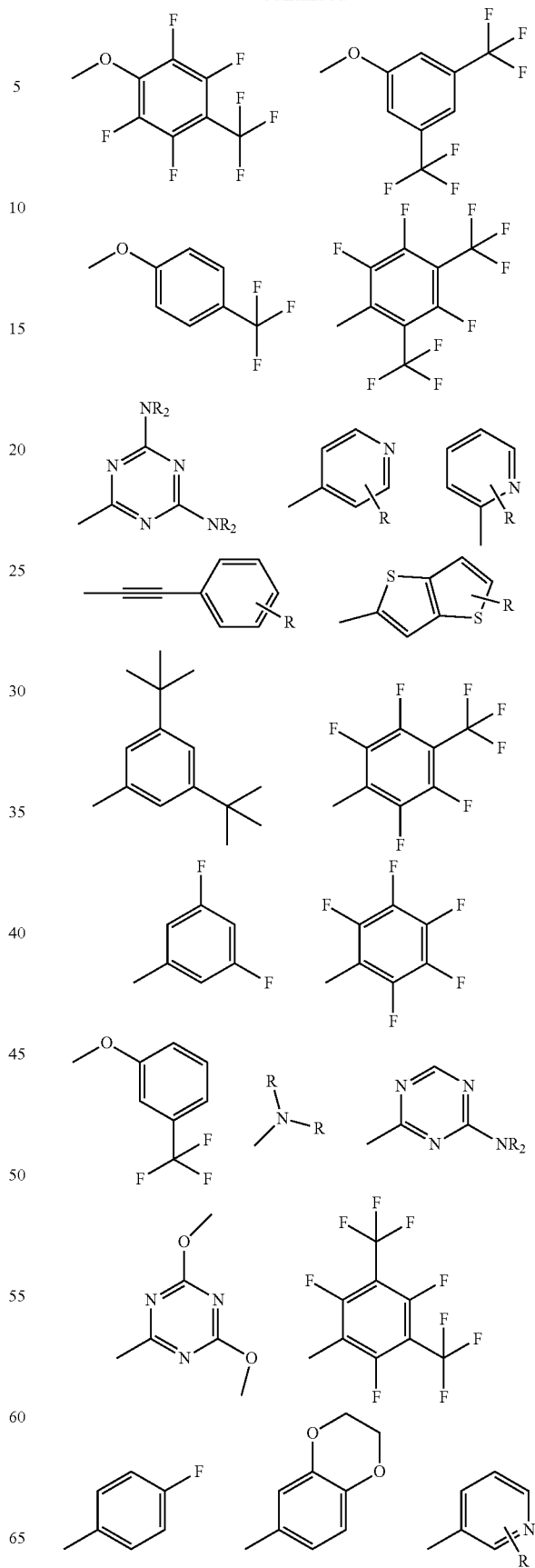

-continued

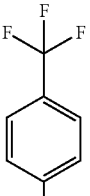

In one embodiment, said at least one light emitter has a structure selected from one of the following:

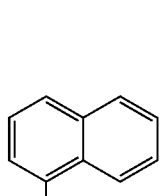

wherein R is a linear or branched alkyl group, particularly with not more than 6 carbon atoms.

In one embodiment, said at least one light emitter has the structure represented by Formula (XXVI) or includes a molecule having the structure represented by Formula (XXVI):

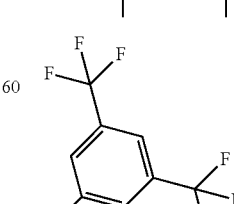

Formula (XXVI)

wherein R is selected from the following groups:

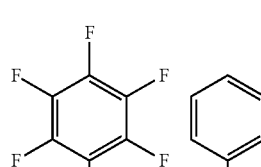

wherein Y is selected from the group consisting of $CH_2$, S, O, Se and N—$R_2$, and wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a halogenated alkyl group, a heteroaryl group, a fluorenyl group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a halogenated alkyl group, a heteroaryl group and a fluorenyl group, wherein, particularly, $R_2$ has not more than 6 carbon atoms, or wherein R is selected from the following groups:

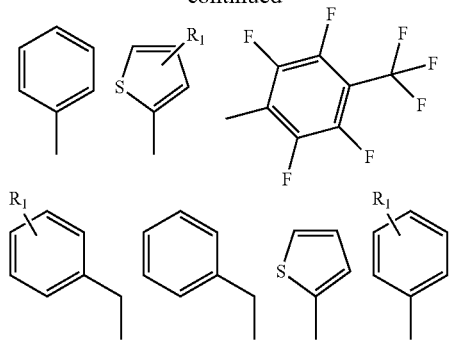

wherein $R_1$ is a linear or branched alkyl group, particularly with not more than 6 carbon atoms.

In one embodiment, said at least one light emitter has a structure selected from one of the following or includes a molecule having a structure selected from one of the following:

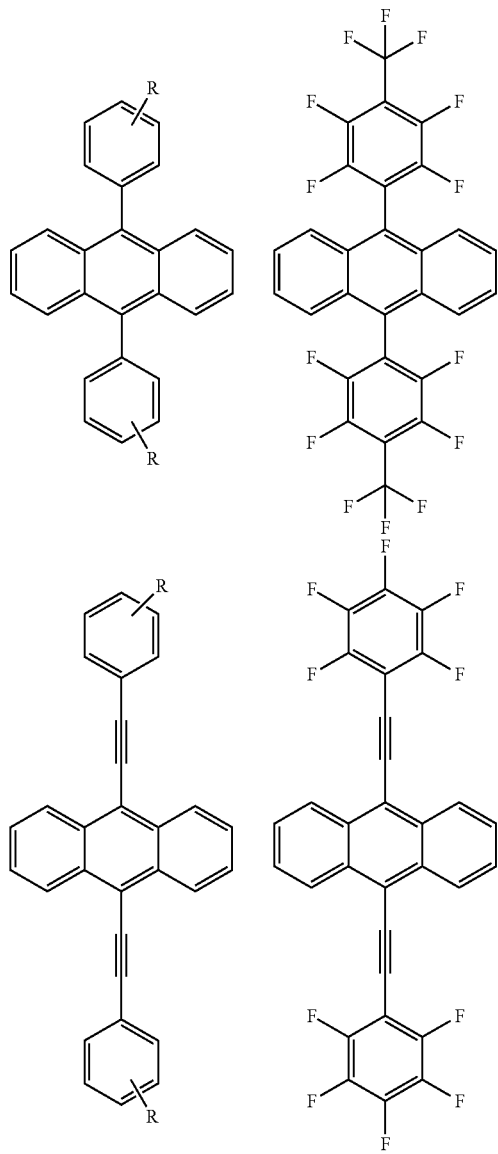

wherein R is a linear or branched alkyl group, particularly with up to 6 carbon atoms.

Said at least one sensitizer may be any dye with high intersystem crossing resulting in highly populated triplet state.

In one embodiment, said at least one sensitizer is or includes a porphyrin, particularly a benzo porphyrin or naphto porphyrins, or a phthalocyanine.

In one embodiment, said at least one sensitizer has the structure represented by Formula (XXVII) or includes a molecule having the structure represented by Formula (XXVII):

Formula (XXVII)

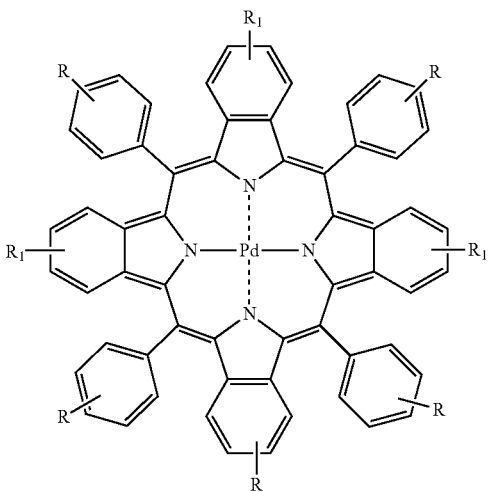

wherein $R_1$ is hydrogen, a linear or branched alkyl group, in particular with up to 6 carbon atoms, or a benzene ring, and wherein R is a linear or branched alkyl group, in particular with up to 6 carbon atoms.

In one embodiment, said at least one sensitizer has a structure represented by Formula (XXVIII), Formula (IXXX), Formula (XXX) or Formula (XXXI) or includes a molecule having a structure represented by Formula (XXVIII), Formula (IXXX), Formula (XXX) or Formula (XXXI):

Formula (XXVIII)

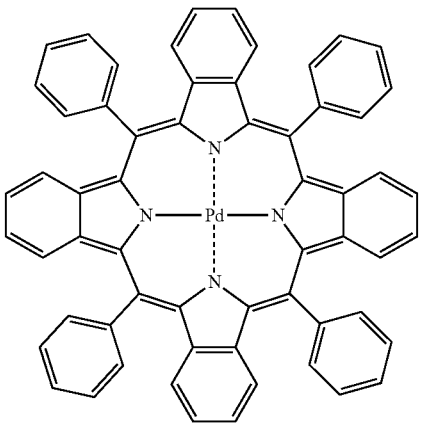

-continued

Formula (IXXX)

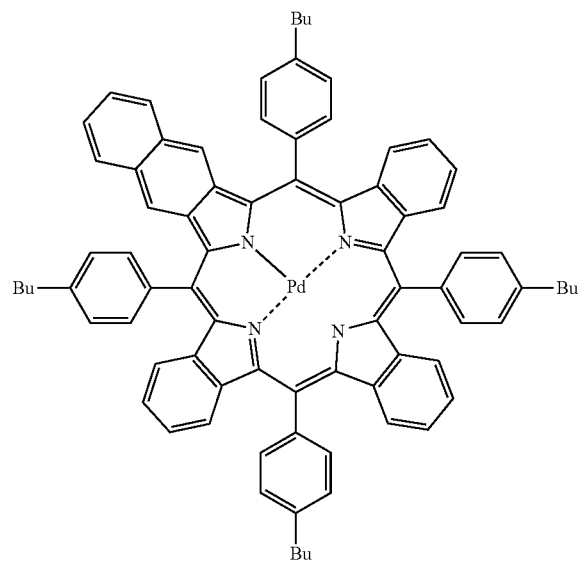

Formula (XXX)

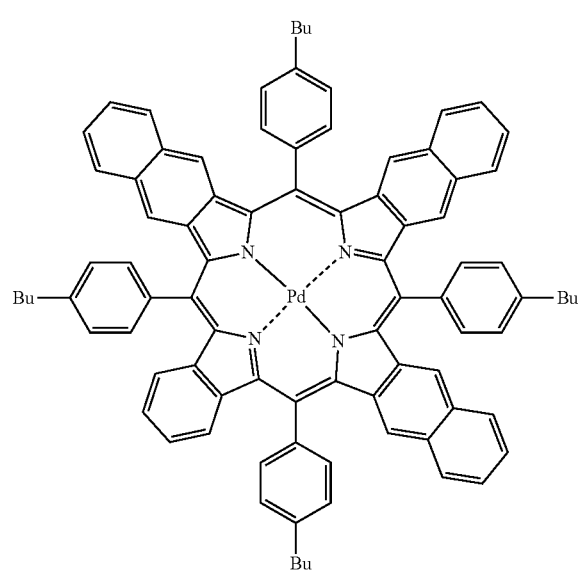

-continued

Formula (XXXI)

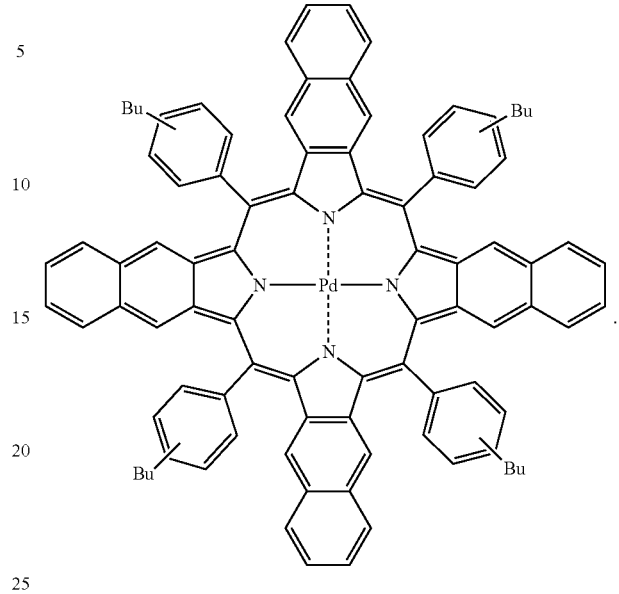

In one embodiment, said sensitizer has the structure represented by Formula (XXVIII):

Formula (XXVIII)

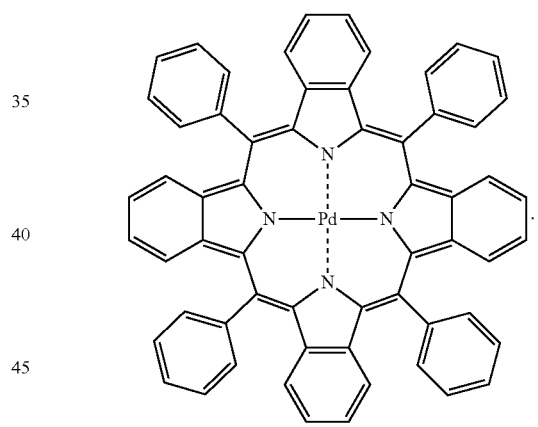

Organic nanoparticles suitable for use in said sensing layer are, for example, those described in EP 2298849

To prepare organic nanoparticles including metal nanoparticles or singlet oxygen scavengers, the procedure according to EP 2298849 is modified by inducing a mixture including said organic matrix components and surface stabilizer, emitters and plasmonic metal nanoparticles to form nanoparticles (NP), thus forming a dispersion of nanoparticles wherein said nanoparticles include a polymeric organic matrix with said light emitter(s) and, optionally, said sensitizer(s) and/or said antioxidant(s), distributed therein, and wherein said metal nanoparticles are enclosed in said polymeric organic matrix.

Alternatively, BioPhotonicsII_Nanoprobes may be used.

In one embodiment, said organic nanoparticles include a second light emitter. In one embodiment, said second light emitter is as the light emitter defined in any of the embodiments above or below.

In one embodiment, said organic nanoparticles include a second sensitizer. In one embodiment, said second sensitizer is as the sensitizer defined in any of the embodiments above or below.

In one embodiment said organic nanoparticles contain at least one antioxidant. Said is optically inactive, but is a part of the matrix and increases the brightness, and even more so, the stability of the sensitizer and emitter molecules.

Different antioxidants-singlet oxygen scavengers or other reactive oxygen species scavengers (ROS scavengers) can be used. Generally, any antioxidant, especially singlet oxygen scavenger/quencher, can be used as far as it is soluble in an organic phase. The antioxidant does not need to be soluble in water (or at best only needs to have very limited solubility in water), but it should be well soluble in THF, DMF or ethanol (or other water miscible organic solvents which are also used as solvents for the other NP components). The following exemplary antioxidants can be used but the application is not limited to these examples: ascorbic acid palmitate (6-O-Palmitoyl-L-ascorbic acid), ascorbic acid esters, caffeic acid esters, lipoic acid (all racemic forms), lauryl gallate and other galic acid esters—octyl, butyl, ethyl esters; Vitamin E ($\alpha$-Tocopherol, $\delta$- or $\gamma$-Tocopherol and tocopherol acetates)—all racemic forms; Tocotrienol-all racemic forms, resveratrol; Pyrocatechol; 3-ethylbenzophenone; Magnolol, carnosol; Vitamin A-retinol (retinoic acid), retinol palmitate, retinol acetate, retinol esters, vitamin A aldehyde (retinal), carotene s—e.g. beta-carotene I and II, carotenal, mixtures of beta-carotenes, also lycopene; Ubiquinone (Coenyme Q-10), bromadiolon, vitamin K2, vitamin K3, flavones/flavonols (catehins, etc.), eugenol and others. Designed combinations thereof—e.g. ascorbic acid palmitate with lipoic acid—can also be used.

In one embodiment, each of said organic nanoparticles includes 1 to 4 metal nanoparticles.

In one embodiment, said metal nanoparticles are distributed within said matrix of said sensing layer and/or said sensor includes an enhancement layer in which said metal nanoparticles are distributed and/or said metal nanoparticles are distributed within said organic nanoparticles. In one embodiment, said enhancement layer is a continuous layer composed of said metal nanoparticles. In another embodiment, said enhancement layer is a thin layer of metal, having been deposited on said substrate, e.g. by vapor deposition.

In one embodiment, said enhancement layer has a thickness in the range of from 10 to 100 nm, particularly in the range of from 20 to 60 nm.

In one embodiment, said sensor includes no other metal nanoparticles beyond the metal nanoparticles that are distributed within said matrix of the sensing layer. In one embodiment, said sensor includes no other metal nanoparticles beyond the metal nanoparticles that are present within said enhancement layer. In one embodiment, said sensor includes no other metal nanoparticles beyond the metal nanoparticles distributed within said organic nanoparticles. In a further embodiment, said sensor includes no other metal nanoparticles beyond the metal nanoparticles distributed within said organic nanoparticles and the metal nanoparticles distributed within the matrix of the sensing layer.

In one embodiment, said metal nanoparticles are not in contact with each other (i.e. all metal particles included within the sensor are individual particles that do not touch each other directly). This way, it is ensured that the plasmon properties of the metal particles are preserved in order to allow for plasmon enhancement.

As the skilled person will appreciate, for the metal nanoparticles any metal particles with plasmon may be used, e.g. metal nanoparticles. Typically, such metal nanoparticles have a plasmon and are herein also sometimes referred to as "plasmonic" metal nanoparticles. Without wishing to be bound by any theory, the present inventors believe that the electron density of such plasmonic metal nanoparticles can couple with radiation. i.e. Plasmonic nanoparticles are used as particles whose electron density can couple with electromagnetic radiation of wavelengths that are far larger than the particle itself.

In one embodiment, said metal (plasmonic) nanoparticles have a diameter in the range of from 1 to 100 nm, particularly in the range of from 4 to 80 nm, more particularly in the range of from 10 to 60 nm, more particularly in the range of from 10 to 50 nm. In one embodiment, such metal nanoparticle has an average diameter in the range of from 1 nm to 50 nm, particularly 1 nm to 30 nm, more particularly 1 nm to 20 nm. In one embodiment, it has an average diameter of from 10 nm to 50 nm, particularly 10 nm to 30 nm. In another embodiment, such metal nanoparticle has an average diameter of from 1 nm to 40 nm, particularly 5 nm to 30 nm. Typically, such metal nanoparticle having an average diameter of from 1 nm to 100 nm or an average diameter of any subrange therein is a plasmonic nanoparticle. If the present application indicates that a diameter, e.g. of metal nanoparticles, is in a certain range, this means that the average diameter of said metal nanoparticles falls in that certain range. In one embodiment, the diameter of individual metal nanoparticles varies by not more than 30%, particularly by not more than 20%, more particularly by not more than 10%.

In one embodiment, said nanoparticle (NP) includes a single metal nanoparticle. In one embodiment, said single metal nanoparticle forms the core of said nanoparticle (NP), wherein said polymeric organic matrix forms a shell around said core.

The metal particles may be composed of any metal or materials with plasmonic properties—and in this way are plasmonic nanoparticles (e.g. nanospheres, nanoshells, nanocubes, nanorods and nanoplates). In one embodiment, said at least one plasmonic nanoparticle consists of a material selected from the group consisting of Ag, Au and Co, Al, Cu, metal alloys/layered structures like Ag/Au or of nitrides of transition metals (TiN, ZrN). In one embodiment, said at least one plasmonic (metal) nanoparticle is composed of Ag.

In one embodiment, said metal particles do not include or consist of a rare-earth metal, rare-earth metal ions or compounds/material formed from a rare-earth element. In one embodiment, said metal particles consist of only one element (i.e. they are composed of a pure chemical substance consisting of a single type of atom). In another embodiment they can be alloy NPs (i.e. Ag/Au, etc)

In one embodiment, said sensor does not include rare-earth metal, rare-earth metal ions or compounds/material formed from a rare-earth element.

In one embodiment, said metal nanoparticles are massive particles (i.e. the interior of the metal particles is completely filled by the metal which said metal nanoparticles are made of, and the metal nanoparticles do not enclose any other material than said metal nor do they enclose any void space).

In one embodiment, said metal nanoparticles have a coating consisting of $SiO_2$.

In one embodiment, said sensing layer further includes at least one radical scavenger, e.g. reactive oxygen scavenger (ROS), in particular a singlet oxygen scavenger, e.g. an antioxidant. In one embodiment, said at least one antioxidant is an organic antioxidant. In one embodiment, the sensing layer includes only one antioxidant (i.e. only one kind of antioxidant). In one embodiment, said at least one antioxidant is distributed homogeneously within said sensing layer. In one embodiment, said at least one antioxidant is distributed homogeneously within said matrix of said sensing layer. In one embodiment, said at least one antioxidant is not present within said organic nanoparticles. In one embodiment, said at least one antioxidant is a water soluble antioxidant. In one embodiment, said water soluble antioxidant is selected from the group consisting of vitamin C, gallic acid, a vitamin B and caffeic acid. In one embodiment, said at least one antioxidant is distributed within said organic nanoparticles. Different antioxidants-singlet oxygen scavengers or other reactive oxygen species scavengers (ROS scavengers) can be used. Generally, any antioxidant, especially singlet oxygen scavenger/quencher, can be used as far as it is soluble in an organic phase. The antioxidant does not need to be soluble in water (or at best only needs to have very limited solubility in water), but it should be well soluble in THF, DMF or ethanol (or other water miscible organic solvents which are also used as solvents for the other NP components). The following exemplary antioxidants can be used but the application is not limited to these examples: ascorbic acid palmitate (6-O-Palmitoyl-L-ascorbic acid), ascorbic acid esters, caffeic acid esters, lipoic acid (all racemic forms), lauryl gallate and other galic acid esters-octyl, butyl, ethyl esters; Vitamin E (α-Tocopherol, δ- or γ-Tocopherol and tocopherol acetates)—all racemic forms; Tocotrienol-all racemic forms, resveratrol; Pyrocatechol; 3-ethylbenzophenone; Magnolol, carnosol; Vitamin A-retinol (retinoic acid), retinol palmitate, retinol acetate, retinol esters, vitamin A aldehyde (retinal), carotene s—e.g. beta-carotene I and II, carotenal, mixtures of beta-carotenes, also lycopene; Ubiquinone (Coenyme Q-10), bromadiolon, vitamin K2, vitamin K3, flavones/flavonols (catehins, etc.), eugenol and others. Designed combinations thereof—e.g. ascorbic acid palmitate with lipoic acid—can also be used.

In one embodiment, said at least one antioxidant is not a component of said matrix of said sensing layer. In one embodiment, said at least one antioxidant is soluble in an organic, water-miscible solvent, more particularly in THF or DMF. In one embodiment, said at least one antioxidant is selected from the group consisting of lipoic acid, vitamin E, carotenoids and vitamin C ester.

In one embodiment, said organic nanoparticles include functional groups at their surface that allow to covalently couple further molecules to the organic nanoparticles. In one embodiment, said functional groups are selected from the group consisting of —COOH (carboxylate), —NH$_2$, —SH (thiol), —NHS, alkynyl, —N$_3$, aldehyde, ketone and biotin group, more particularly said functional groups are —COOH or —NH$_2$.

In one embodiment, said organic nanoparticles include molecules or chemical groups attached to their surface that are capable of specifically binding to said analyte molecule or that have an enzymatic activity that allows to detect said analyte molecule. In one embodiment, said molecules attached to the surface of the organic nanoparticles are protein molecules. In one embodiment, said molecules attached to the surface of the organic nanoparticles are antibody molecules, affibodies, aptamers or enzyme molecules.

In one embodiment, said sensor further includes an attachment layer by which the sensor can be immobilized on a substrate, particularly by covalent and/or electrostatic forces. Suitable substrates are, for example, substrates that are solid and transparent, such as substrates composed of glass or a transparent or glass-like polymer, for example a tissue culture plate made of polystyrene. In one embodiment, said attachment layer has or is an amino functionalized surface. In one embodiment, said attachment layer is a surface coating on a substrate that allows for stable adherence of the sensor on the substrate, wherein, particularly, said surface coating consists of poly-L-ornithine (PLO).

In one embodiment, said sensor further includes a cell adherence layer on which cultured cells can be immobilized. The term "cell adherence layer", as used herein, is used synonymously with "cell adhesion layer" and is meant to refer to a layer allowing an adhesion and/or immobilization of cells. In one embodiment, said adherence layer is permeable to said analyte. In one embodiment, said cell adherence layer is composed of a material selected from the group consisting of collagen, ECM gel, fibronectin, gelatin, laminin, and proteoglycans. In one embodiment, said cell adherence layer separates the sensing layer from the cultured cells, such that the cultured cells are not in direct contact with said sensing layer. In one embodiment, said cell adherence layer has a thickness of less than 1 m.

In one embodiment, said analyte is a neurotransmitter, particularly a neurotransmitter selected from the group consisting of serotonin, dopamine, norepinephrine and epinephrine, more particularly dopamine or serotonin.

As discussed above, the present disclosure provides a use of a sensor as defined in any of the embodiments described above for the detection of an analyte, particularly a biomolecule secreted by cultured cells, in a sample.

In this use, said sensor, said analyte, said biomolecule and said cultured cells are as defined in any of the embodiments above.

Particularly said use occurs in vitro.

In one embodiment, said sample is a liquid sample.

In one embodiment, said analyte is not chemically modified during detection.

As discussed above, the present disclosure provides a method for the detection of an analyte, particularly a biomolecule secreted by cultured cells, in a sample, wherein said method includes the steps of providing a sensor as defined in any of the embodiments described above, said sensor including a biocompatible sensing layer including
a matrix, wherein said matrix is a polymer matrix or polymer gel matrix, and
organic nanoparticles embedded in said matrix, wherein said organic nanoparticles are capable of emitting light, particularly by photon up-conversion emission in the presence of said analyte, but not in the absence of said analyte, wherein said sensor optionally further includes plasmonic metal nanoparticles;
bringing said sensor in contact with said sample, such that said analyte, if present in said sample, can enter into said sensing layer of the sensor;
irradiating said sensor with light having a wavelength that equals the excitation wavelength for photon up-conversion of said organic nanoparticles;
detecting light emission at the emission wavelength, particularly of photon up-conversion, of said organic nanoparticles, wherein the presence (and optionally concentration) of said analyte is determined by the intensity of the light emission detected at the emission wavelength of photon up-conversion of said organic nanoparticles.

In this method for the detection of an analyte, said sensor, said analyte, said biomolecule, said cultured cells, said sensing layer, said matrix, said polymer matrix, said gel matrix, said organic nanoparticles and said metal nanoparticles are as defined in any of the embodiments above.

In one embodiment, said method for the detection of an analyte is an in vitro method.

In one embodiment, said sample is a liquid sample, more particularly tissue culture media that are or have been in contact with cultured cells.

In one embodiment, said light having a wavelength that equals the excitation wavelength for photon up-conversion of said organic nanoparticles has a wavelength of 630 nm or longer.

In one embodiment, said cultured cells are grown directly on top of said sensor (such that the cultured cells secrete the biomolecule to be detected into the culture media; the sensor detects then the presence of the secreted biomolecule in the culture media).

The term "biocompatible", as used herein, designates that a material, object or entity is non-toxic to biological systems (like organisms, cells or biomolecules) and does not have injurious effects on biological systems. In some embodiments, the term "biocompatible" specifically designates that a material, object or entity is non-toxic to biological cells, e.g. cells in cell culture or tissue; accordingly, a "biocompatible" sensing layer is a sensing layer that is non-toxic to cells in culture (on top of the sensing layer) or tissue culture cells (on top of the sensing layer). In the best case neither the cells in culture nor in tissue "notice" the presence of the sensing layer in anyway but function as usual (on their standard adherence layers) Hence, typically, the term "biocompatible" as used herein refers to "cell compatible". The terms may be used interchangeably.

As used herein, a nanoparticle is an "organic" nanoparticle if it includes at least one organic component, such as a polymeric organic matrix. An organic component, as used herein, is a component that includes carbon-carbon bonds. As used herein, the term "a metal nanoparticle" is meant to refer to any nanoparticle that is made up of or consists of a material which is a metal.

The term "polymer matrix", as used herein, is meant to refer to a matrix that includes a polymer or is made up of a polymer. A "polymer" is a substance composed of molecules characterized by the multiple repetition of one or more species of monomers. A polymer matrix can e.g. be formed by drying a film from polymer solution containing dispersed NPs.

The term "gel matrix", as used herein, is meant to refer to a matrix made up of a gel. A gel matrix can e.g. be formed by polymerisation of a solution containing gel precursors and NPs.

A "sensing layer", as used herein, is a layer for sensing of an analyte (i.e. detection of an analyte, such as a biomolecule secreted by cultured cells).

The term "biomolecule", as used herein, refers to any molecule produced by a living cell or a living organism (including viruses). This may include, but is not limited to, macromolecules such as proteins, polysaccharides, lipids, and nucleic acids (including DNA and RNA), as well as small molecules such as primary metabolites, secondary metabolites, and natural products. Special object of interest here are the antioxidants and neurotransmitters (sometimes herein also abbreviated as "NTs") (especially the ones with antioxidative, e.g. singlet oxygen scavenging properties). Other examples are adrenaline and ascorbic acid (but in different concentration range, not interfering with the NTs detection).

If the present application states that a component A is "chemically inert" with respect to another component B, this means that component A does not chemically react with component B.

The term "light emitter", as used herein, refers to a molecule or combination of molecules that, upon irradiation with light of a certain excitation wavelength, is capable of emitting light of a certain emission wavelength. The emitted light is generated by luminescence, particularly fluorescence.

A "sensitizer" is a chromophore molecule which is able to absorb light, particularly with high populated triplet states, undergo subsequent intersystem crossing to generate an excited triplet state and subsequently transfer the sensitizer triplet excitation to the triplet state of the light emitter included in the nanoparticle. In combination with a suitable light emitter (such as an organic chromophore molecule with emitting singlet states), a sensitizer can achieve photon up-conversion, as described in EP 2298849 A1 or US 2010/0330026 A1. Upon irradiation, the sensitizer absorbs light at the excitation wavelength. Upon subsequent intersystem crossing in the sensitizer molecule, an excited triplet state is reached. The sensitizer triplet excitation is transferred to the triplet state of the light emitter, followed by annihilation of two excited triplet states of the light emitter. The light emitted by said light emitter at said second wavelength region $\lambda_2$ is due to the triplet-triplet annihilation between two emitter excited triplets resulting in population of one of the emitter's singlet states which relaxes emitting light with wavelength $\lambda_2$.

Examples of sensitizers suitable for photon up-conversion are dyes containing d- or f-block elements with high excitation coefficient and a large anti-stokes shift, for example Pd tetrabenzoporphyin based chromophores like PdTBP (see also EP 2298849 A1 or US 2010/0330026 A1).

Examples of light emitters suitable for photon up-conversion are perylenes and anthracenes (see also EP 2298849 A1 or US 2010/0330026 A1).

A "metal particle", as used herein, refers to a particle consisting of a metal, a combination of different metals or a metal alloy. In one embodiment, a "metal particle" consists of one metal (i.e. of atoms of only one chemical element).

If the present disclosure refers to a metal particle being "enclosed within" a matrix or a certain layer, this designates a situation where said metal particle is surrounded at all sides by said matrix or said layer, such that the surface of said metal particle is completely covered by said matrix or said layer.

The nanoparticles according to the present disclosure are "capable of emitting light by photon up-conversion emission in the presence of said analyte, but not in the absence of said analyte". Accordingly, upon irradiation with light of appropriate wavelength, the nanoparticles will emit light by photon up-conversion emission in the presence of said analyte, but not in the absence of said analyte.

If the present disclosure refers to a metal nanoparticle "capable of enhancing the light emitted by said organic nanoparticles", this designates a situation where said metal nanoparticle is capable of plasmon enhancement. Such metal nanoparticle is also sometimes herein referred to as "plasmonic metal nanoparticle". At some instances, the present application refers to "metal particles that are in contact with each other". If a metal particle A "is in contact with" a metal particle B, this designates a situation where metal particle A and metal particle B directly touch each other, i.e. there is no intervening layer of a material that is neither part of metal particle A nor part of metal particle B, nor a gap, between said metal particle A and said metal particle B.

As used herein, a "water-miscible" solvent is a solvent that is completely miscible with water, e.g. THF, DMF, ethanol and other short-chained alcohols. If the present disclosure indicates that a molecule is capable of "specifically binding" to a certain analyte, this refers to a situation where the dissociation constant for the interaction of said molecule and said analyte is <1 µM, particularly <100 nM, more particularly <10 nM.

A molecule with an "enzymatic activity that allows to detect an analyte molecule" is a molecule that catalyzes an enzymatic reaction that is dependent on or strongly influenced by the presence/absence of the analyte molecule to be detected (e.g. because it is a substrate of the catalyzed reaction or because the catalytic activity of the molecule with enzymatic activity is strongly influenced by the presence/absence of the analyte molecule to be detected), such that by monitoring the reaction catalyzed by said molecule with an enzymatic activity that allows to detect the analyte molecule, the presence/absence of the analyte molecule or changes in the concentration of said analyte molecule can be detected.

The term "biologically active molecule" refers to a molecule that is capable of facilitating or inducing a specific cellular or tissue response.

The present inventors have found that a sensor including a matrix, organic nanoparticles, e.g. photon up-conversion nanoparticles, and metal nanoparticles as described above has various advantages with respect to improved detection and applicability as reported herein. The nanoparticles are enclosed in the matrix and thus stably held in place, but still accessible to the analyte molecules. Hence, in the case where the analyte molecules are for example biomolecules secreted by cultured cells, these biomolecules can enter the sensing layer and get access to the nanoparticles (e.g. by diffusion or are actively attracted towards and into the layer, e.g. by directed flow, pressure differential, osmosis, or centrifugation) to allow for detection, but neither do the nanoparticles move during this procedure nor do the cultured cells get in direct contact with components of the sensor like the nanoparticles or metal particles. Thus, the cells are not influenced during detection. For detection, the sensor is irradiated with light of the excitation wavelength at which absorbance for photon up-conversion of the organic nanoparticles occurs. In the presence of the analyte to be detected, a photon up-conversion signal is emitted at the emission wavelength at which photon up-conversion emission of the organic nanoparticles takes place. The intensity of this photon up-conversion signal is further enhanced by the metal particles present in the sensor by way of plasmon enhancement, and this signal can be detected via a photo detector (e.g. by eye or imaging sensor within a fluorescence microscopy setup) at the emission wavelength at which photon up-conversion emission of the organic nanoparticles takes place. The intensity of the emitted light allows to determine the presence and concentration of the analyte in the sample. The inventors have found that this setup results, due to the use of photon up-conversion emission, in a high signal-to-background ratio (no auto-fluorescence, no excitation scattering) and keeps potential damage to the cells and tissues studied low due to the long wavelength of the excitation light used for photon up-conversion. At the same time, the sensor has fast response times and, due to the presence of the metal particles, increased brightness and emission stability.

Thus, the main advantages of the sensor, of the use of a sensor according to the present disclosure for the detection of an analyte, and of the method for the detection of an analyte according to the present disclosure are:

- The sensor of the present disclosure overcomes the limitations mentioned in the introduction of this application for the detection and visualization of biomolecules in functional cell culture directly underneath/around cells, with good temporal and spatial resolution.
- The sensor allows non-invasive detection of an analyte for the detection and visualization of biomolecules in functional cell culture.
- If a biomolecule secreted by cells is to be analyzed, the cells do not come in direct contact with most components of the sensor, thus eliminating the problem that these components may have an influence on the cells. Specifically, the organic nanoparticles and the metal nanoparticles are embedded within the matrix of the sensing layer. If the sensor further includes a cell adhesion layer, then the sensing layer and, if present, the enhancement layer and attachment layers, are also completely separated from the cells.
- The sensor of the present disclosure is suitable for live cell imaging, without influencing/interacting with the cells.
- The sensor of the present disclosure allows for quantitative, non-invasive detection of an analyte (since the photon up-conversion emission depends on the concentration of analyte present).
- Since the detected signal is photon up-conversion emission, the sensor of the present disclosure has a high signal-to-background ratio (no auto-fluorescence, no excitation scattering).
- Potential damage to the cells and tissues studied is low due to the long wavelength of the excitation light used for photon up-conversion.
- The sensor has a fast response time (i.e. fast detection/imaging of an analyte/biomolecule in the range of 1 ms to 10 s is possible).
- Due to the presence of the metal nanoparticles, e.g. in both the polymer PUC NPs and further in the sensing layer, the sensor according to the present disclosure shows up-conversion emission with increased brightness and increased emission stability.
- The inclusion of antioxidants (especially singlet oxygen scavengers/quenchers) into the nanoparticles has the further advantage that a protection of the emitter and sensitizer chromophores is realized against reactive radicals. Moreover, a singlet oxygen quenching is achieved, which shifts the threshold for sensing.

Note that the present technology can also be configured as described below, for example by the following embodiments:

EMBODIMENTS

1. A sensor for the detection of an analyte, said sensor including a biocompatible sensing layer including
   a matrix, wherein said matrix is a polymer matrix or polymer gel matrix, and
   organic nanoparticles embedded in said matrix, wherein said organic nanoparticles are capable of emitting light, particularly by photon up-conversion emission in the presence of said analyte, but not in the absence of said analyte,
   wherein said sensor optionally further includes plasmonic metal nanoparticles, and wherein said sensor optionally further includes one or several cell adhesion layer(s) and/or one or several enhancement layers.
2. The sensor according to embodiment 1, wherein said analyte is a biomolecule, wherein, in particular, said analyte is selected from the group consisting of neurotransmitters, antioxidants, reactive oxygen species and hormones, more particularly a neurotransmitter selected from the group consisting of serotonin, dopamine, norepinephrine and epinephrine, even more particularly dopamine or serotonin.
3. The sensor according to any of the foregoing embodiments, wherein said matrix is an organic matrix, wherein, in particular, said matrix is a polymer matrix composed of a material selected from the group consisting of polyacrylamide (PAA), polyornithine, bovine serum albumin (BSA), collagen, e.g. fish, chicken, bovine, or porcine collagen, gelatin, chitosan, poly-1-lysine, laminin, gel-forming peptides, hydromatrix peptides or combinations thereof, more particularly polyacrylamide (PAA).
4. The sensor according to any of the foregoing embodiments, wherein said organic nanoparticles include a light emitter and a sensitizer, wherein, in particular, said sensitizer is capable of absorbing light at a first wavelength region $w \leq \lambda_1 \leq x$, and said light emitter is capable of emitting light at a second wavelength region $y \leq \lambda_2 \leq z$, wherein $\lambda_2 \leq \lambda_1$, and wherein, upon absorption of light by said sensitizer at said first wavelength region $w \leq \lambda_1 \leq x$, said light emitter emits light at said second wavelength region $y \leq \lambda_2 \leq z$.
5. The sensor according to embodiment 4, wherein said light emitted by said light emitter at said second wavelength region $\lambda_2$ is due to an up-conversion process based on triplet-triplet annihilation which up-conversion process occurs upon absorption of light by said sensitizer at said first wavelength region $\lambda_1$.
6. The sensor according to any of embodiments 4 and 5, wherein the light emitted by said light emitter has a wavelength in the range of from 360 to 750 nm, particularly 420 to 620 nm, and/or wherein said sensitizer absorbs light at a wavelength in the range of from 450 to 1600 nm, particularly from 530 to 860 nm, more particularly from 620 to 750 nm.
7. The sensor according to any of embodiments 4-6, wherein said light emitter is a molecule selected from the group consisting of anthracenes, perylenes, perylene derivatives such as perylene monoimides or perylene diimides, coumarins and BODIPY dyes, wherein, in particular, said at least one light emitter has a structure represented by Formula (I) or (II) or includes a molecule having the structure represented by Formula (I) or (II):

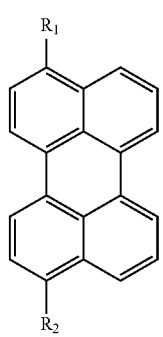

Formula (I)

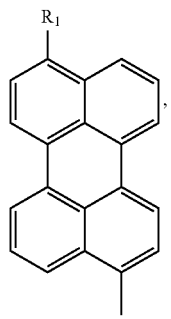

Formula (II)

wherein $R_1$ and $R_2$ are independently selected from the group consisting of hydrogen and a moiety with the structure represented by Formula (III), wherein at least one of $R_1$ and $R_2$ is a moiety with the structure represented by Formula (III):

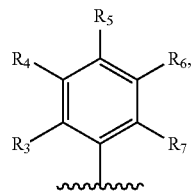

Formula (III)

wherein $R_3$, $R_4$, $R_5$, $R_6$ and $R_7$ are independently selected from the group consisting of H, F, and tri-fluoro-methyl (—$CF_3$),
wherein at least one of $R_3$, $R_4$, $R_5$, $R_6$ and $R_7$ is F or tri-fluoro-methyl (—$CF_3$),
wherein, in particular, $R_1$ and/or $R_2$ is a moiety represented by Formula (IV), Formula (V) or Formula (VI):

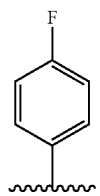

Formula (IV)

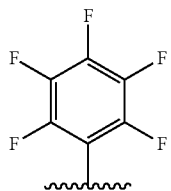

Formula (V)

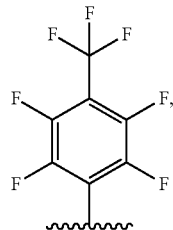

Formula (VI)

wherein, more particularly, said at least one light emitter has a structure represented by Formula (VII), Formula (VIII) or Formula (IX), or includes a molecule having the structure represented by Formula (VII), Formula (VIII) or Formula (IX):

Formula (VII)

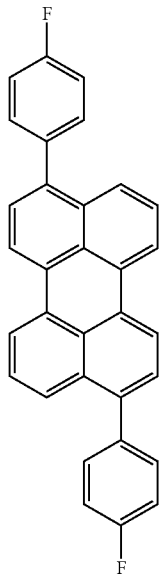

Formula (VIII)

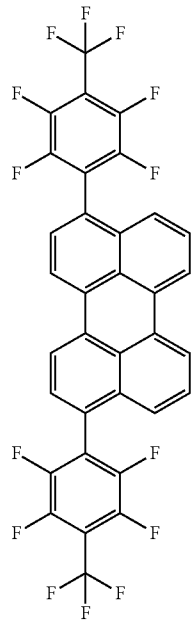

Formula (IX)

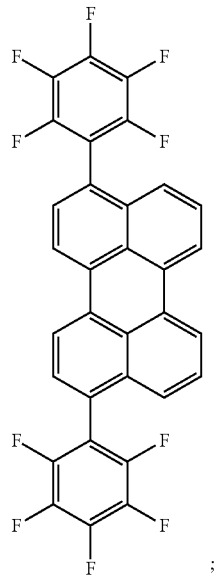

;

or wherein said at least one light emitter has the structure represented by Formula (X) or includes a molecule having the structure represented by Formula (X):

Formula (X)

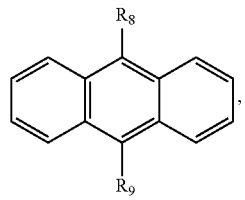

wherein $R_8$ and $R_9$ are independently selected from the group consisting of hydrogen and a moiety with the structure represented by Formula (XI), wherein at least one of $R_8$ and $R_9$ is a moiety with the structure represented by Formula (XI):

Formula (XI)

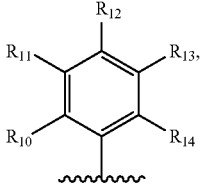

wherein $R_{10}$, $R_{11}$, $R_{12}$, $R_{13}$ and $R_{14}$ are independently selected from the group consisting of H, F, and tri-fluoro-methyl (—$CF_3$), wherein at least one of $R_{10}$, $R_{11}$, $R_{12}$, $R_{13}$ and $R_{14}$ is F or tri-fluoro-methyl (—$CF_3$), wherein, more particularly, $R_8$ and/or $R_9$ is the moiety represented by Formula (XII), Formula (XIII), Formula (XIV), Formula (XV) or Formula (XVI):

Formula (XII)
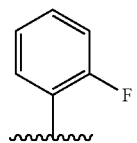

Formula (XIII)
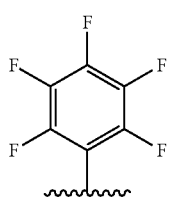

Formula (XIV)
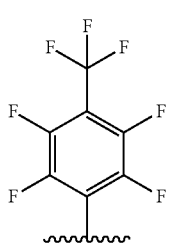

Formula (XV)
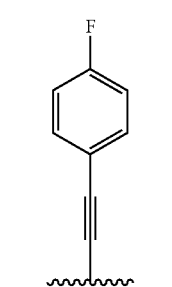

Formula (XVI)
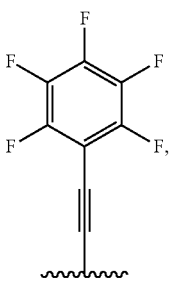

or wherein, more particularly, said at least one light emitter has the structure represented by Formula (XVII), Formula (XVIII), Formula (XIX), Formula (XX), Formula (XXI) or Formula (XXII), or includes a molecule having the structure represented by Formula (XVII), Formula (XVIII), Formula (XIX), Formula (XX), Formula (XXI) or Formula (XXII):

Formula (XVII)
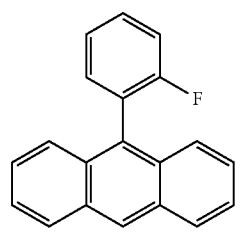

Formula (XVIII)
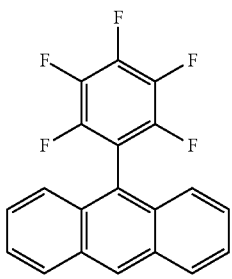

Formula (XIX)
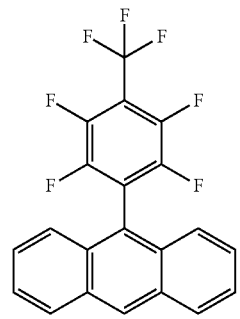

Formula (XXX)
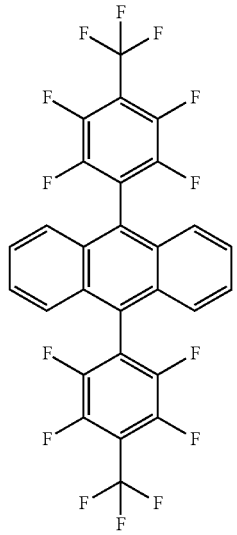

Formula (XXI)
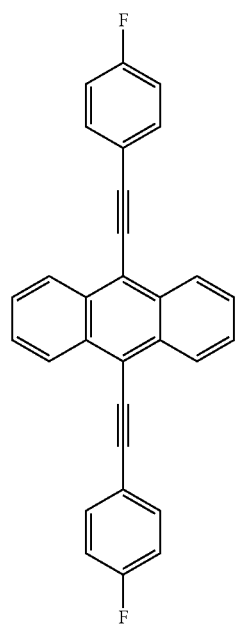
Formula (XXII)
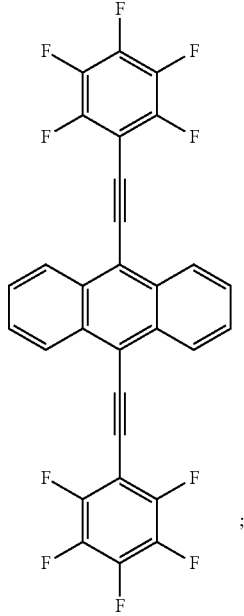
or wherein said at least one light emitter has a structure represented by one of the following structures or includes a molecule having a structure represented by one of the following structures:
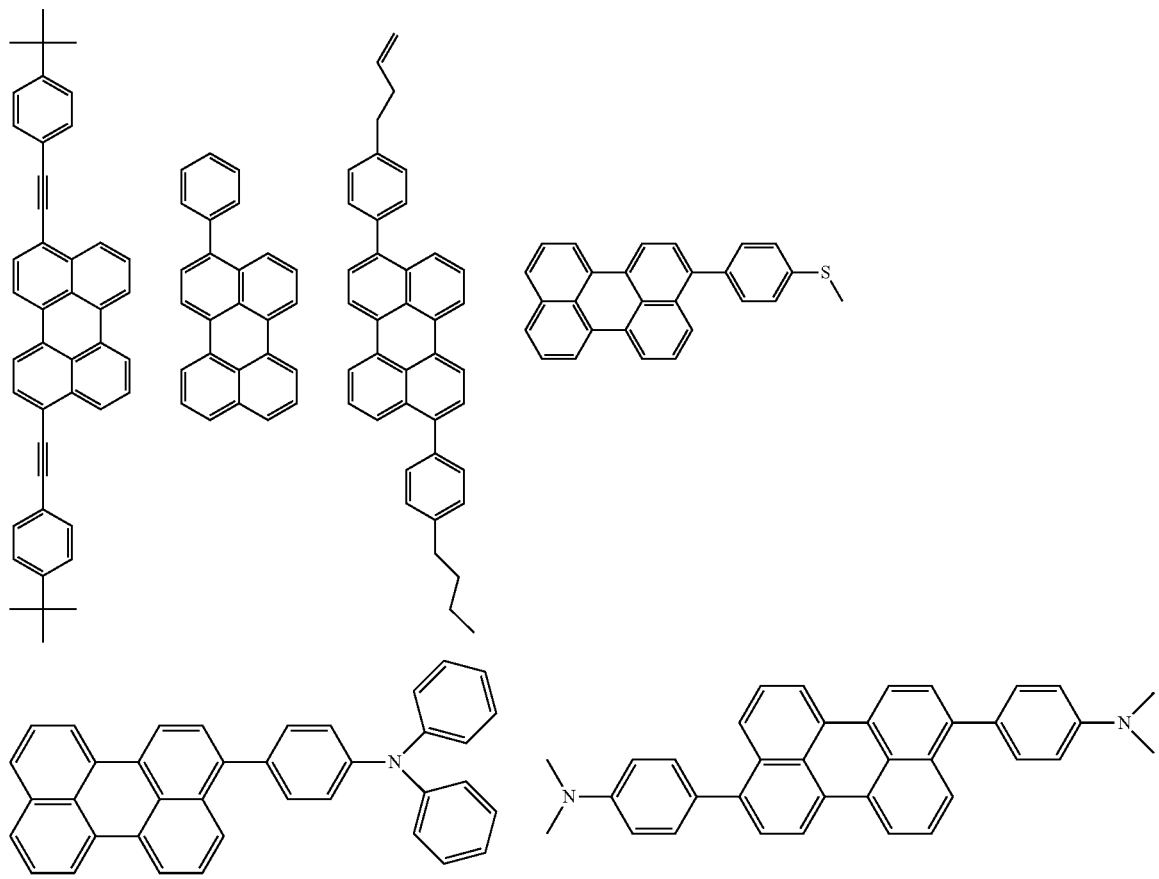

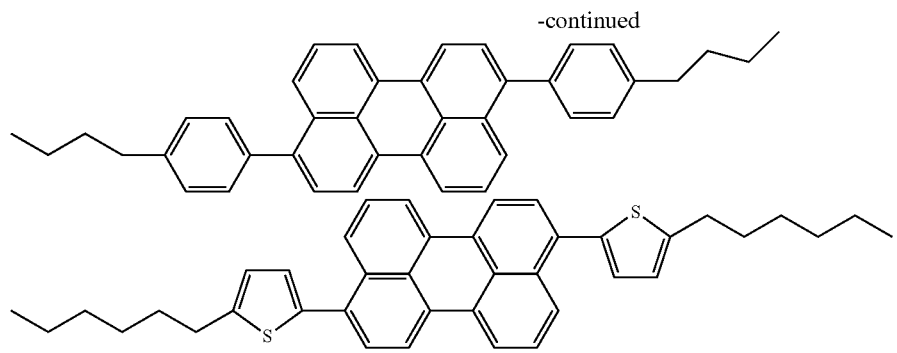

or wherein said light emitter has the structure represented by Formula (XXIII), (XXIV) or (XXV) or includes a molecule having the structure represented by Formula (XXIII), (XXIV) or (XXV):

Formula (XXIII)

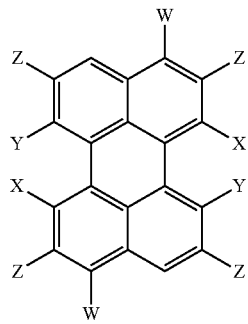

Formula (XXIV)

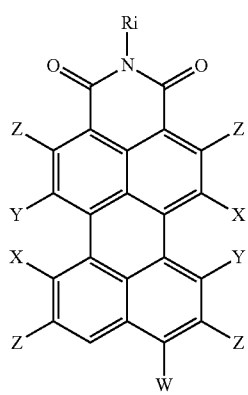

Formula (XXV)

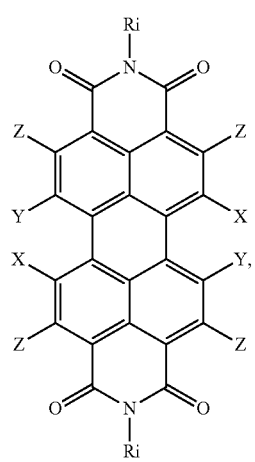

wherein W in formulae XXIII-XXV is selected from one of the following groups:

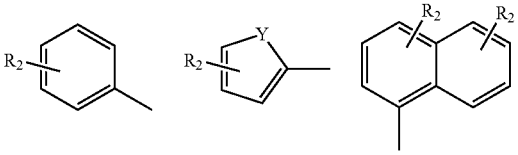

wherein Y as used in formula W is selected from the group consisting of $CH_2$, S, O, Se and N—$R_2$, and wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a halogenated alkyl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a halogenated alkyl group, a heteroaryl group and a fluorenyl group, wherein, particularly, $R_2$ has not more than 6 carbon atoms;

wherein X and Y in formulae XXIII-XXV are independently selected from the following groups:

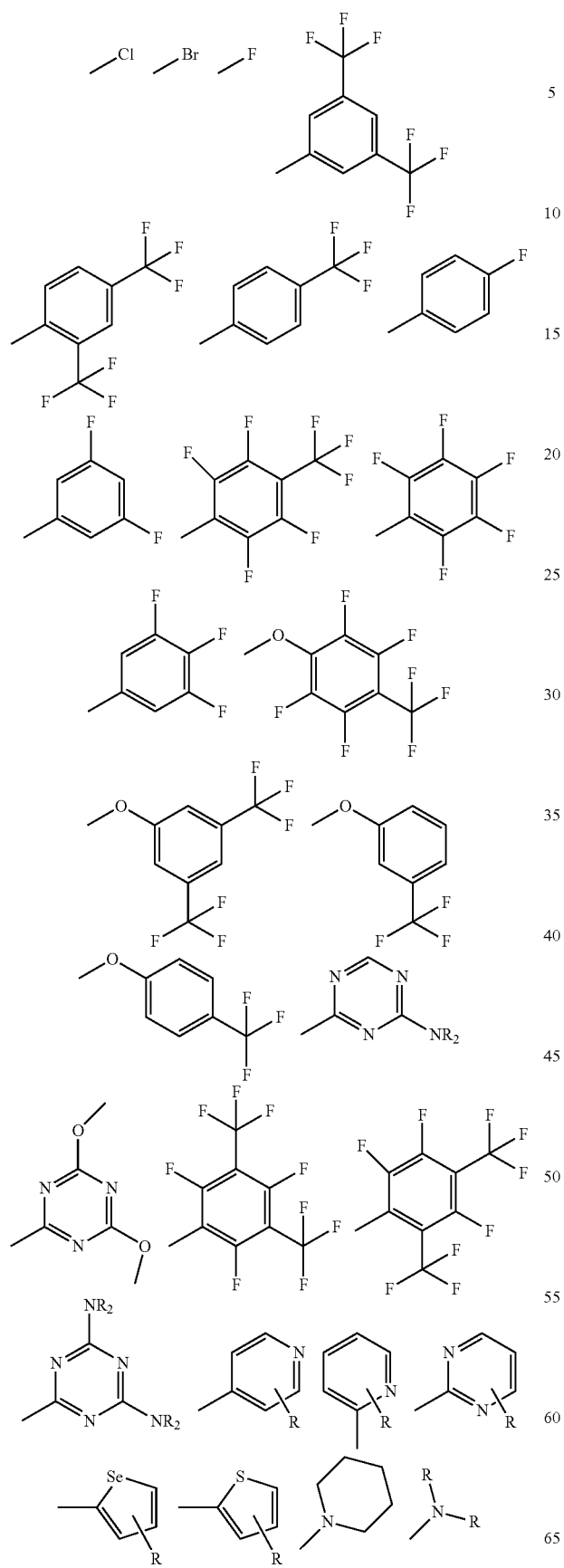

and wherein R is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a halogenated alkyl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a halogenated alkyl group, a heteroaryl group and a fluorenyl group, wherein, particularly, R has not more than 6 carbon atoms, wherein Z in formulae XXIII-XXV is selected from the following groups:

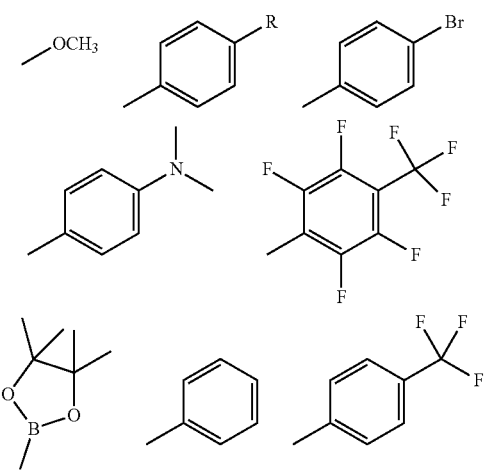

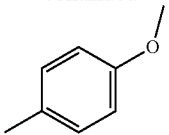

and wherein $R_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a halogenated alkyl group, a heteroaryl group, a fluorenyl group, an amino group, a nitro group, an OH group, an SH group, and a group —O—$R_3$, wherein $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a halogenated alkyl group, a heteroaryl group and a fluorenyl group, wherein, in particular, $R_2$ has not more than 6 carbon atoms, wherein Ri is selected from the following groups:

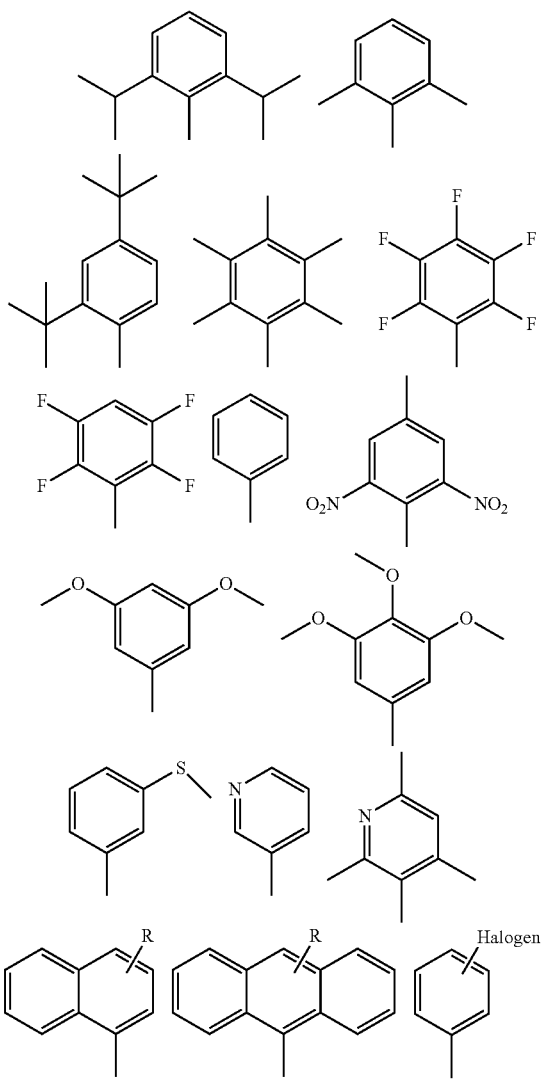

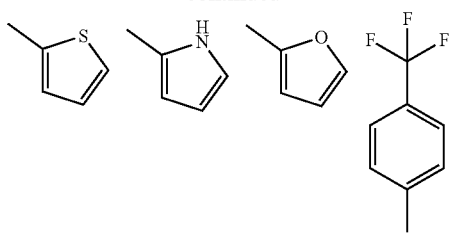
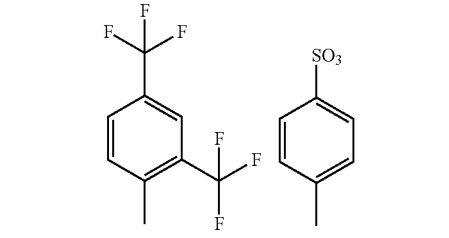
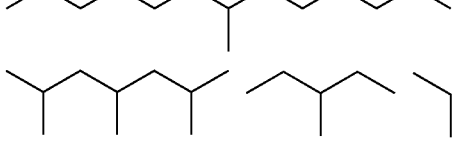
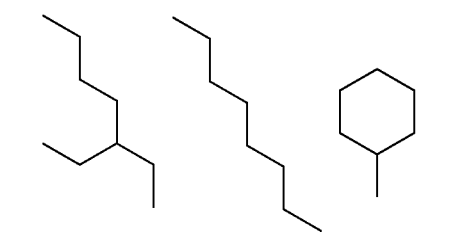
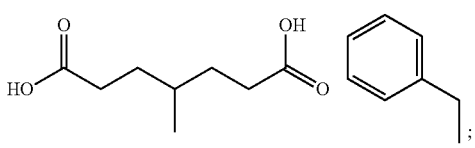

wherein, particularly, W is selected from the following groups:

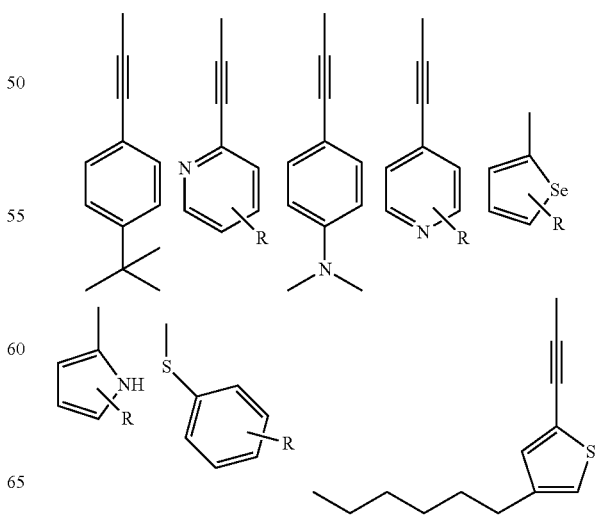

-continued
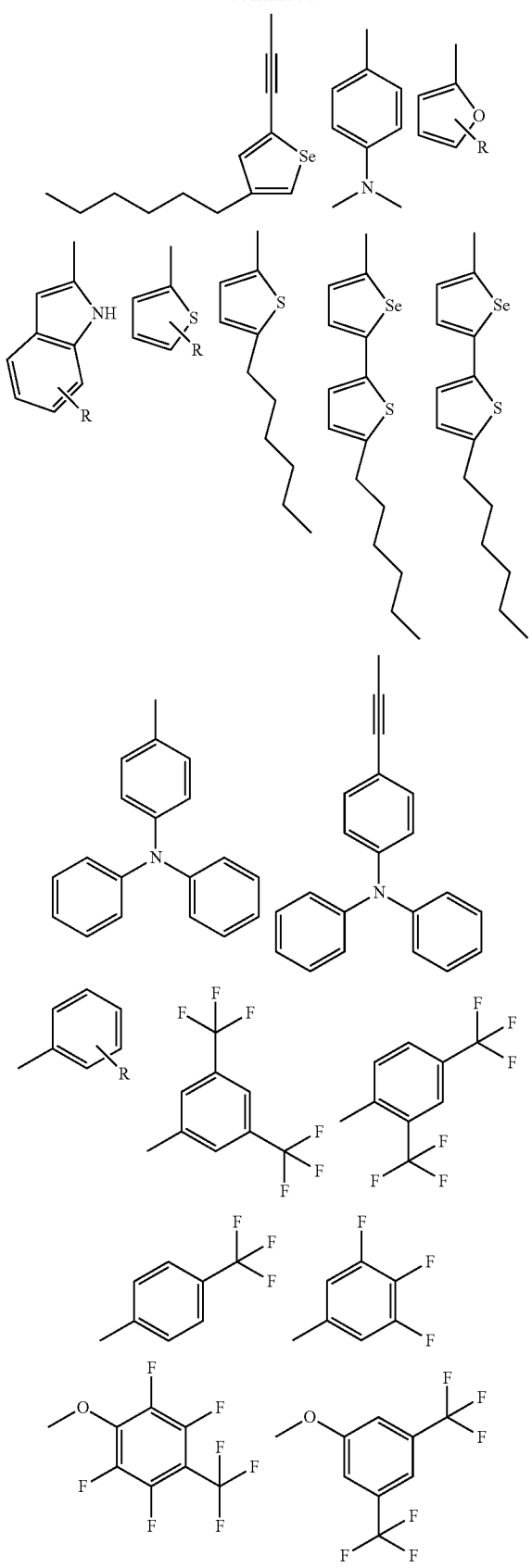
-continued
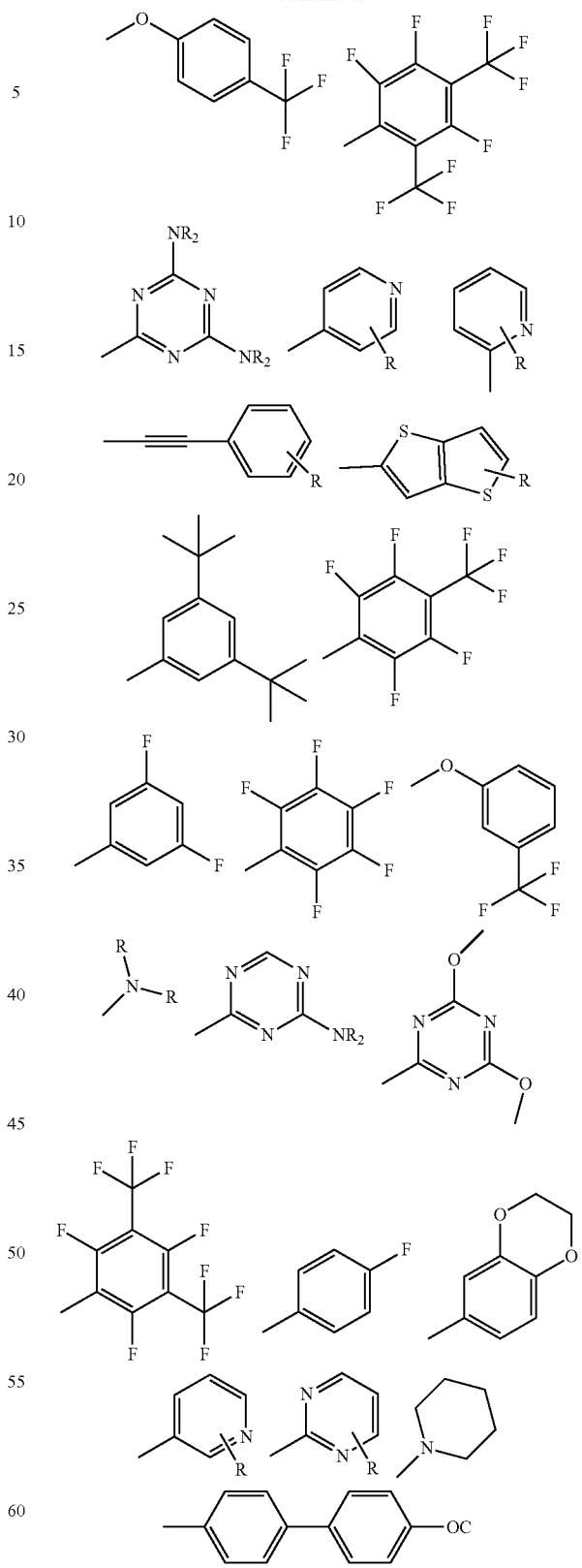
With R, $R_i$, $R_2$ being as defined above;
or wherein said at least one light emitter has a structure selected from one of the following:

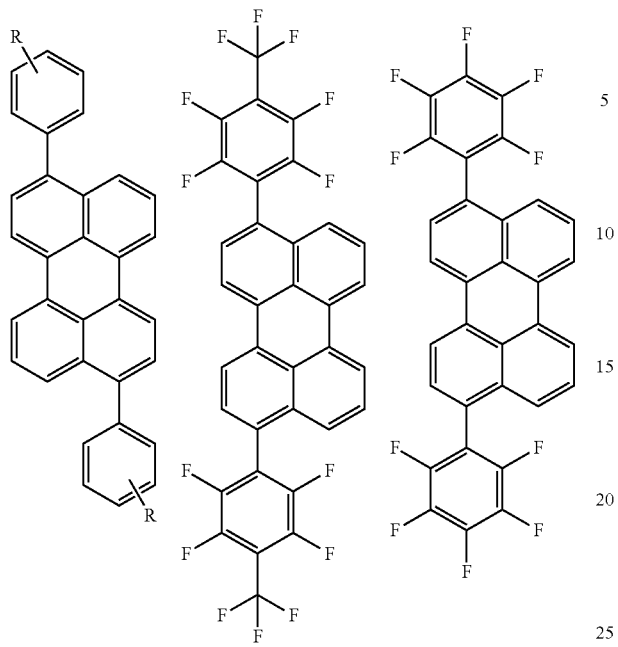

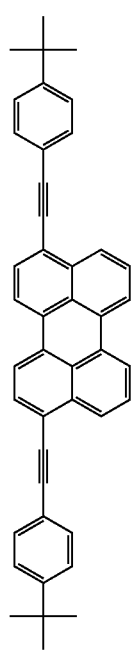

wherein R is a linear or branched alkyl group, particularly with not more than 6 carbon atoms;
or wherein said light emitter has the structure represented by Formula (XXVI) or includes a molecule having the structure represented by Formula (XXVI):

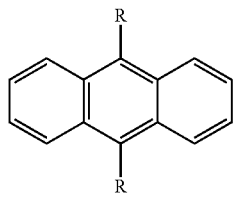

Formula (XXVI)

wherein R is selected from the following groups:

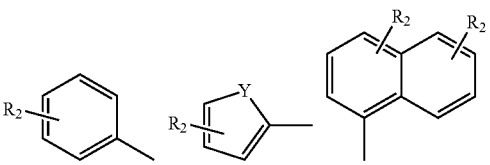

wherein Y is selected from the group consisting of CH$_2$, S, O, Se and N—R$_2$, and wherein R$_2$ is selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a halogenated alkyl group, a heteroaryl group, a fluorenyl group, an OH group, an SH group, and a group —O—R$_3$, wherein R$_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a halogenated alkyl group, a heteroaryl group and a fluorenyl group, wherein, particularly, R$_2$ has not more than 6 carbon atoms;

or wherein R is selected from the following groups:

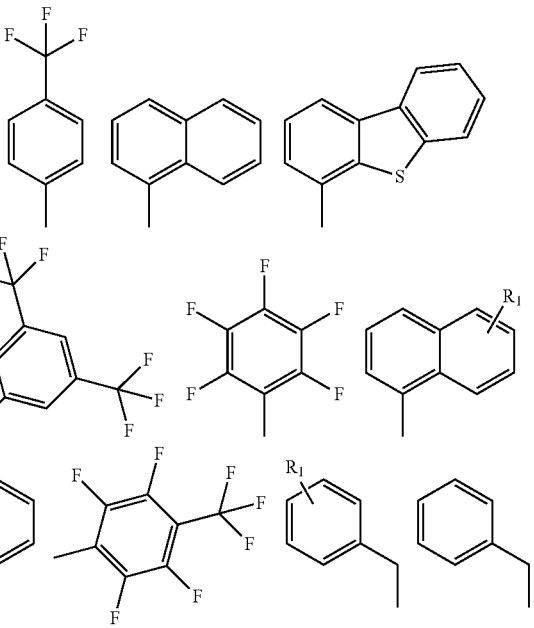

-continued

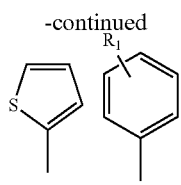

wherein $R_1$ is a linear or branched alkyl group, preferably with not more than 6 carbon atoms;
or wherein said at least one light emitter has a structure selected from one of the following or includes a molecule having a structure selected from one of the following:

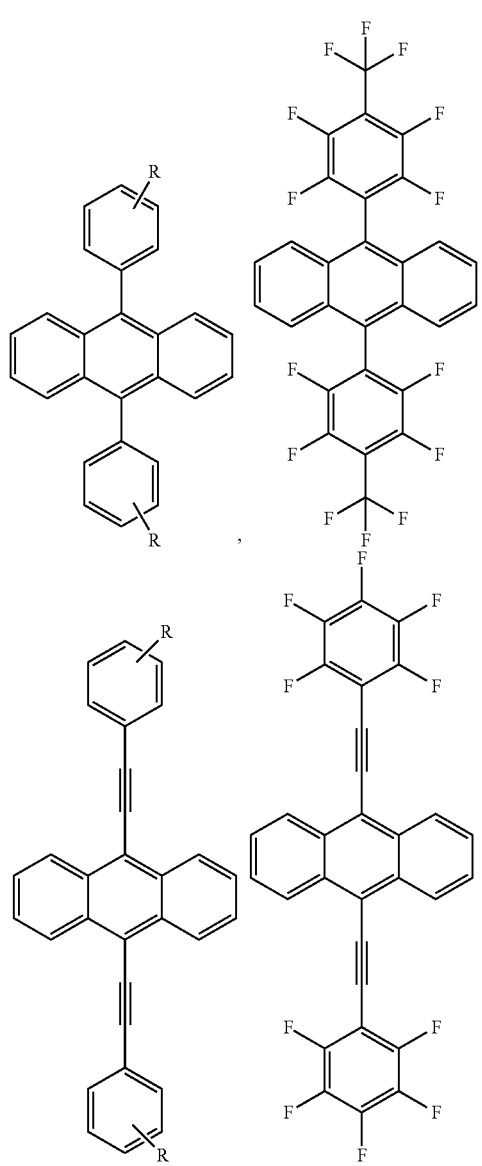

wherein R is a linear or branched alkyl group, preferably with up to 6 carbon atoms.
and/or wherein said at least one sensitizer is or includes a porphyrin or a phthalocyanine,
wherein, in particular, said at least one sensitizer has a structure represented by Formula (XXVII), Formula (XXVIII), Formula (IXXX), Formula (XXX) or Formula (XXXI) or includes a molecule having a structure represented by Formula (XXVIII), Formula (IXXX), Formula (XXX) or Formula (XXXI):

Formula (XXVII)

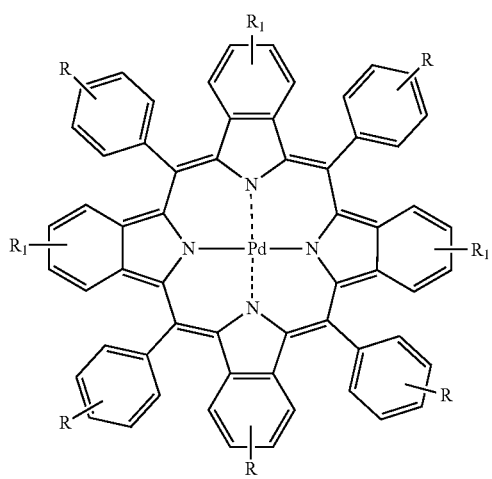

wherein $R_1$ is hydrogen, a linear or branched alkyl group, in particular with up to 6 carbon atoms, or a benzene ring,
and wherein R is a linear or branched alkyl group, in particular with up to 6 carbon atoms;

Formula (XXVIII)

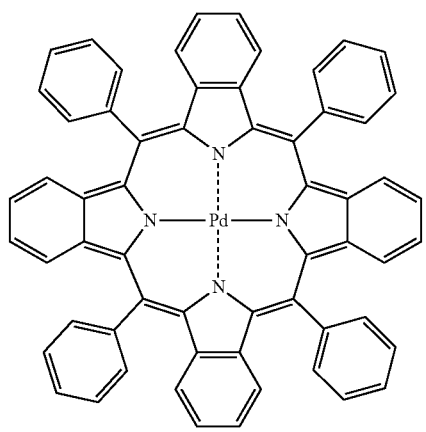

Formula (IXXX)

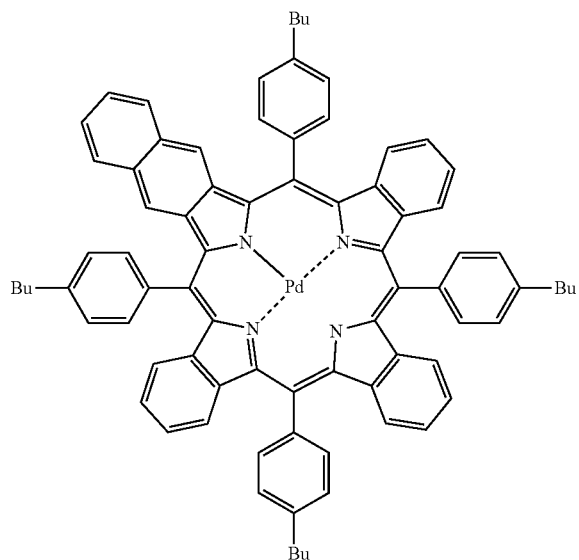

Formula (XXX)

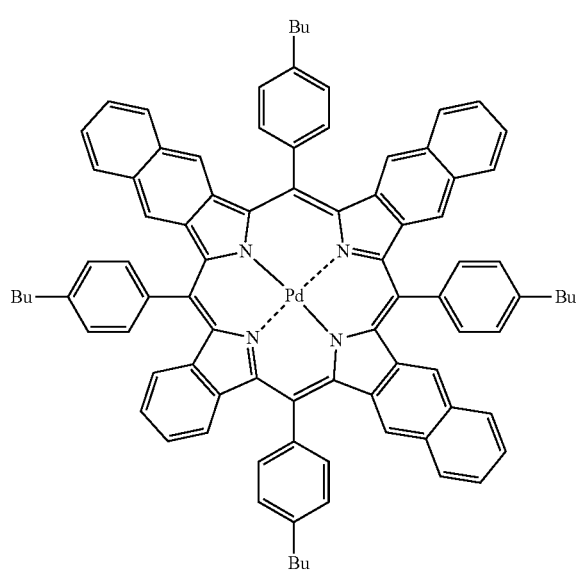

Formula (XXXI)

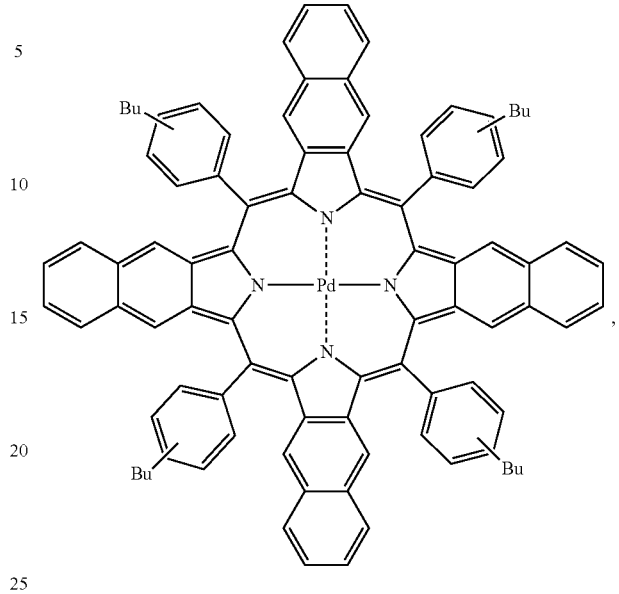

wherein, in particular, said sensitizer has the structure represented by Formula (XXVIII):

Formula (XXVIII)

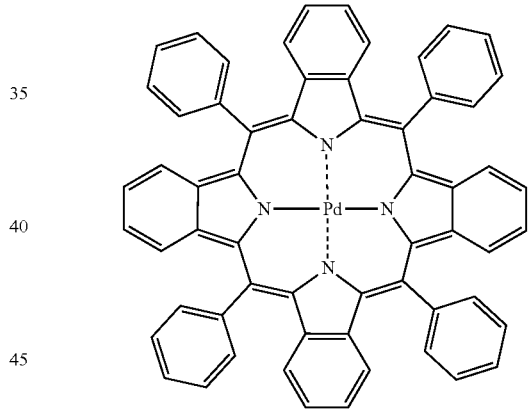

8. The sensor according to any of the foregoing embodiments, wherein said metal nanoparticles are distributed within said matrix of said sensing layer and/or said sensor includes an enhancement layer in which said metal nanoparticles are distributed and/or said metal nanoparticles are distributed within said organic nanoparticles, wherein, in particular, said metal nanoparticles are not in contact with each other and/or wherein said metal nanoparticles have a diameter in the range of from 1 to 100 nm, in particular in the range of from 4 to 80 nm, more particularly in the range of from 10 to 60 nm, more particularly in the range of from 10 to 50 nm, and/or wherein said metal nanoparticles consist of a material selected from the group consisting of Ag, Au, and Co, in particular of Ag, and/or wherein said metal nanoparticle(s) is(are) plasmonic and/or magnetic.

9. The sensor according to any of the foregoing embodiments, wherein said sensing layer further includes at least one antioxidant, in particular a singlet oxygen scavenger, a reactive oxygen scavenger (ROS) scavenger or a radical scavenger, most particular singlet oxygen scavenger, wherein, in particular, said at least one antioxidant is distributed homogeneously within said matrix of said sensing layer and/or said at least one antioxidant is distributed within said organic nanoparticles.

10. The sensor according to any of the foregoing embodiments, wherein said organic nanoparticles include functional groups at their surface that allow to covalently couple further molecules to the organic nanoparticles, wherein, in particular, said functional groups are selected from the group consisting of —COOH (carboxylate), —NH$_2$, —SH (thiol), —NHS, alkynyl, —N$_3$, aldehyde, ketone and biotin group.

11. The sensor according to any of the foregoing embodiments, wherein said organic nanoparticles include molecules or chemical groups attached to their surface that are capable of specifically binding to said analyte molecule or that have an enzymatic activity that allows to detect said analyte molecule, wherein, in particular, said molecules attached to the surface of the organic nanoparticles are antibody molecules, affibodies, aptamers or enzyme molecules.

12. The sensor according to any of the foregoing embodiments, wherein said sensor further includes an attachment layer by which the sensor can be immobilized on a substrate, in particular by covalent and/or electrostatic forces, wherein, in particular, said attachment layer is composed of glass or a transparent polymer, and or wherein in particular said substrate is solid and transparent, such as a substrate composed of glass or a transparent or glass-like polymer, for example a tissue culture plate made of polystyrene, wherein, more particularly, said attachment layer is a surface coating on a substrate that allows for stable adherence of the sensor on the substrate, wherein, particularly, said surface coating consists of poly-L-ornithine (PLO) and/or glutardialdehyde (GDA).

13. The sensor according to any of the foregoing embodiments, wherein said sensor further includes a cell adherence layer on which cultured cells can be immobilized, wherein, in particular, said cell adherence layer is composed of a material selected from the group consisting of collagen, ECM (extracellular matrix) gel, fibronectin, gelatin, laminin, and proteoglycans.

14. A method of producing a sensor according to any of the foregoing embodiments, said sensor including a biocompatible sensing layer including
a matrix, wherein said matrix is a polymer matrix or polymer gel matrix, and
organic nanoparticles embedded in said matrix, wherein said organic nanoparticles are capable of emitting light by photon up-conversion emission in the presence of said analyte, but not in the absence of said analyte;
wherein said sensor optionally further includes plasmonic metal nanoparticles, and optionally, one or several cell adhesion layers;
said method including the steps of:
(Variant A: plasmonic metal nanoparticles distributed in polymer matrix or gel matrix:)
providing, in any order, organic nanoparticles capable of emitting light by photon up-conversion emission (=PUC organic nanoparticles), plasmonic metal nanoparticles, polymer(s) for forming said polymer matrix or precursors of said gel matrix, and a substrate, optionally with attachment layer/coating thereon; and
either, for the preparation of a polymer matrix: preparing a dispersion including said PUC organic nanoparticles and said metal nanoparticles in a water-based solution of the polymer(s) for forming said polymer matrix;
applying the dispersion onto said substrate or onto the attachment layer/coating if present on said substrate);
drying the applied dispersion, thus forming a sensing layer;
optionally, applying cell adhesion layer(s) on top via drop casting followed by washing;
or, for the preparation of a gel matrix: preparing a dispersion including said PUC organic nanoparticles and said metal nanoparticles in a solution of the gel precursors and gel polymerisation initiators for forming said gel matrix;
applying the dispersion, particularly a droplet thereof, onto said substrate or onto the attachment layer/coating if present on said substrate;
placing a thin glass, such as a microscope slide cover slip, with hydrophobic surface on top of the dispersion to define thickness of said gel matrix and allowing the gel to polymerize;
removing the thin glass;
optionally, applying cell adhesion layer(s) on top via drop casting followed by washing;
thereby providing a cell compatible sensor;
or said method including the steps of:
(Variant B: plasmonic metal nanoparticles distributed in a separate enhancement layer:)
providing, in any order, organic nanoparticles capable of emitting light by photon up-conversion emission (=PUC organic nanoparticles), polymer(s) for forming said polymer matrix or precursors of said gel matrix, a substrate, optionally with attachment layer/coating thereon, a metal material in a form suitable to be applied as a separate layer, either in the form of a layer of plasmonic metal nanoparticles or a thin layer of metal deposited via vacuum deposition, said layer of plasmonic metal nanoparticles or said thin layer of metal being capable of enhancing light emitted by said organic nanoparticles by way of plasmon enhancement, wherein particularly said thin layer of metal or said layer of plasmonic metal nanoparticles has a thickness of approximately 10-50 nm;
applying said thin layer of metal or said layer of plasmonic metal nanoparticles onto said substrate, thereby forming an enhancement layer on said substrate for enhancement of light emitted by said organic nanoparticles;
and thereafter forming a sensing layer on top of said enhancement layer by the following steps:
either, for the preparation of a polymer matrix: preparing a dispersion including said PUC organic nanoparticles in a water-based solution of the polymer(s) for forming said polymer matrix;
applying the dispersion onto said substrate or onto the attachment layer/coating if present on said substrate;
drying the applied dispersion, thus forming a sensing layer;
optionally, applying cell adhesion layer(s) on top via drop casting followed by washing;
or, for the preparation of a gel matrix: preparing a dispersion including said PUC organic nanoparticles in a solution of the gel precursors and gel polymerisation initiators for forming said gel matrix;

applying the dispersion, particularly a droplet thereof, onto said substrate or onto the attachment layer/coating if present on said substrate;
placing a thin glass, such as a microscope slide cover slip, with hydrophobic surface on top of the dispersion to define thickness of said gel matrix and allowing the gel to polymerize;
removing the thin glass, thus forming a sensing layer;
optionally, applying cell adhesion layer(s) on top via drop casting followed by washing;
or alternatively first forming a sensing layer on the substrate by the above-mentioned sequence of steps and thereafter forming an enhancement layer on said sensing layer by the above-mentioned sequence of steps, or, alternatively, first forming an enhancement layer on said substrate, thereafter forming a sensing layer, and thereafter forming a second enhancement layer on top of said sensing layer;
thereby providing a cell compatible sensor;
or said method including the steps of:
(Variant C: plasmonic metal nanoparticles distributed within organic nanoparticles:)
  providing, in any order, organic nanoparticles capable of emitting light by photon up-conversion emission (=PUC organic nanoparticles), said PUC organic nanoparticles containing metal nanoparticles inside, further providing, in any order, a radical scavenger, in particular an antioxidant, and additional metal nanoparticles that are capable of enhancing light emitted by said organic nanoparticles by way of plasmon enhancement, polymer(s) for forming said polymer matrix or precursors of said gel matrix, and a substrate, optionally with attachment layer/coating thereon;
  either for the preparation of a polymer matrix: preparing a dispersion including said PUC organic nanoparticles containing inside metal nanoparticles, and antioxidant and said additional metal nanoparticles in a water-based solution of the polymer(s) for forming said polymer matrix;
  applying the dispersion onto said substrate or onto the attachment layer/coating if present on said substrate;
  drying the applied dispersion, thus forming a sensing layer;
  optionally, applying cell adhesion layer(s) on top via drop casting followed by washing;
  or, for the preparation of a gel matrix: preparing a dispersion including said PUC organic nanoparticles and said additional plasmonic metal nanoparticles in a solution of the gel precursors and gel polymerisation initiators for forming said gel matrix;
  applying the dispersion, particularly a droplet thereof, onto said substrate or onto the attachment layer/coating if present on said substrate;
  placing a thin glass, such as a microscope slide cover slip, with hydrophobic surface on top of the dispersion to define thickness of said gel matrix and allowing the gel to polymerize;
  removing the thin glass;
  optionally, applying cell adhesion layer(s) on top via drop casting followed by washing;
  thereby providing a cell compatible sensor.
15. Use of a sensor according to any of embodiments 1-13 for the detection of an analyte, in particular a biomolecule secreted by cultured cells, in a sample, wherein, in particular, said use is carried out in vitro.

EXAMPLES

Example 1

Preparation of Nanoparticles

This example describes the optimised production of examples of multicomponent nanoparticles in accordance with the present disclosure. These special, original designed nanoparticles are prepared by rapidly mixing water into a cooled, stirring, solution of an optimised organic matrix, optimised surface stabiliser or dispersant, dyes-including specially developed hydrophobic dyes with even more efficient incorporation) an emitter and a sensitizer in dry THF under an inert atmosphere. In addition to the organic components, silver nanoparticles can be added to the organic phase before mixing. The procedure and the components of the nanoparticles were optimized for sensitivity, increase in upconversion signal and size, which also effects transparency of the solution.

The size and size distribution of the nanoparticles produced in this method is very good if the aqueous phase and organic phase are chilled and mixed very rapidly. To accomplish this two electronically controlled valves, that quickly move from fully closed to fully open in under 0.2 s are used. A partial vacuum of 30 mbar in the mixing chamber also facilitates the very fast addition of the aqueous phase to the organic phase. This, along with rapid stirring of the solution, allows a colloidal solution to be formed upon the water addition. The dispersion was then stirred under inert atmosphere for over an hour and the organic solvent evaporated under reduced pressure. Following cooling overnight the dispersion was filtered to remove large masses, and centrifuged within a concentrator tube remove small molecules and aggregates and collect the organic particles. Nanoparticles were collected in water (2 ml or 0.5 ml) and stored at 4° C.

What is described in this example is a representative procedure.

Purpose/Aim:

This example details a method for the controlled, repeatable, formation of nanoparticles with consistent size and polydispersity index (PDI). This procedure was developed to yield methods, which allows for the inclusion of fluorescent dye(s), or upconversion systems (sensitizers & emitters) into the nanoparticles-especially as aqueous dispersions.

The applications of such dye-loaded nanoparticles are diverse (including fluorescence, or PUC, or both in combination), for example:

To manufacture bright, stable, with controllable size emissive nanoparticles in aqueous dispersions—for application as labels for e.g. proteins and cells. In a similar manner the watersoluble dyes are used.

For direct uptake by cells-imaging of live cells or their flow cytomteric investigations (following the uptake of the NPs by the cells)

For attachment to cells surface-flow cytometry/sorting- after the NPs are attached on the cell surface (here polystyrene (PS) microparticles are used in the examples as cell model)

The formation of sensing/imaging layers, e.g. in the development of a sensing layer which can be (is) used in combination with neuronal cell cultures as non-invasive neuroimaging system for the visualization of neuronal activities. To manufacture PUC-NPs to sense the NT dopamine or other NTs like serotonin, as well as other biomolecules which can scavenge/quench singlet oxygen—as added to the NPs dispersion—as released by neuronal cells or from any other source.

To control the PUC outcome from the NPs as well as their incorporation in ESL—for control of sensitivity and dynamic range of ESL for dopamine sensing Solution/Procedure (Experimental):

The main optimisation pathways of the NPs core:

Variation of the Components:

Variation of the ratio/amount of the matrix components e.g. PMMA (polymethylmethacrylate) and PHD (heptadecyl benzene)

Variation of the surface stabilizer and its concentration

Variation also combinations of the emitter molecules and there concentration

Variation also combination of the sensitizer molecules also their concentration

Addition/variation also combinations of antioxidant(s) (singlet oxygen scavenger/quencher or ROS scavenger) and their concentration, Variation of the Mixing Conditions Air vs. inert atmosphere Temperature of the organic solution and the water and as follows influence also the size and the surface potential of the nanoparticles as well as on their emissive/sensing properties and their further attachment/functionalisation properties.

The following procedure details the production of nanoparticles. Typically 4 to 6 variations (nanoparticles comprised of, for example, differing Ag nanoparticles and antioxidant concentration are typically prepared in one day.

This method of preparing the nanoparticles is to inject cold water into an organic phase containing the, matrix components, the stabiliser, the antioxidants (if any), the metal nanoparticles and the dye molecules. Then by adding water, quickly and with a large amount of agitation, to this phase nanoparticles of consistent size and polydispersity index (PDI) are produced in a controlled, repeatable manner for the corresponding combination of components.

Typical Materials:
  Surface stabilizer: CoPEG (Glycolic acid ethoxylate 4-nonylphenyl ether)
  Matrix: PHD(Heptadecylbenzene), PMMA
  Emitters: e.g. 3,10-Bis((4-tert-butylphenyl)ethynyl)perylene or 3,9(10)-bis(2,3,5,6-tetrafluoro-4-(trifluoromethyl)phenyl)perylene
  Sensitizer: PdTBP
  Organic Solvent: THF
  Additional Nanoparticles 4 nm AgNP
  Antioxidant: 6-O-Palmitoyl-L-ascorbic acid or lipoic acid, or other (see the description), The general components of exemplary nanoparticles in accordance with the present disclosure are depicted in FIG. 1.

Figure 2:
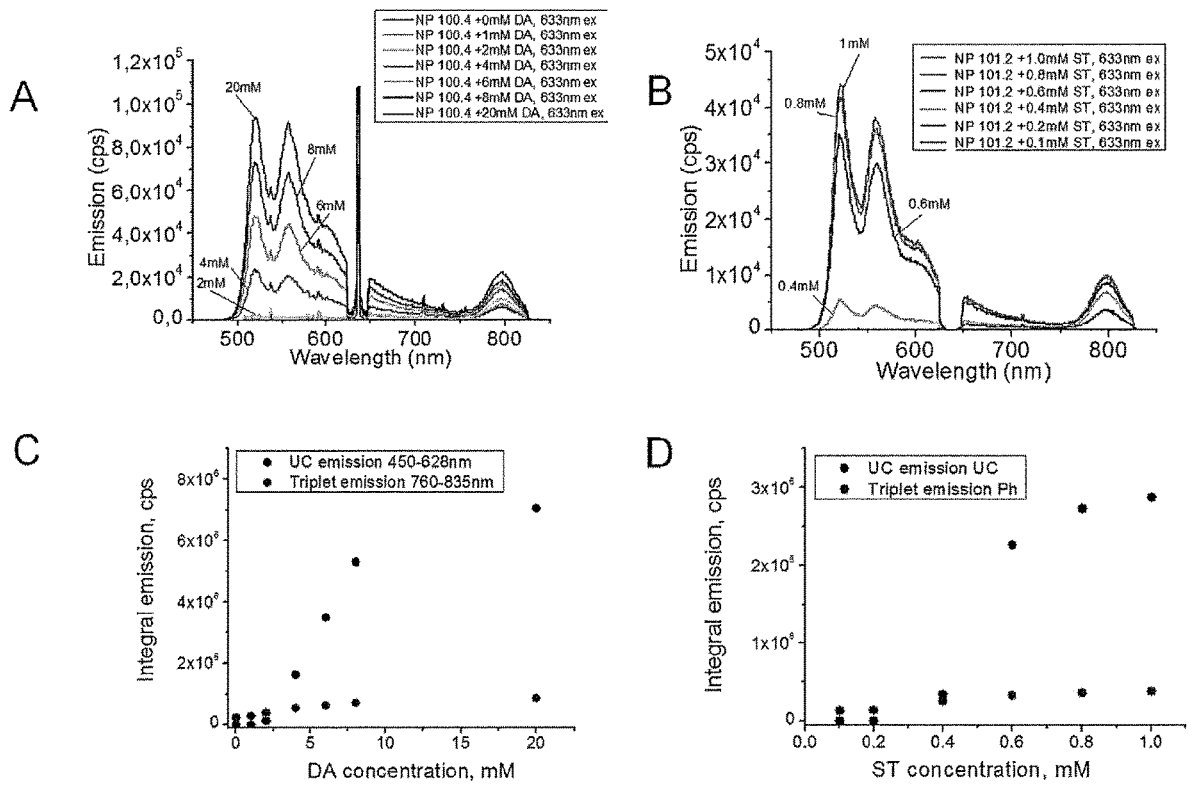
FIG. 2 shows: emission spectra of PUC-NP in aqueous dispersions at different serotonin and dopamine concentrations under 633 nm.
(A) and (B) Emission spectra of PUC-NPs at dopamine concentrations ranging from 1 mM to 20 mM (A) or at serotonin concentrations ranging from 0.1 mM to 1 mM (B), respectively.
(C) PUC emission and phosphorescence as a function of the dopamine (C) or serotonin (D) concentration. DA=dopamine; ST=serotonin
Figure 3:
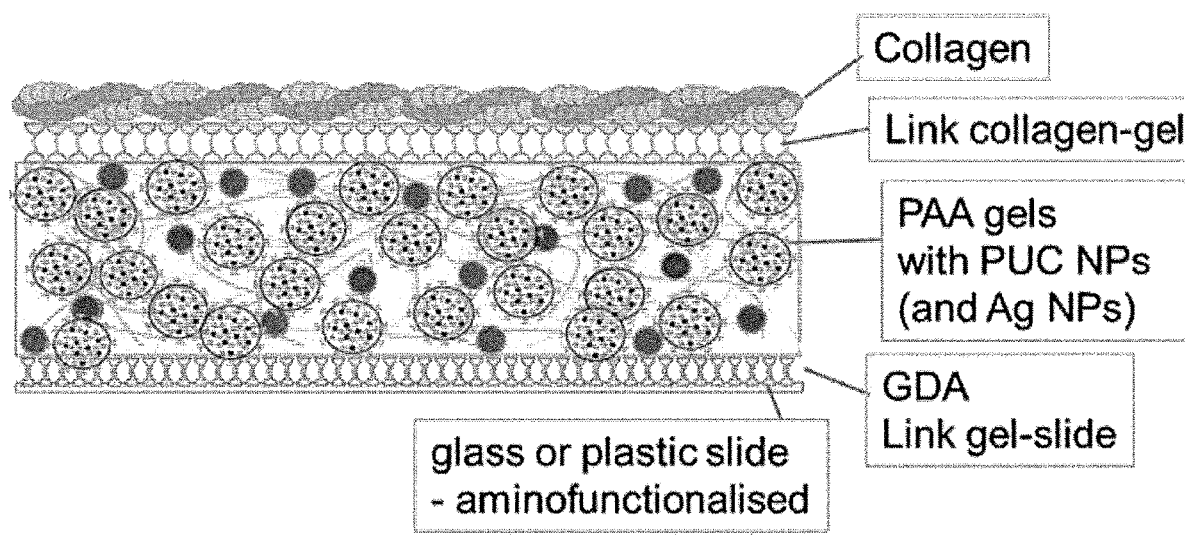
FIG. 3 shows: An embodiment of a sensor including and emissive layer (also sometimes referred to as "sensing layer" or "emissive sensing layer"=ESL) from organic nanoparticles with metal nanoparticles and antioxidant inside, attachment (link) layer for the cell adhesion layer, cell adhesion layer (in this case collagen). The same sensors have been used further in the examples. PAA=polyacrylamide; PUC NPs=photon upconversion nanoparticles; Ag NPs=silver nanoparticles; GDA=glutardialdehyde.
Figure 5:
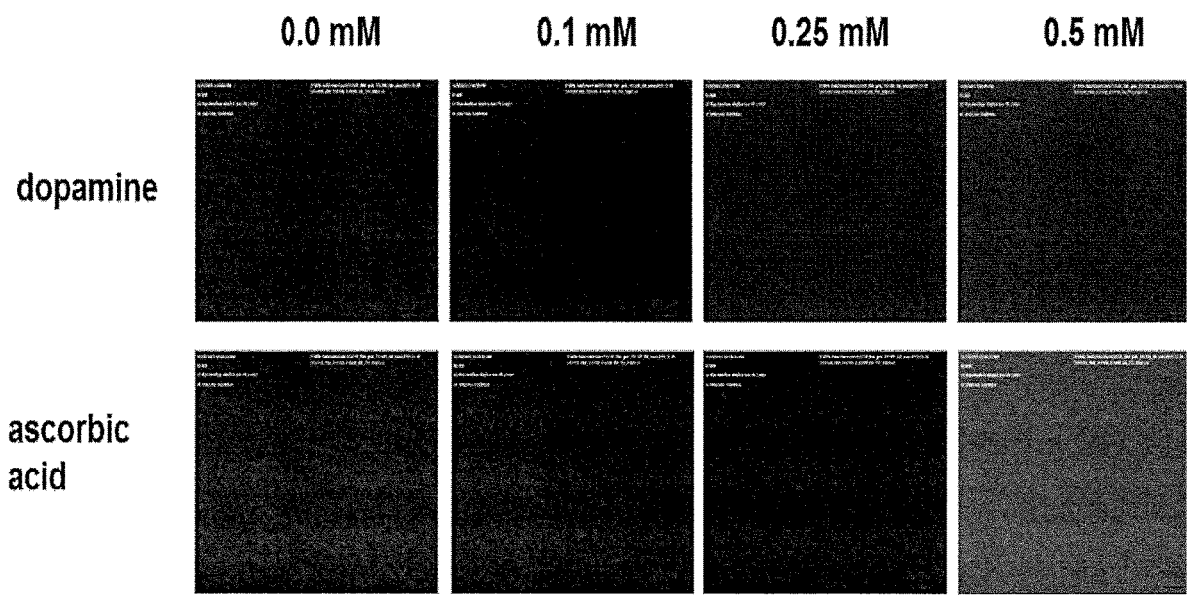
FIG. 5 shows: A comparison between sensing capabilities of emissive sensing layer (ESL) between ascorbic acid and dopamine at concentrations from 0.0 mM to 0.5 mM. Brightness of images was increased by 40%.
Figure 6:
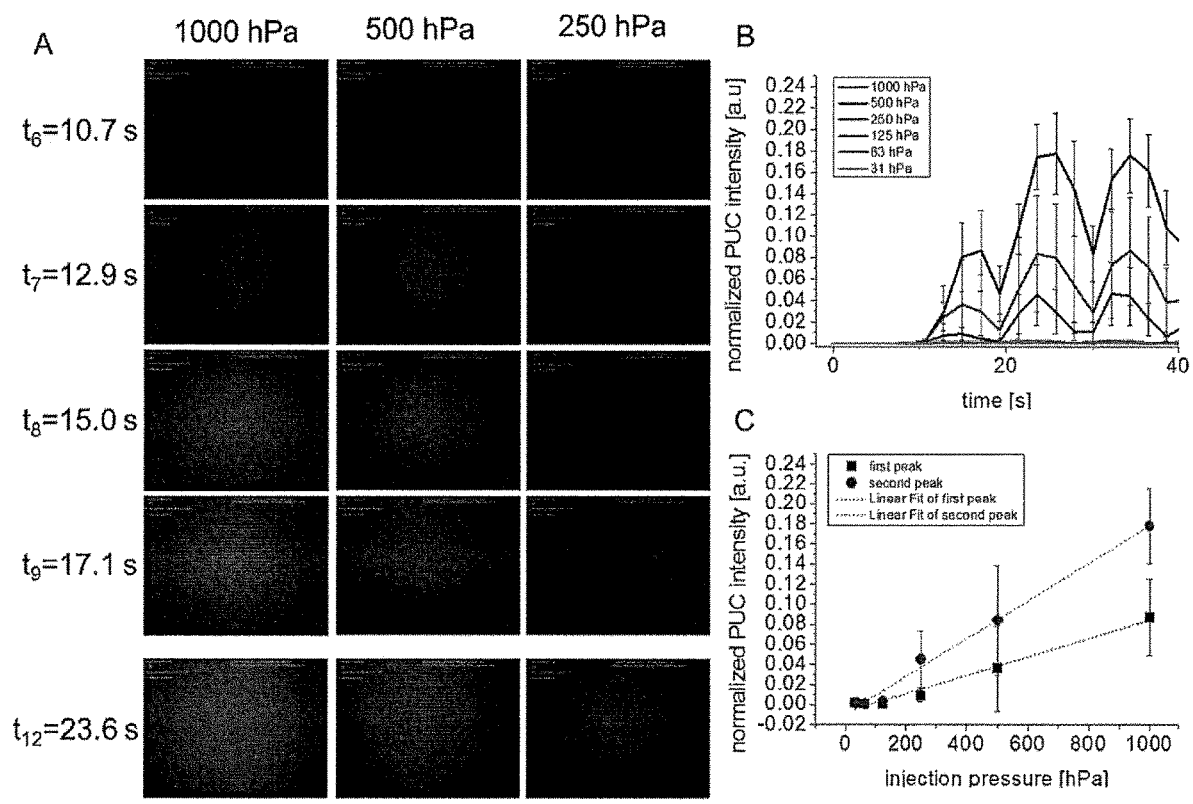
FIG. 6 shows:
(A) Visualization of local dopamine release from a micropipette positioned close to the layer surface using ESL under illumination with non-coherent light at 638 nm with an intensity of 2.3 W/cm$^2$. Dopamine was released from the pipette shortly before $t_5$ 10 s after start of the respective time series and then every 10 s. At $t_{12}$=23.6 s the maximum of PUC signal after the second release shortly before $t_{11}$=20 s. Release pressures were varied between 1000 hPa and 31 hPa. Images are represented at a gamma value of 0.45 (scale bar: 20 μm)
(B) normalized PUC intensity (n=3, mean±std) as a function of time after dopamine release from a micropipette. Dopamine solution droplet was first released at 10 s by the micropipette and then every 10 s.
(C) maximum normalized PUC intensity after first and second release of 2 mM dopamine droplet from a micropipette (mean±std) as a function of the release pressure. Data were fitted linearly without weights (dotted line).
Figure 7:
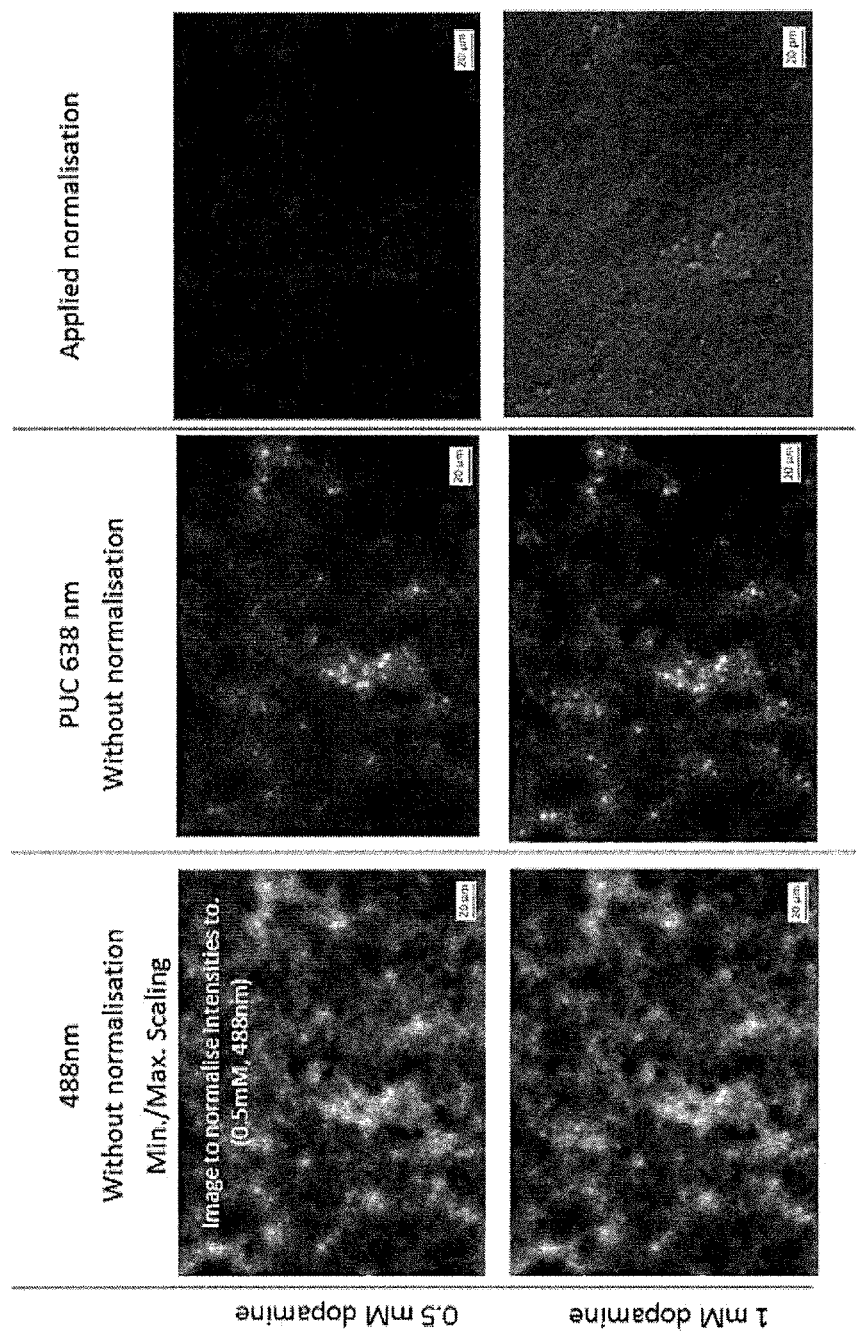
FIG. 7 shows data obtained with a sensor according to the present disclosure for a polymer matrix, i.e. the sensing layer is a polymer layer (formed by drying of polymer solution containing PUC NPs and other components according to the present disclosure).
(A) Control image of sensor in the presence of complete growth medium without neurotransmitter (sometimes abbreviated herein also as "NT") imaged in photon up-conversion mode. The medium is on top of the sensor/sensing layer. The control image is completely black.
(B)+(C) Sensor in presence of complete growth medium including 0.5 mM (B) and 1 mM (C) of the neurotransmitter dopamine, imaged in photon up-conversion mode. The images obtained are clearly brighter than the control image. The images shown in (A), (B) and (C) are photon up-conversion (PUC) images taken with an excitation of 640 nm (band filter centered at 640 nm with 14 nm transmission band). The up-conversion emission is detected through a band filter centered at 520 nm with 84 nm transmission band (for the microscope cube see below, FIG. 9). Standard imaging duration was 2 s. After each PUC image, a fluorescence image with 488 nm excitation for 100 ms (control or image for normalization) was taken.

Exemplary Nanoparticle Preparation Method Overview Summary:

Nanoparticles are prepared in this method by firing water [e.g. MilliQ, with controlled temperature and high speed (through electronic valves) into a temperature controlled, stirring solution of an organic phase [e.g. glycolic acid, heptadecylbenzene, polymethylmethacrylate, and Pd tetrabenzoporphyrin (PdTBP) sensitizer in dry THF under an inert $N_2$ atmosphere. Silver nanoparticles, [e.g. 4 nm Ag-Dodecanethiole NP or 50 nm SiO2 capped Ag nanoparticles are compared in FIG. 2] and antioxidant (e.g. lipoic acid in 2 different concentrations is shown in FIG. 2) can be added to the organic phase before mixing. The dispersion was then stirred under inert atmosphere for over an hour and the organic solvent (THF) evaporated under reduced pressure. The dispersion was filtered (Whatman 1 filter paper) to remove and large masses, and then centrifuged (100 K MWCO Corning Spin-X UF Concentrator 20 ml, to remove small molecules and particles. Nanoparticles of interest were collected in MilliQ water and stored cool (4° C.). This yields stable nanoparticles with a good polydispersity index (e.g. 0.2) and good zeta potential (e.g. −50 mV or higher).

Conclusion:

Organic nanoparticles with reproducible, controllable, repeatable size and optimised size distribution are successfully prepared via this method. Dyes and smaller nanoparticles have been successfully incorporated into the nanoparticles.

A protocol for NP synthesis was developed and optimized step by step. The set-up for the optimised procedure incorporates pressure and temperature control as well as fast speed mixing valves. Nanoprobes with completely reproducible and controlled variable properties (e.g. size and surface potential) were synthesized with the given set-up.

The nanoparticle dispersions developed by this method are highly emissive, biocompatible and can be used in a variety of biotechnological applications, especially for flow cytometry, live cell imaging, or—live cell functions imaging—e.g. neurotransmitters (or antioxidants) visualisation/imaging in neuronal or any other tissue or cell culture and/or as released by neuronal cells Example 2

Preparation of an Example of a Sensor Comprising an Emissive Sensing Layer

Here an exemplary method is presented to produce transparent emissive sensing layers (ESLs) composed of emissive nanoparticles as prepared in accordance with the present disclosure, i.e. photon upconversion nanoparticles (PUC NPs) embedded into a polymer matrix. The ESLs aim for the quantitative detection of different biomolecules secreted from living cells in cell culture with high spatiotemporal resolution. To achieve these goals the layers necessitate to exhibit excellent homogeneity, good stability under cell culture conditions as well as a high sensitivity and selectivity towards the target molecules.

This example describes an optimization of the sensing layer. Especially the homogeneity and the UC signal achieved by the layers in this example are very good. Additionally, stiffness of the layers can be tuned easily. The optimization includes change from a biopolymer matrix towards an organic polymer matrix. FIG. 10 shows the general structure and composition of an ESL, in particular a schematic drawing showing the general composition and structure of an emissive sensing layer (ESL). The ESL is prepared on a modified glass support and is afterwards functionalized with extracellular matrix proteins (ECM matrix proteins), such as collagen which facilitate biocompatibility of the layers.

Purpose/Aim:

The overall target is to develop a non-invasive tool to image cellular functions such as neurotransmitter release from neuronal cells (also in response to stimulation in real-time) using a standard epifluorescence microscopic setup. The layers are optimized for the use with neuronal cell models like PC-12 cells or human induced pluripotent stem cells. To achieve detection of target molecules from living cells the layers need to be permeable for the target molecules and in close proximity to the side of release. Furthermore the layers need to be stable for the duration of the cell culture.

Solution/Procedure (Experimental):

The preparation steps are conducted in a chemical laboratory under a fumehood. Pipette tips and Eppendorf cups were sterilized before use using in an autoclave (20 minutes @ 121° C.)

1. Procedure:

For optimization of ESLs an organic polymer matrix of polyacrylamide was used. This polymer forms an elastic hydrogel and can be varied in stiffness, which could also be of interest for cell culture applications. Polyacrylamide is used for cell culture applications like traction force microscopy. A detailed structure of the ESL and its components is shown in FIG. 10 which shows a schematic drawing showing the composition and structure of an emissive sensing layer (ESL).

1.1 Preparation of Activated Aminosilane-Coated Glass Slides:

To achieve attachment of the ESL to the glass support, the glass support is chemically modified. Aminofunctionalized glass slides (e.g NEXTERION A+, Schott GmbH, Jena) are used here as a starting point. Further activation is done by glutaraldehyde Preparation of hydrophobic coverslips:

Hydrophobic coverslips are needed to cover the polymerizing gel solution on the activated aminosilane-coated coverslips to prevent oxygen diffusion into the solution, which prevents polymerization and to achieve a flat surface of the final gel. Making the coverslips hydrophobic makes it easier to remove the glass slips after polymerization and helps not to damage the gel. Different standard procedures for hydrophobisation can be used, e.g. using RainX.

1.2 Preparation of Gel:

To prepare the ESL solution one needs the PUC, enhancer particles (Ag or Au nanoparticles) and polyacrylamide (PAA) gel stock solution. The stock solution can be prepared in different acrylamide/bisacrylamide solutions to adapt gel stiffness and density. The mixtures, which have been used, are summarized in the following table. Further mixtures can be found in Plotnikov et al. (Plotnikov et al., Methods in Cell Biology, 2014; "High-resolution Traction Force Microscopy" in Methods in Cell Biology, Volume 123, 2014, ISSN 0091-679X)

TABLE

| Mixtures of PAA gel stock solutions | | |
|---|---|---|
| Component | 4 kPa stock solution | 30 kPa stock solution |
| Acrylamide 40% | 3.75 ml | 3 ml |
| Bisacrylamid 2% | 0.75 ml | 1.4 ml |
| MilliQ | 0.50 ml | 0.60 ml |
| Total volume | 5.00 ml | 5.00 ml |

The PAA gel stock solution can be stored at 4° C. for at least a year.

In a first step, Ag NPs (40 nm, enhancer particles) are added to PUC NP solution in an 1.5 ml Eppendorf cup under sterile conditions. Then, PAA gel stock solution are added to the NP mixture and the complete solution is degassed either under argon or nitrogen atmosphere for 1 h. Furthermore, a 4% (w/w) ammonium-peroxosulfate (APS) solution is prepared in MilliQ. When everything is ready prepared, polymerization is induced by addition of TEMED and APS solution. The solution is quickly mixed using the 100 µl pipette and the gel solution isadded per well as a small droplet on the surface of an 8-well sticky slide on an activated aminosilane-coated glass slide. The droplet is quickly covered by a hydrophobic coverslip. The rest of the solution is used as a polymerization control. After 30 minutes of incubation at room temperature, polymerization is complete and the hydrophobic coverslips are removed carefully using a tweezer. The gels are washed 3 times with MilliQ before they are stored at 4° C.

Further modification of the ESL can be achieved by various measures, e.g. coating with e.g. polydopamine and extracellular matrix (ECM) proteins. Details about functionalization procedures can be found in Example 4.

Results of ESLs (Briefly):

3.1 Emissive Sensing Layers: Phase Contrast, Fluorescence and Upconversion

The emissive sensing layers prepared according to the aforementioned protocol were tested for fluorescence intensity at 488 nm and also upconversion intensity at 638 nm illumination wavelength under standardized conditions. Tests were conducted at the MSL imaging platform (Zeiss Axiovert inverted microscope, HXP lamp, 10× (tiled images) or 40× objective). To acquire the upconversion of the ESL, the layers were incubated for 2 h under $N_2$-atmosphere at 37° C. to remove molecular oxygen.

3.2 Emissive Sensing Layers: Dopamine Sensing

The layers were also tested for their sensing capabilities towards the targeted neurotransmitter dopamine. The results are shown in the figures, in particular FIGS. 4-7. Dopamine hydrochloride solution was dissolved either in PBS or HBSS.

Conclusion:

To improve homogeneity and sensitivity of the ESL polyacrylamide was used as matrix component. Two different acrylamide/bisacrylamide ratios were tested and both resulted in ESL with improved homogeneity, upconversion signal and transparency. Also the stability of gels under standard cell culture conditions could be validated. The ESL preparation is highly reproducible. ESLs are also stable over 3 weeks of incubation under cell culture conditions (see FIG. 8 for 24 h and 2 weeks stability results). Dopamine could be detected at relevant concentrations in the M range. To facilitate growth of cell cultures or iPS cells, layers are further functionalized.

Example 3

Further Functionalization of Emissive Sensing Layer to Increase Biocompatibility (Cell Compatibility)

Here an exemplary method to functionalize emissive sensing layers (ESLs) composed of PUC NPS (i.e. emissive nanoprobes and enhancer particles) embedded into a polyacrylamide matrix is presented. The ESLs aim for the quantitative detection of different biomolecules secreted from living cells in cell culture with high spatiotemporal resolution. To achieve these goals the layers should exhibit excellent homogeneity, good stability under cell culture conditions as well as a high sensitivity and selectivity towards the target molecules. Furthermore the layers have to facilitate cell growth of the desired cell type on the ESL. This report describes an exemplary functionalization of the layers presented in the previous example with poly-dopamine and ECM proteins like collagen or laminin to achieve a higher biocompatibility of the ESL.

Purpose/Aim:

The overall target is to develop a non-invasive tool to image cellular functions such as neurotransmitter release from single synapses in response to stimulation in real-time using a standard epifluorescence microscopic setup. The layers are optimized for the use with neuronal cell models like PC-12 cells or human induced pluripotent stem (iPS) cells. To achieve detection of target molecules from living cells the layers need to be permeable for the target molecules and in close proximity to the side of release. Furthermore the layers need to be stable for the duration of the cell culture. In this report we describe the functionalization of the ESL using poly-dopamine coating as an initial step followed by further functionalization by cationic polymers and extracellular matrix proteins to ensure adhesion and growth of cells on the ESL.

Solution/Procedure (Experimental):

The preparation steps are conducted in a sterile bench. Pipette tips and Eppendorf cups were sterilized before use using an autoclave (20 minutes @ 121° C.).

1. Procedure:

For optimization of ESLsan organic polymer matrix of polyacrylamide was used (polymer gel based sensing layers). This polymer forms an elastic hydrogel and can be varied in stiffness. Polyacrylamide is used for cell culture applications like traction force microscopy. The polyacrylamide gel itself does not allow cell adherence, which makes a functionalization of the ESLs necessary. Usually, Sulfo-SANPAH, a photo-activated linker molecule is used to functionalize PAA gels and make them biocompatible. (Plotnikov et al., Methods in Cell Biology, 2014, "High-resolution Traction Force Microscopy" in Methods in Cell Biology, Volume 123, 2014, ISSN 0091-679X) Tests with the present ESL showed that the functionalization with sulfo-SANPAH harms the upconversion signal of the layers and thus, its sensing capabilities. Here, a coating of poly-dopamine (poly-DA), an (optional) polymer and an ECM protein, e.g. collagen or laminin is used. Poly-dopamine has been shown to coat various surfaces robustly, while generating a hydrophilic layer, which can be further functionalized by components with reactive thiol- or amino-groups.

1.1 Poly-Dopamine Coating of the ESLs:

The ESLs in ibidi 8-well slides were taken out of the frigde and washed once with 300 µl of sterile Tris/TrisHCl pH 8.5 buffer. An e.g. 0.5 mM dopamine hydrochloride solution is prepared immediately before the coating procedure. This is critical since dopamine polymerizes quickly in higher pH buffers and solutions and forms dark aggregates, when stored for longer time, which can impact the transparency of the ESLs. The same is observed, when using more concentrated dopamine solutions. 300 µl of 0.5 mM dopamine solution is added to the ESLs and the ESLs are incubated for 1 h at room temperature. Afterwards, wells are either washed with 300 µl MilliQ or DPBS at least two times.

1.2 Biocompatible Coating of the Poly-Dopamine Coated ESLs:

The poly-dopamine coated layers are subject for further functionalization using a further polymer first or directly an ECM protein, which is dependent on the investigated cell type. The tested conditions are summarized in the following Table.

TABLE

Functionalization of poly-dopamine coated ESL for different cell types

| Component | PC-12 cells | ReproCell iPS dopaminergic neurons ReproNeuro | CDI iCell DopaNeurons/ PC-12 cells |
|---|---|---|---|
| 0.002% Poly-L-Lysine | — | yes | — |
| 0.01% Poly-L-Ornithine | — | — | yes |
| 1 mg/ml Collagen from bovine skin | yes | — | — |
| 3.3 µg/ml Laminin Coating solution (ReproCell) | — | yes | yes |

1.2.1 ESL Coating for PC-12 Cell Culture:

The washed poly-dopamine coated ESLs were covered by 150 µl of a 1.0 mg/ml solution of collagen in DPBS without calcium and magnesium and incubated for 1 h at room temperature. Afterwards, wells were washed 2 to 3 times with DPBS. These layers were used for culturing PC-12 cells.

1.2.2 Coating for ReproCell ReproNeuro iPS Cells:

The washed poly-dopamine coated ESLs were covered by a 0.002% poly-L-lysine (PLL) solution in DPBS without calcium and magnesium and incubated for 2 h at 37° C. In the meantime, the coating solution (ReproCell, 65 µl) was diluted in 600 µl DPBS. The PLL solution was removed completely and ESLs were washed two times with DPBS. In a next step, 95 µl of the coating solution were added to the wells containing ESLs and the wells were incubated at 37° C. and 5% $CO_2$ overnight. The coating solution was aspirated from wells directly before plating the iPS neurons without further washing steps.

1.2.3 Coating for CDI iCell DopaNeurons iPS Cells/PC-12 Cells:

Laminin solution was taken out of the fridge thawn at room temperature under sterile conditions. The MilliQ washed poly-dopamine coated ESLs were covered by 300 µl of a 0.01% poly-L-ornithin (PLO) solution and were incubated for 1 h at room temperature. Directly before washing the wells in the next step, a 1:300 dilution of laminin in DPBS without calcium and magnesium was prepared. The PLO solution was removed completely using an aspirator and wells were washed thoroughly with 600 µl DPBS twice. In a next step, 300 µl of the laminin solution were added to the wells containing ESLs and the wells were wrapped in parafilm and incubated overnight at 4° C. The laminin solution was aspirated from wells directly before plating the CDI iCell DopaNeurons iPS neurons and PC-12 cells without further washing steps.

An exemplary scheme of functionalization steps for different cell types is shown in FIG. 13 which shows a schematic drawing showing examples of coating steps and conditions for the culture of different cell types.

Results (Briefly):

3.3 Culture of PC-12 Cells on Poly-Dopamine+Collagen Coated ESLs:

ESLs functionalized with poly-dopamine and collagen were used to culture PC-12 cells on the layers. PC-12 cells were found to grow well on the functionalized layers.

This demonstrates that the functionalization with poly-DA and collagen allows cells adhesion and spreading on the PAA gels. The PC-12 cells on gels show normal morphology.

3.4 Culture of ReproCell ReproNeuro iPS Cells on Poly-Dopamine+PLL+Coating solution coated ESLs:

ESLs functionalized with poly-dopamine, poly-L-lysine and ReproCell coating solution were used to culture ReproCell ReproNeuro iPS cells on the layers. ReproCell ReproNeuro iPS cells were found to grow well on the functionalized layers.

On both substrates, the iPS cells exhibit similar, neuronal morphology and iPS cells could by cultured stably on the functionalized ESL for more than 2 weeks. The total amount of cell attached to the ESL was slightly less as compared to standard 96-well plates.

3.5 Culture of CDI iCell DopaNeuron iPS Cells and PC-12 Cells Poly-Dopamine+PLO+Laminin Coated ESLs:

ESLs functionalized with poly-dopamine, poly-L-lysine and laminin were used to culture CDI iCell DopaNeuron iPS cells on the layers. CDI iCell DopaNeuron iPS cells as well as PC-12 cells were found to grow well on the functionalized layers.

Cells adhered well on the functionalized ESL and cells show neurite outgrowth, which seems to be less pronounced compared to neurite outgrowth of cells plated on a standard 24-well plate with the double coat of PLO and laminin.

Conclusion:

The optimized ESLs with the poly-acrylamide matrix could be successfully functionalized using poly-dopamine coating in a first step. In further steps, a matrix, which fits the requirements for the distinct cell type, was applied. For PC-12 cells, a coating with collagen was sufficient, while neuronal iPS cells from ReproCell and CDI required a double coat of a further polymer (PLO or PLL) and coating with an additional coating solution from ReproCell or laminin. The double coat of PLO and laminin was also suitable for PC-12 culture. Thus, the requirements for sensing dopamine release directly from cells are fulfilled.

Thus, the foregoing discussion discloses and describes merely exemplary embodiments of the present disclosure. As will be understood by those skilled in the art, the present disclosure may be embodied in other specific forms without departing from the spirit or essential characteristics thereof. Accordingly, the disclosure of the present disclosure is intended to be illustrative, but not limiting of the scope of the disclosure, as well as other claims. The disclosure, including any readily discernible variants of the teachings herein, define, in part, the scope of the foregoing claim terminology such that no inventive subject matter is dedicated to the public.

The present application claims priority to European Patent Application 16163436.5 filed by the European Patent Office on Mar. 31, 2016, the entire contents of which being incorporated herein by reference.

The invention claimed is:

1. A sensor for detection of an analyte, comprising:
a biocompatible sensing layer comprising a matrix, organic nanoparticles comprising an organic component and embedded in said matrix, and metal nanoparticles distributed within said matrix such that the organic nanoparticles do not contain metal nanoparticles and that the organic nanoparticles have molecules or chemical groups attached to surfaces thereof that bind to the analyte or have an enzymatic activity to detect the analyte,
wherein said matrix is a polymer matrix or a polymer gel matrix, said organic nanoparticles include a light emitter and a sensitizer therein such that the organic nanoparticles emit light by photon up-conversion emission in the presence of said analyte and do not emit light by photon up-conversion emission in the absence of said analyte, and said metal nanoparticles are a metal material comprising at least one selected from the group consisting of Ag, Au, Co, Al, Cu, and a nitride of a transition metal.

2. The sensor according to claim 1, wherein said analyte is a biomolecule.

3. The sensor according to claim 1, wherein said matrix is an organic matrix.

4. The sensor according to claim 1, wherein said sensitizer absorbs light at a first wavelength region $w \leq \lambda_1 \leq x$, and said light emitter emits light at a second wavelength region $y \leq \lambda_2 \leq z$, wherein $\lambda_2 \leq \lambda_1$, and upon absorption of light by said sensitizer at said first wavelength region $w \leq \lambda_1 \leq x$, said light emitter emits light at said second wavelength region $y \leq \lambda_2 \leq z$.

5. The sensor according to claim 4, wherein said light emitted by said light emitter at said second wavelength region $\lambda_2$ is due to an up-conversion process based on triplet-triplet annihilation which up-conversion process occurs upon ab sorption of light by said sensitizer at said first wavelength region $\lambda_1$.

6. The sensor according to claim 4, wherein the light emitted by said light emitter has a wavelength in the range of from 360 to 750 nm, and/or said sensitizer absorbs light at a wavelength in the range of from 450 to 1600 nm.

7. The sensor according to claim 1, further comprising:
an enhancement layer formed on the biocompatible sensing layer and including metal nanoparticles distributed therein,
wherein said metal nanoparticles in the enhancement layer comprise at least one metal material selected from the group consisting of Ag, Au, and Co, and said metal nanoparticles in the biocompatible sensing layer and enhancement layer are plasmonic and/or magnetic.

8. The sensor according to claim 1, wherein said biocompatible sensing layer further comprises an antioxidant.

9. The sensor according to claim 1, wherein said organic nanoparticles include functional groups on surfaces thereof such that the functional groups allow to covalently couple the molecules to the organic nanoparticles.

10. The sensor according to claim 1, further comprising:
an attachment layer which immobilizes the biocompatible sensing layer on a substrate.

11. The sensor according to claim 1, further comprising:
a cell adherence layer on which cultured cells are immobilized.

12. The sensor according to claim 1, wherein said analyte is selected from the group consisting of a neurotransmitter, an antioxidant, an oxygen and a reactive oxygen species, and a hormone.

13. The sensor according to claim 1, wherein said matrix is a polymer matrix or polymer gel matrix comprising a material selected from the group consisting of polyacrylamide, polyornithine, bovine serum albumin, collagen, gelatin, chitosan, poly-l-lysine, laminin, a gel-forming peptide, a hydromatrix peptide, and a combination thereof.

14. The sensor according to claim 1, wherein said light emitter has a structure represented by Formula (I) or (II) or includes a molecule having the structure Formula (I) or (II), Formula (I)

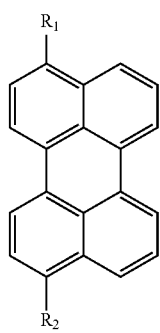

Formula (II)

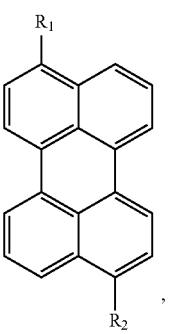

wherein $R_1$ and $R_2$ are independently selected from the group consisting of hydrogen and a moiety with the structure of Formula (III), wherein at least one of $R_1$ and $R_2$ is a moiety with the structure of Formula (III), Formula (III)

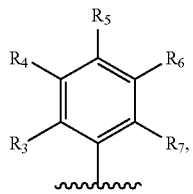

wherein $R_3$, $R_4$, $R_5$, $R_6$ and $R_7$ are independently selected from the group consisting of H, F, and tri-fluoro-methyl (—$CF_3$), and at least one of $R_3$, $R_4$, $R_5$, $R_6$ and $R_7$ is F or tri-fluoro-methyl (—$CF_3$).

15. The sensor according to claim 1, wherein said sensitizer has a structure of Formula (XXVII), Formula (XXVIII), Formula (IXXX), Formula (XXX) or Formula (XXXI) or includes a molecule having a structure of Formula (XXVIII), Formula (IXXX), Formula (XXX) or Formula (XXXI), Formula (XXVII)

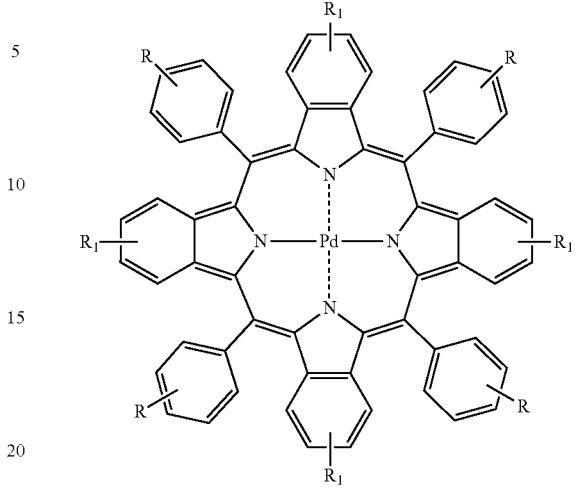

Formula (XXVIII)

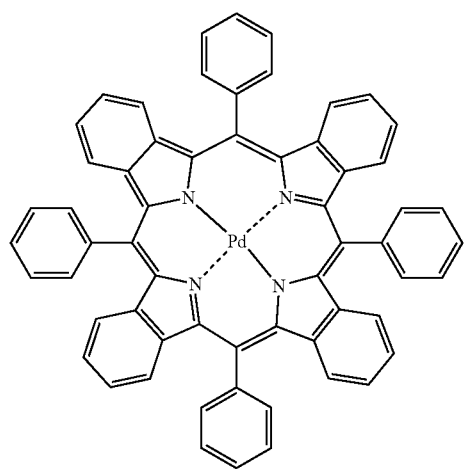

(IXXX)

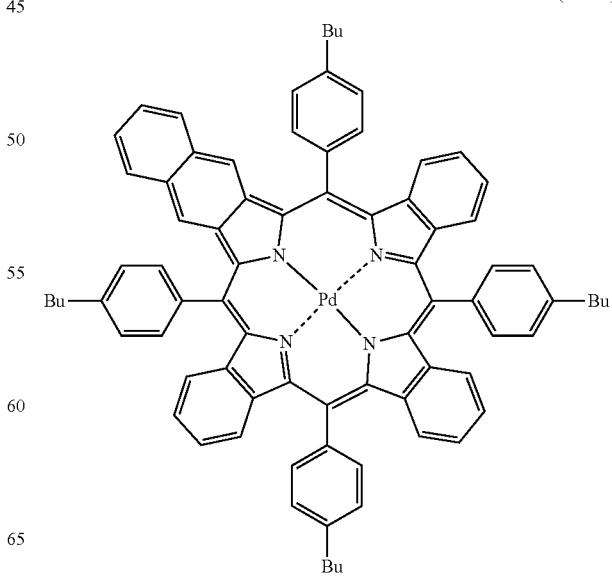

-continued

Formula (XXX)

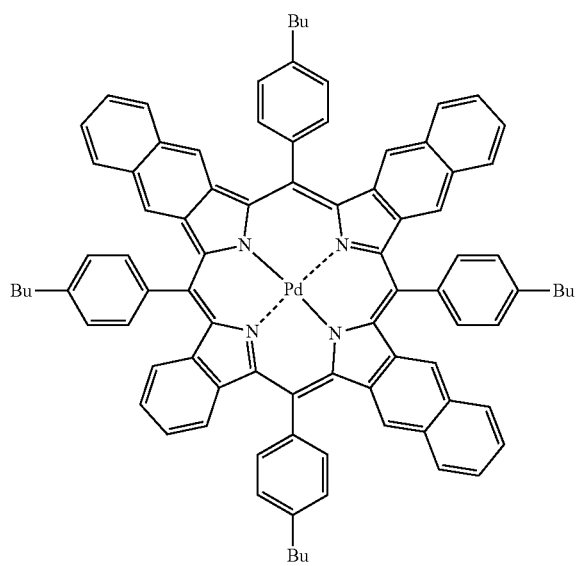

Formula (XXXI)

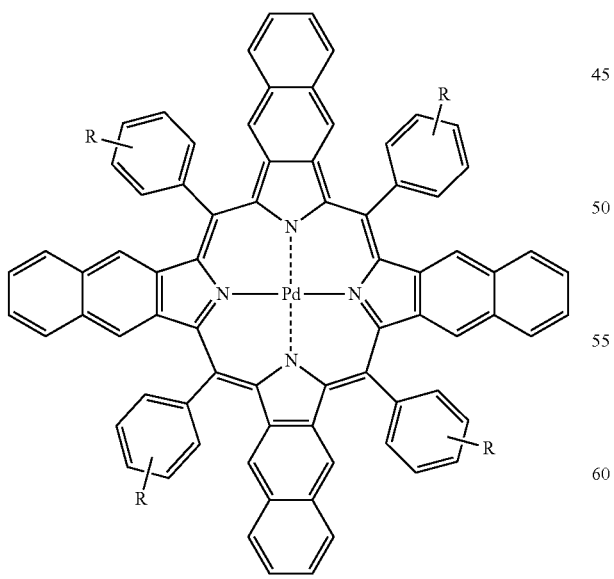

wherein $R_1$ is hydrogen, a linear or branched alkyl group, or a benzene ring, and R is a linear or branched alkyl group.

16. The sensor according to claim 1, wherein said light emitter is a molecule selected from the group consisting of an anthracene, a perylene, a perylene derivative, a coumarin, and a BODIPY dye; or said light emitter has the structure of Formula (X) or includes a molecule having the structure of Formula (X), Formula (X)

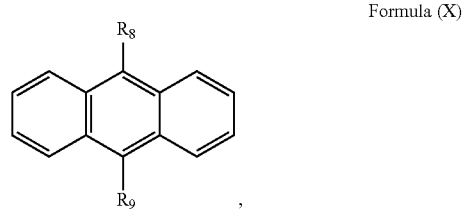

where $R_8$ and $R_9$ are independently selected from the group consisting of hydrogen and a moiety with the structure of Formula (XI), at least one of $R_8$ and $R_9$ is a moiety with the structure of Formula (XI), Formula (XI)

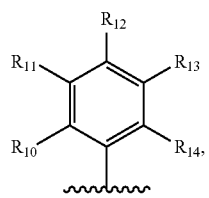

where $R_{10}$, $R_{11}$, $R_{12}$, $R_{13}$ and $R_{14}$ are independently selected from the group consisting of H, F, and tri-fluoro-methyl (—$CF_3$), and at least one of $R_{10}$, $R_{11}$, $R_{12}$, $R_{13}$ and $R_{14}$ is F or tri-fluoro-methyl (—$CF_3$); or said light emitter has a structure or includes a molecule having the structure selected from the group consisting of

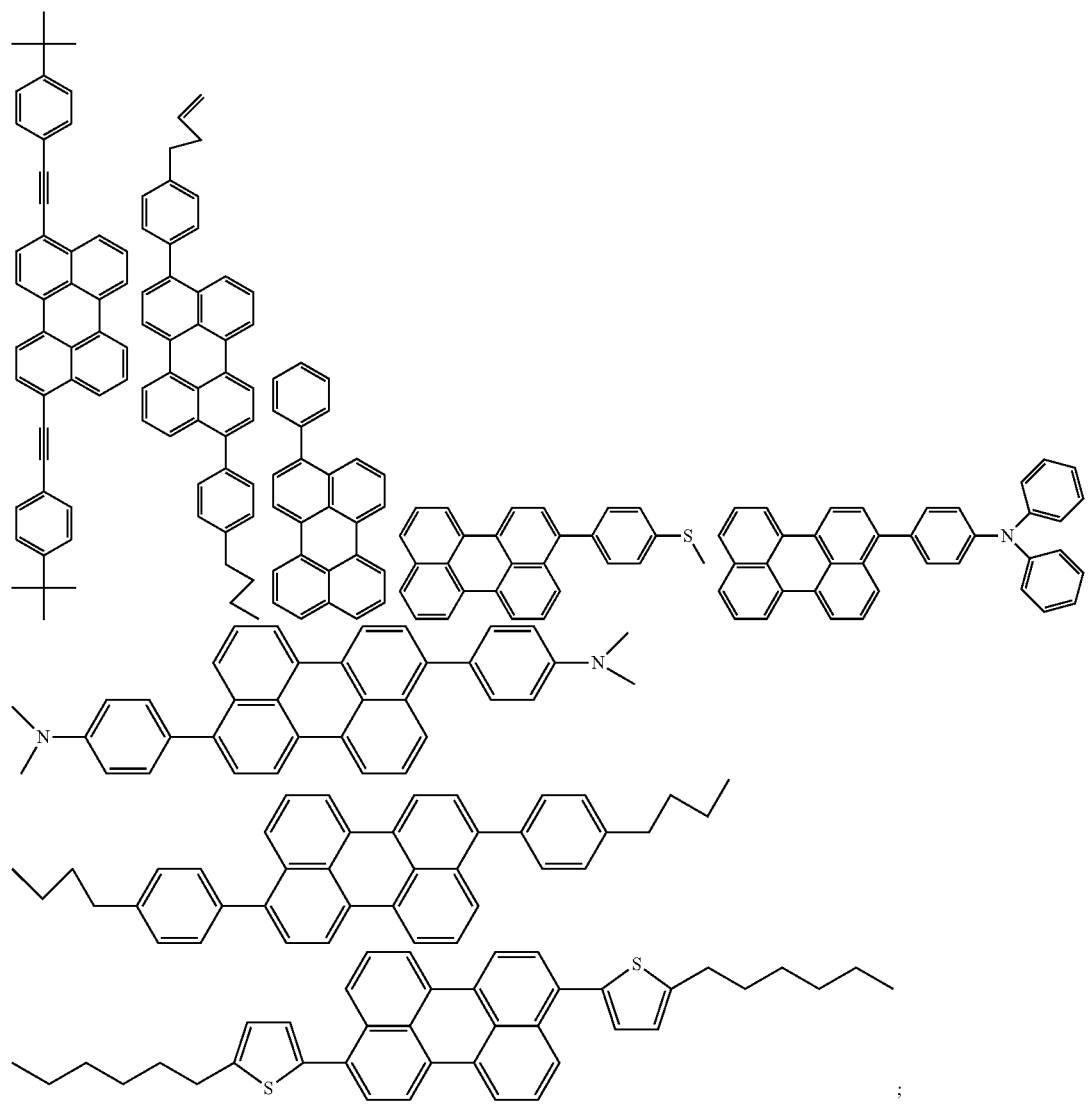
or said light emitter has a structure of Formula (XXIII), (XXIV) or (XXV) or includes a molecule having the structure of Formula (XXIII), (XXIV) or (XXV),
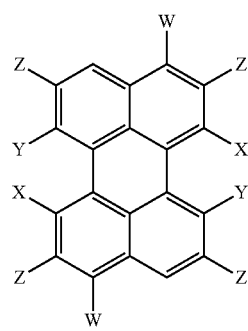
Formula (XXIII)
-continued
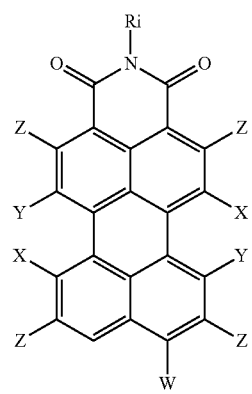
Formula (XXIV)

Formula (XXV)

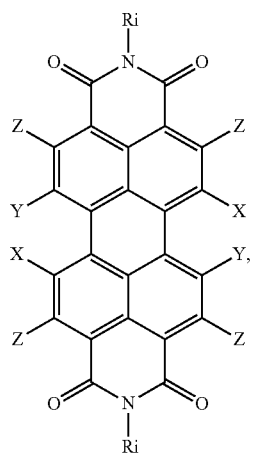

where W is one selected from the groups consisting of

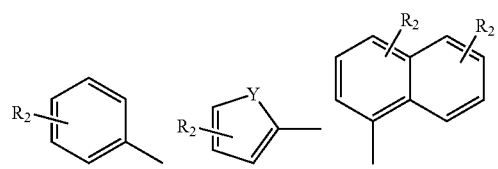

Y in W is one selected from the group consisting of CH$_2$, S, O, Se and N—R$_2$, and R$_2$ is one selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a halogenated alkyl group, a heteroaryl group, a fluorenyl group, an amino group, a nitro group, an OH group, an SH group, and a group —O—R$_3$, R$_3$ is one selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a halogenated alkyl group, a heteroaryl group and a fluorenyl group, X and Y in Formulae XXIII-XXV are one independently selected from the groups consisting of

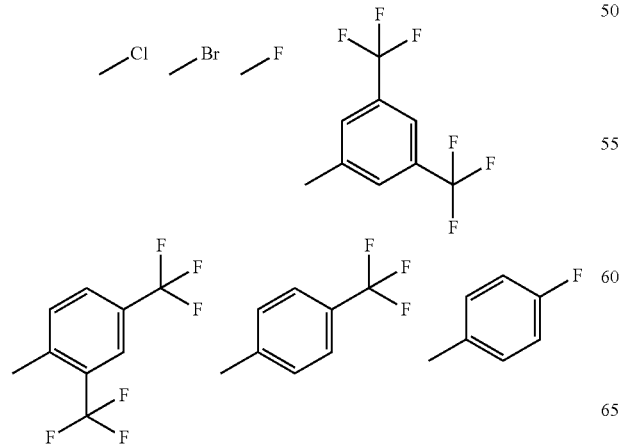

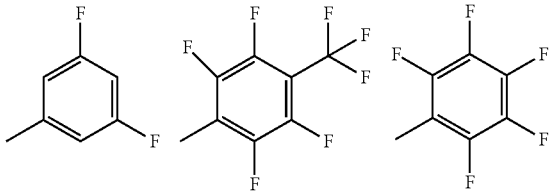

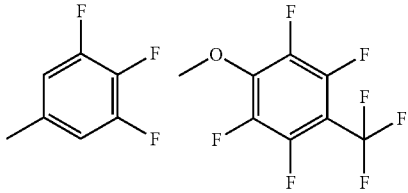

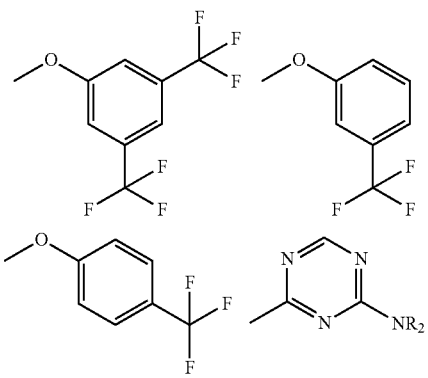

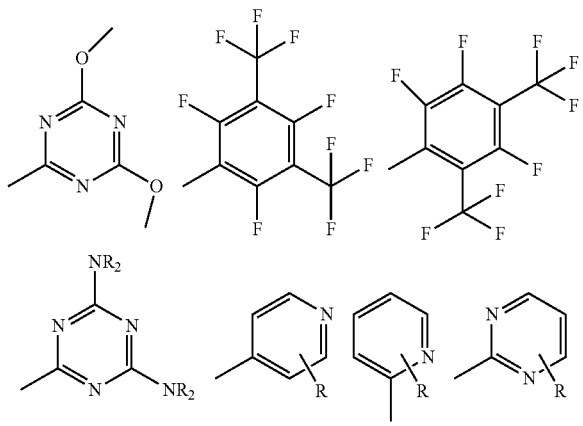

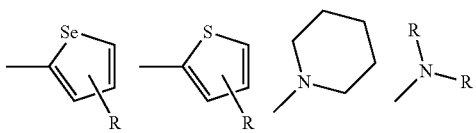

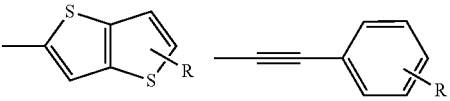

where R is one selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a halogenated alkyl group, a heteroaryl group, a fluorenyl group, an amino group, a nitro group, an OH group, an SH group, and a group —O—$R_3$, $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a halogenated alkyl group, a heteroaryl group and a fluorenyl group, Z in Formulae XXIII-XXV is one selected from the groups consisting of where $R_2$ is one selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a halogenated alkyl group, a heteroaryl group, a fluorenyl group, an amino group, a nitro group, an OH group, an SH group, and a group —O—$R_3$, $R_3$ is selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a halogenated alkyl group, a heteroaryl group and a fluorenyl group, Ri in Formulae XXIII-XXV is one selected from the groups consisting of where R is one selected from the groups consisting of

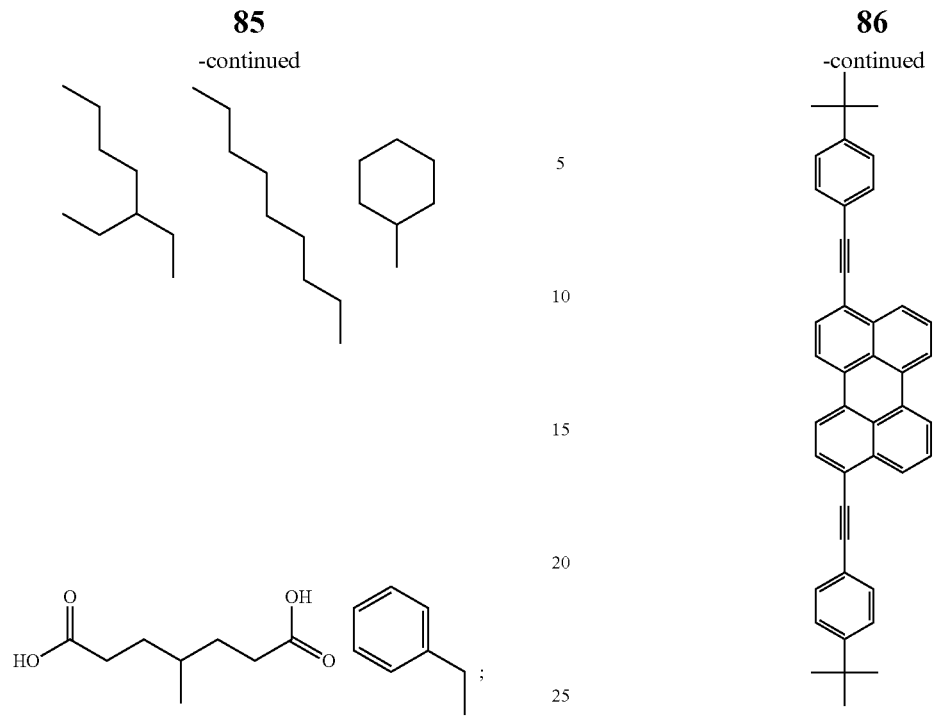

or said light emitter has a structure selected from one selected from the group consisting of

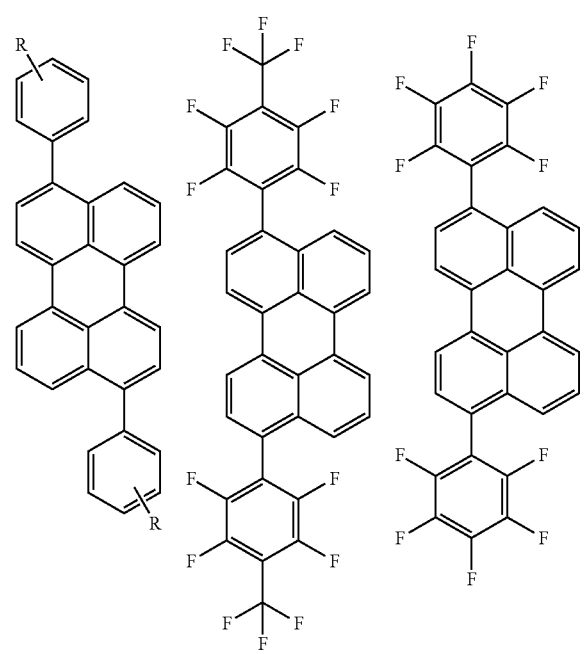

where R is a linear or branched alkyl group, has a structure of Formula (XXVI) or includes a molecule having the structure of Formula (XXVI), Formula (XXVI)

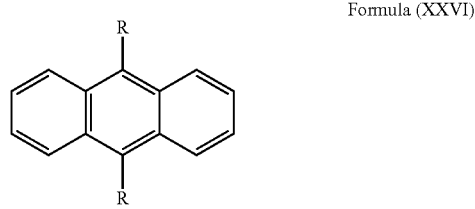

where R is one selected from the group consisting of

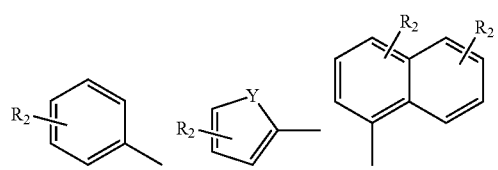

where Y is one selected from the group consisting of $CH_2$, S, O, Se and N—$R_2$, and $R_2$ is one selected from the group consisting of H, a linear alkyl group, a branched alkyl group, a cycloalkyl group, a halogenated alkyl group, a halogen atom, an alkyl sulfanyl group, an aryl sulfanyl group, an amino alkyl group, an amino aryl group, an aryl group, a halogenated alkyl group, a heteroaryl group, a fluorenyl group, an OH group, an SH group, and a group —O—$R_3$, $R_3$ is one selected from the group consisting of a linear alkyl group, a branched alkyl group, a cycloalkyl group, a halogenated alkyl group, an alkyl sulfanyl group, an aryl sulfanyl group, an amino alkyl group, an amino aryl group, an aryl group, a halogenated alkyl group, a heteroaryl group and a fluorenyl group, or R is one selected from the group consisting of

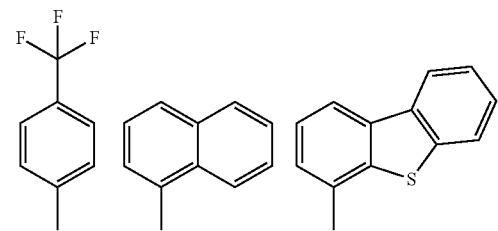

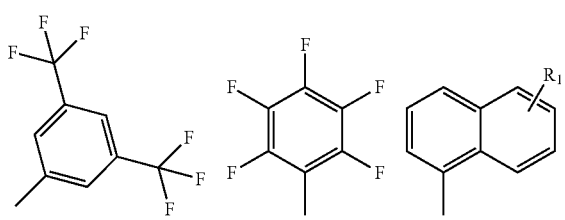

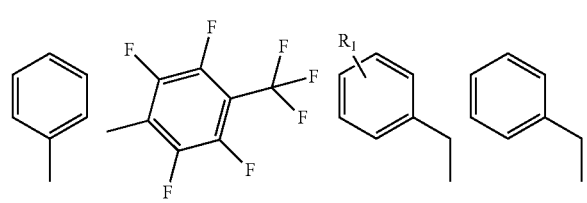

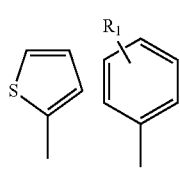

where $R_1$ is a linear or branched alkyl group; or said light emitter has a structure or includes a molecule having the structure selected from the group consisting of where R is a linear or branched alkyl group, and/or said sensitizer is or includes a porphyrin or a phthalocyanine.

17. The sensor according to claim 1, wherein said metal nanoparticles are plasmonic and/or magnetic.

* * * * *